United States Patent
Fox et al.

(10) Patent No.: US 10,271,842 B2
(45) Date of Patent: Apr. 30, 2019

(54) ANVIL STABILIZATION FEATURES FOR SURGICAL STAPLER

(71) Applicant: Ethicon Endo-Surgery, LLC, Guaynabo, PR (US)

(72) Inventors: William D. Fox, New Richmond, OH (US); Richard F. Schwemberger, Cincinnati, OH (US); Brian F. DiNardo, Cincinnati, OH (US); Christopher C. Miller, Loveland, OH (US); Omar J. Vakharia, Cincinnati, OH (US); Charles J. Scheib, Loveland, OH (US)

(73) Assignee: Ethicon LLC, Guaynabo, PR (US)

( * ) Notice: Subject to any disclaimer, the term of this patent is extended or adjusted under 35 U.S.C. 154(b) by 720 days.

(21) Appl. No.: 14/751,506

(22) Filed: Jun. 26, 2015

(65) Prior Publication Data

US 2016/0374670 A1    Dec. 29, 2016

(51) Int. Cl.
*A61B 17/072* (2006.01)
*A61B 17/068* (2006.01)
(Continued)

(52) U.S. Cl.
CPC .......... *A61B 17/068* (2013.01); *A61B 17/072* (2013.01); *A61B 17/07207* (2013.01);
(Continued)

(58) Field of Classification Search
CPC ................ A61B 17/068; A61B 17/072; A61B 17/07207; A61B 17/115; A61B 17/1155;
(Continued)

(56) References Cited

U.S. PATENT DOCUMENTS

| | | |
|---|---|---|
| 5,205,459 A | 4/1993 | Brinkerhoff et al. |
| 5,271,543 A | 12/1993 | Grant et al. |

(Continued)

FOREIGN PATENT DOCUMENTS

| | | |
|---|---|---|
| CN | 201 481 477 U | 5/2010 |
| EP | 0 536 882 A2 | 4/1993 |

(Continued)

OTHER PUBLICATIONS

European Search Report, Partial, dated Nov. 3, 2016 for Application No. EP 16176147.3, 8 pgs.

(Continued)

*Primary Examiner* — Scott A Smith
(74) *Attorney, Agent, or Firm* — Frost Brown Todd LLC

(57) ABSTRACT

A surgical instrument for stapling tissue includes a body, a shaft assembly, and an anvil. The shaft assembly includes a stapling head assembly and an actuator. The anvil is configured to be selectively coupled to the actuator. The anvil is configured to cooperate with the stapling head assembly to staple tissue. The anvil comprises a head and a shank extending from the head. The shank includes a proximal end, a distal end, a lumen, and an engagement feature. The engagement feature is in communication with the lumen such that the engagement feature is configured to move relative to the axis in response to the rod being directed into the lumen. The engagement feature is configured to selectively couple the shank to the actuator. The proximal end of the engagement feature is radially fixed relative to the axis.

19 Claims, 38 Drawing Sheets

(51) Int. Cl.
*A61B 17/115* (2006.01)
*A61B 17/00* (2006.01)

(52) U.S. Cl.
CPC . *A61B 17/1155* (2013.01); *A61B 2017/00433* (2013.01); *A61B 2017/00473* (2013.01); *A61B 2017/00477* (2013.01); *A61B 2017/07214* (2013.01)

(58) Field of Classification Search
CPC .......... A61B 17/00491; A61B 17/1114; A61B 17/0686; A61B 17/0644; A61B 2017/07214; A61B 2017/00477; A61B 2017/00473; A61B 2017/00433
USPC .............. 227/19, 175.1, 175.2, 176.1, 180.1; 606/139, 153, 219
See application file for complete search history.

(56) References Cited

U.S. PATENT DOCUMENTS

| | | | |
|---|---|---|---|
| 5,271,544 A | 12/1993 | Fox et al. | |
| 5,275,322 A | 1/1994 | Wolf et al. | |
| 5,285,945 A | 2/1994 | Brinkerhoff et al. | |
| 5,292,053 A | 3/1994 | Smith et al. | |
| 5,333,773 A | 8/1994 | Main et al. | |
| 5,350,104 A | 9/1994 | Main et al. | |
| 5,533,661 A | 7/1996 | Main et al. | |
| 5,669,918 A * | 9/1997 | Balazs | A61B 17/1155 227/176.1 |
| 5,718,360 A | 2/1998 | Green et al. | |
| 5,758,814 A * | 6/1998 | Gallagher | A61B 17/115 227/176.1 |
| 6,945,444 B2 | 9/2005 | Gresham et al. | |
| 7,794,475 B2 | 9/2010 | Hess et al. | |
| 7,922,743 B2 | 4/2011 | Heinrich et al. | |
| 8,231,042 B2 * | 7/2012 | Hessler | A61B 17/1114 227/175.1 |
| 8,360,296 B2 | 1/2013 | Zingman | |
| 8,408,439 B2 | 4/2013 | Huang et al. | |
| 8,453,914 B2 | 6/2013 | Laurent et al. | |
| 8,485,414 B2 * | 7/2013 | Criscuolo | A61B 17/00491 227/175.1 |
| 8,496,157 B2 * | 7/2013 | Olson | A61B 17/1155 227/176.1 |
| 8,733,611 B2 * | 5/2014 | Milliman | A61B 17/0686 227/175.2 |
| 8,870,911 B2 * | 10/2014 | Williams | A61B 17/115 606/185 |
| 8,910,847 B2 | 12/2014 | Nalagatla et al. | |
| 9,161,803 B2 | 10/2015 | Yates et al. | |
| 2005/0023325 A1 * | 2/2005 | Gresham | A61B 17/115 227/176.1 |
| 2010/0096435 A1 * | 4/2010 | Fuchs | A61B 17/1114 227/179.1 |
| 2012/0065665 A1 * | 3/2012 | Williams | A61B 17/115 606/207 |
| 2014/0144968 A1 | 5/2014 | Shelton | |
| 2014/0144969 A1 | 5/2014 | Scheib et al. | |
| 2014/0151429 A1 | 6/2014 | Scheib et al. | |
| 2014/0151430 A1 | 6/2014 | Scheib et al. | |
| 2014/0158747 A1 | 6/2014 | Measamer et al. | |
| 2014/0166717 A1 | 6/2014 | Swayze et al. | |
| 2014/0166718 A1 | 6/2014 | Swayze et al. | |
| 2014/0166728 A1 | 6/2014 | Swayze et al. | |
| 2015/0083772 A1 | 3/2015 | Miller et al. | |
| 2015/0083773 A1 | 3/2015 | Measamer et al. | |
| 2015/0083774 A1 | 3/2015 | Measamer et al. | |
| 2015/0083775 A1 | 3/2015 | Leimbach et al. | |

FOREIGN PATENT DOCUMENTS

| | | |
|---|---|---|
| EP | 1 857 058 A1 | 11/2007 |
| EP | 2 676 617 A1 | 12/2013 |

OTHER PUBLICATIONS

European Search Report, Extended, and Written Opinion dated Feb. 24, 2017 for Application No. EP 16176147.3, 11 pgs.
International Search Report and Written Opinion dated Jan. 11, 2017 for Application No. PCT/US2016/038956, 18 pgs.

* cited by examiner

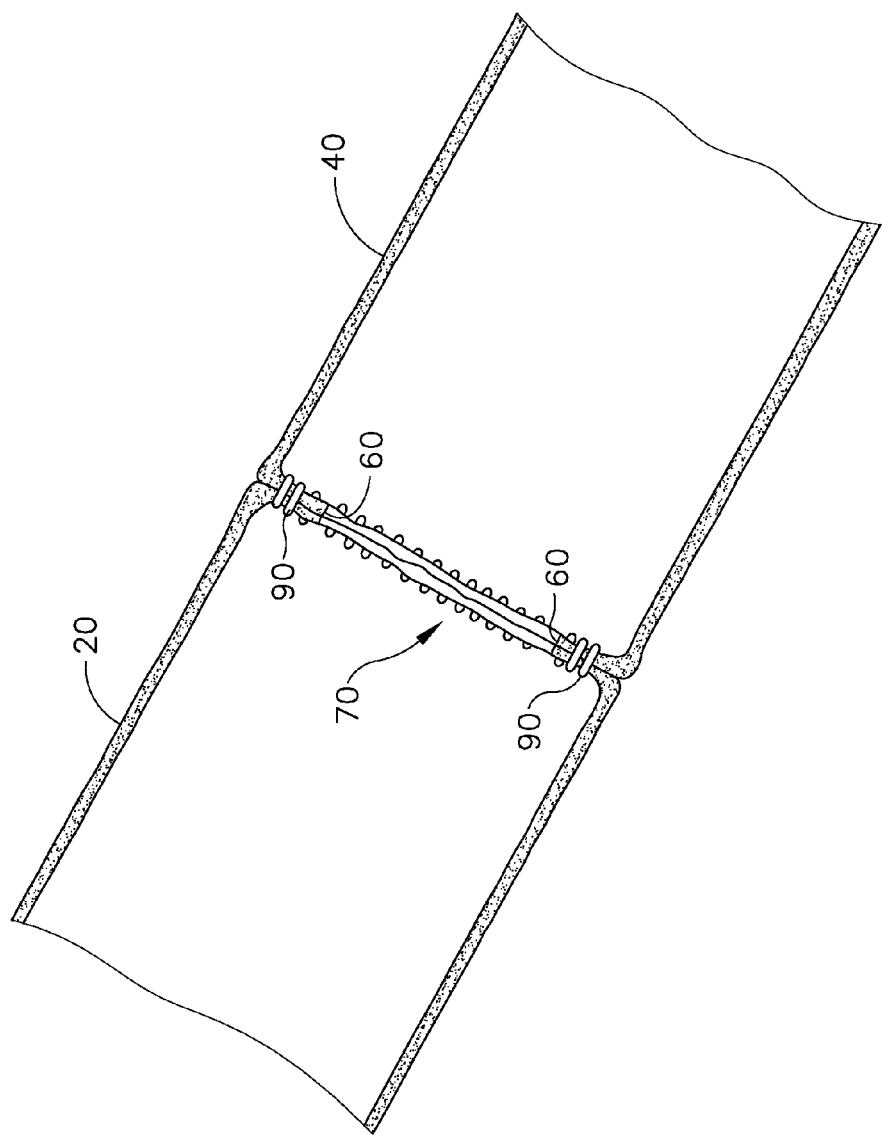

ANVIL STABILIZATION FEATURES FOR SURGICAL STAPLER

BACKGROUND

In some surgical procedures (e.g., colorectal, bariatric, thoracic, etc.), portions of a patient's digestive tract (e.g., the gastrointestinal tract and/or esophagus, etc.) may be cut and removed to eliminate undesirable tissue or for other reasons. Once the tissue is removed, the remaining portions of the digestive tract may be coupled together in an end-to-end anastomosis. The end-to-end anastomosis may provide a substantially unobstructed flow path from one portion of the digestive tract to the other portion of the digestive tract, without also providing any kind of leaking at the site of the anastomosis.

One example of an instrument that may be used to provide an end-to-end anastomosis is a circular stapler. Some such staplers are operable to clamp down on layers of tissue, cut through the clamped layers of tissue, and drive staples through the clamped layers of tissue to substantially seal the layers of tissue together near the severed ends of the tissue layers, thereby joining the two severed ends of the anatomical lumen together. The circular stapler may be configured to sever the tissue and seal the tissue substantially simultaneously. For instance, the circular stapler may sever excess tissue that is interior to an annular array of staples at an anastomosis, to provide a substantially smooth transition between the anatomical lumen sections that are joined at the anastomosis. Circular staplers may be used in open procedures or in endoscopic procedures. In some instances, a portion of the circular stapler is inserted through a patient's naturally occurring orifice.

Examples of circular staplers are described in U.S. Pat. No. 5,205,459, entitled "Surgical Anastomosis Stapling Instrument," issued Apr. 27, 1993; U.S. Pat. No. 5,271,544, entitled "Surgical Anastomosis Stapling Instrument," issued Dec. 21, 1993; U.S. Pat. No. 5,275,322, entitled "Surgical Anastomosis Stapling Instrument," issued Jan. 4, 1994; U.S. Pat. No. 5,285,945, entitled "Surgical Anastomosis Stapling Instrument," issued Feb. 15, 1994; U.S. Pat. No. 5,292,053, entitled "Surgical Anastomosis Stapling Instrument," issued Mar. 8, 1994; U.S. Pat. No. 5,333,773, entitled "Surgical Anastomosis Stapling Instrument," issued Aug. 2, 1994; U.S. Pat. No. 5,350,104, entitled "Surgical Anastomosis Stapling Instrument," issued Sep. 27, 1994; and U.S. Pat. No. 5,533,661, entitled "Surgical Anastomosis Stapling Instrument," issued Jul. 9, 1996; and U.S. Pat. No. 8,910,847, entitled "Low Cost Anvil Assembly for a Circular Stapler," issued Dec. 16, 2014. The disclosure of each of the above-cited U.S. Patents is incorporated by reference herein.

Some circular staplers may include a motorized actuation mechanism. Examples of circular staplers with motorized actuation mechanisms are described in U.S. Pub. No. 2015/0083772, entitled "Surgical Stapler with Rotary Cam Drive and Return," published Mar. 26, 2015, now abandoned; U.S. Pub. No. 2015/0083773, entitled "Surgical Stapling Instrument with Drive Assembly Having Toggle Features," published Mar. 26, 2015, issued as U.S. Pat. No. 9,936,949 on Apr. 10, 2018; U.S. Pub. No. 2015/0083774, entitled "Control Features for Motorized Surgical Stapling Instrument," published Mar. 26, 2015, issued as U.S. Pat. No. 9,907,552 on Mar. 6, 2018; and U.S. Pub. No. 2015/0083775, entitled "Surgical Stapler with Rotary Cam Drive," published Mar. 26, 2015, issued as U.S. Pat. No. 9,713,469 on Jul. 25, 2017. The disclosure of each of the above-cited U.S. Patent Publications is incorporated by reference herein.

While various kinds of surgical stapling instruments and associated components have been made and used, it is believed that no one prior to the inventor(s) has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 21E depicts a cross-sectional side view of the first and second sections of the digestive tract of FIG. 21A joined together at an end-to-end anastomosis;

Figure 1:
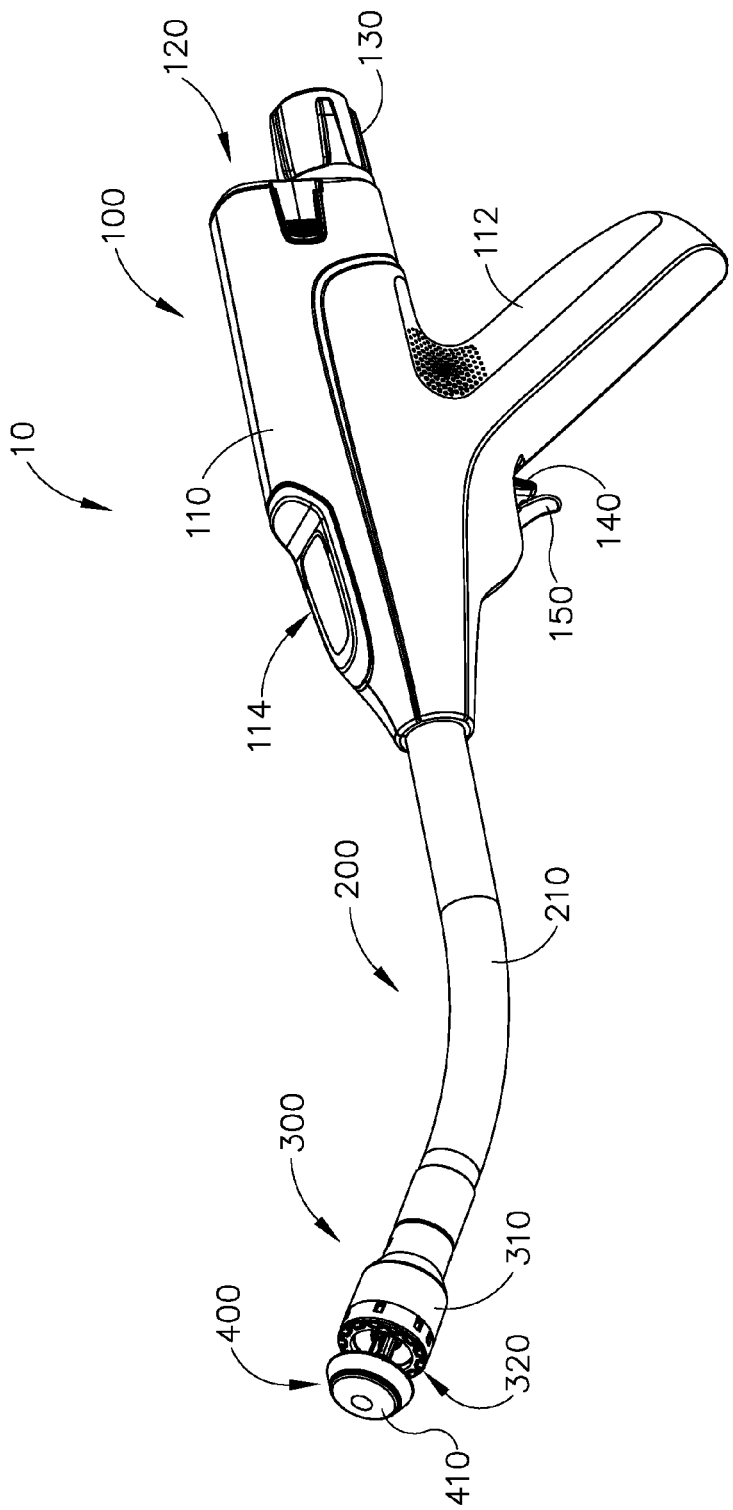
FIG. 1 depicts a perspective view of an exemplary circular stapler.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. Overview of Exemplary Circular Stapling Surgical Instrument

Figure 2:
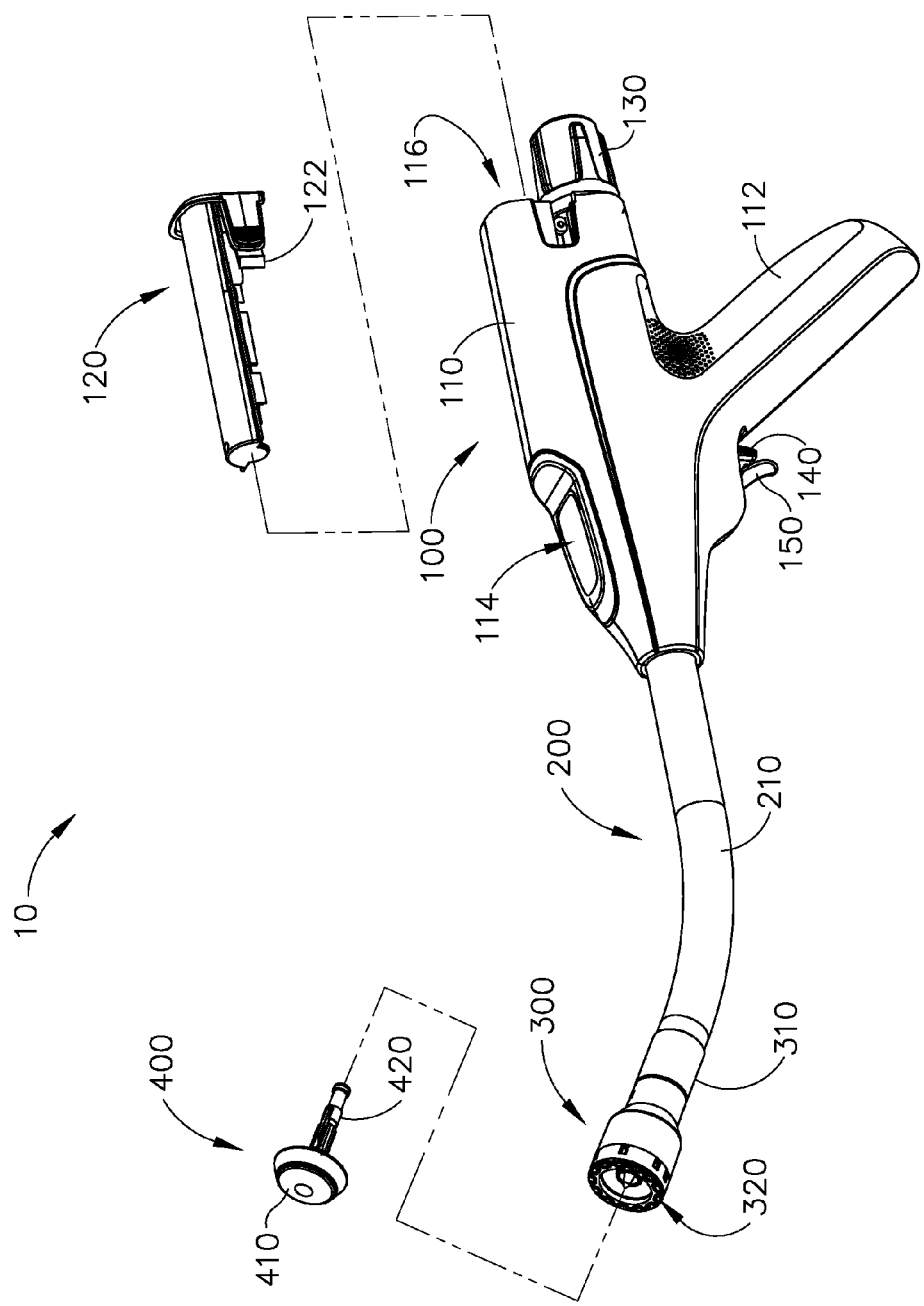
FIG. 2 depicts a perspective view of the circular stapler of FIG. 1, with a battery pack removed from a handle assembly and an anvil removed from a stapling head assembly.

FIGS. 1-2 depict an exemplary surgical circular stapling instrument (10) that may be used to provide an end-to-end anastomosis between two sections of an anatomical lumen such as a portion of a patient's digestive tract. Instrument (10) of this example comprises a handle assembly (100), a shaft assembly (200), a stapling head assembly (300), and an anvil (400). Handle assembly (100) comprises a casing (110)

defining an obliquely oriented pistol grip (112). In some versions, pistol grip (112) is perpendicularly oriented. In some other versions, pistol grip (112) is omitted. Handle assembly (110) further includes a window (114) that permits viewing of a movable indicator needle (526) as will be described in greater detail below. In some versions, a series of hash marks, colored regions, and/or other fixed indicators are positioned adjacent to window (114) in order to provide a visual context for indicator needle (526), thereby facilitating operator evaluation of the position of needle (526) within window (114). Various suitable alternative features and configurations for handle assembly (112) will be apparent to those of ordinary skill in the art in view of the teachings herein.

Instrument (10) of the present example further includes a battery pack (120). Battery pack (120) is operable to provide electrical power to a motor (160) in pistol grip (112) as will be described in greater detail below. Battery pack (120) is removable from handle assembly (100). In particular, as shown in FIGS. 1-2, battery pack (120) may be inserted into a socket (116) defined by casing (110). Once battery pack (120) is fully inserted in socket (116), latches (122) of battery pack (120) may resiliently engage interior features of casing (110) to provide a snap fit. To remove battery pack (120), the operator may press latches (122) inwardly to disengage latches (122) from the interior features of casing (110) then pull battery pack (120) proximally from socket (116). It should be understood that battery pack (120) and handle assembly (100) may have complementary electrical contacts, pins and sockets, and/or other features that provide paths for electrical communication from battery pack (120) to electrically powered components in handle assembly (100) when battery pack (120) is inserted in socket (116). It should also be understood that, in some versions, battery pack (120) is unitarily incorporated within handle assembly (100) such that battery back (120) cannot be removed from handle assembly (100).

Shaft assembly (200) extends distally from handle assembly (100) and includes a preformed bend. In some versions, the preformed bend is configured to facilitate positioning of stapling head assembly (300) within a patient's colon. Various suitable bend angles or radii that may be used will be apparent to those of ordinary skill in the art in view of the teachings herein. In some other versions, shaft assembly (200) is straight, such that shaft assembly (200) lacks a preformed bend. Various exemplary components that may be incorporated into shaft assembly (100) will be described in greater detail below.

Stapling head assembly (300) is located at the distal end of shaft assembly (200). As shown in FIGS. 1-2 and as will be described in greater detail below, anvil (400) is configured to removably couple with shaft assembly (200), adjacent to stapling head assembly (300). As will also be described in greater detail below, anvil (400) and stapling head assembly (300) are configured to cooperate to manipulate tissue in three ways, including clamping the tissue, cutting the tissue, and stapling the tissue. A knob (130) at the proximal end of handle assembly (100) is rotatable relative to casing (110) to provide precise clamping of the tissue between anvil (400) and stapling head assembly (300). When a safety trigger (140) of handle assembly (100) is pivoted away from a firing trigger (150) of handle assembly (100), firing trigger (150) may be actuated to thereby provide cutting and stapling of the tissue.

A. Exemplary Anvil

In the following discussion of anvil (400), the terms "distal" and "proximal" (and variations thereof) will be used with reference to the orientation of anvil (400) when anvil (400) is coupled with shaft assembly (200) of instrument (10). Thus, proximal features of anvil (400) will be closer to the operator of instrument (10); while distal features of anvil (400) will be further from the operator of instrument (10).

Figure 3:
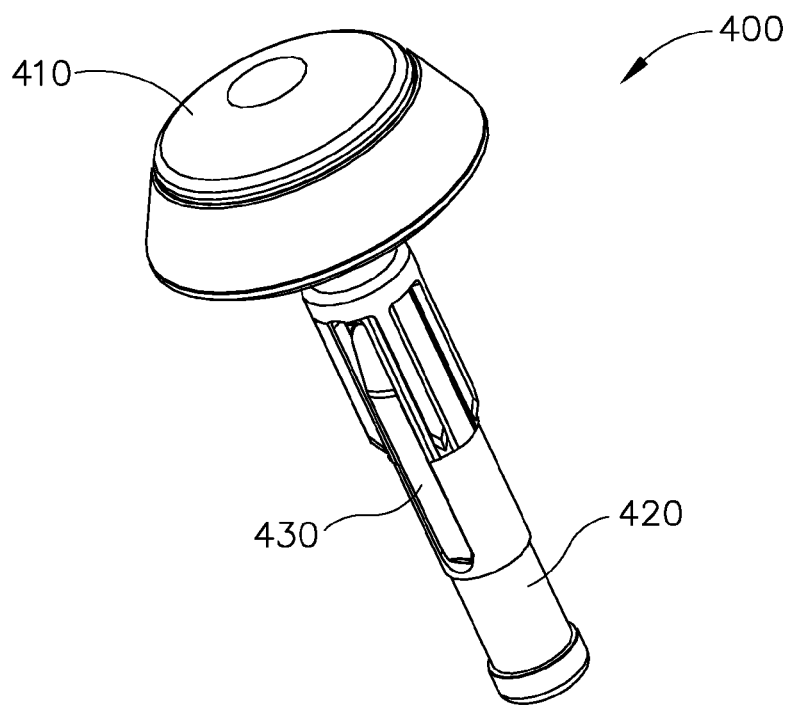
FIG. 3 depicts a perspective view of the anvil of the circular stapler of FIG. 1.
Figure 4:
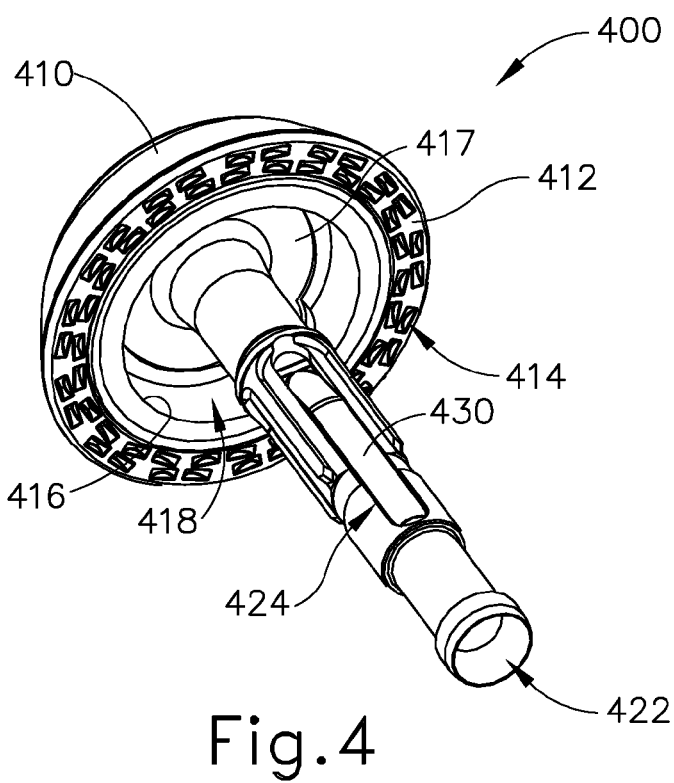
FIG. 4 depicts another perspective view of the anvil of FIG. 3.
Figure 5:
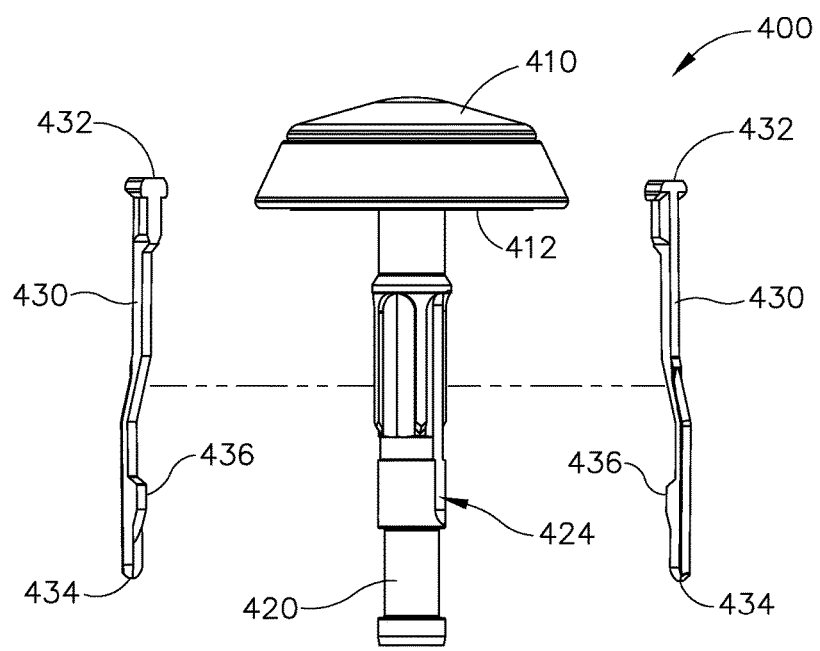
FIG. 5 depicts an exploded side elevational view of the anvil of FIG. 3.

As best seen in FIGS. 3-5, anvil (400) of the present example comprises a head (410) and a shank (420). Head (410) includes a proximal surface (412) that defines a plurality of staple forming pockets (414). Staple forming pockets (414) are arranged in two concentric annular arrays. In some other versions, staple forming pockets (414) are arranged in three or more concentric annular arrays. Staple forming pockets (414) are configured to deform staples as the staples are driven into staple forming pockets (414). For instance, each staple forming pocket (414) may deform a generally "U" shaped staple into a "B" shape as is known in the art. As best seen in FIG. 4, proximal surface (412) terminates at an inner edge (416), which defines an outer boundary of an annular recess (418) surrounding shank (420).

Shank (420) defines a bore or lumen (422) and includes a pair of pivoting latch members (430) positioned in bore (422). As best seen in FIG. 5, each latch member (430) includes a "T" shaped distal end (432), a rounded proximal end (434), and a latch shelf (436) located distal to proximal end (434). "T" shaped distal ends (432) secure latch members (430) within bore (422). Latch members (430) are positioned within bore (422) such that distal ends (434) are positioned at the proximal ends of lateral openings (424), which are formed through the sidewall of shank (420). Lateral openings (424) thus provide clearance for distal ends (434) and latch shelves (436) to deflect radially outwardly from the longitudinal axis defined by shank (420). However, latch members (430) are configured to resiliently bias distal ends (434) and latch shelves (436) to radially inwardly toward the longitudinal axis defined by shank (420). Latch members (430) thus act as retaining clips. This allows anvil (400) to be removably secured to a trocar (330) of stapling head assembly (300) as will be described in greater detail below. It should be understood, however, that latch members (436) are merely optional. Anvil (400) may be removably secured to a trocar (330) using any other suitable components, features, or techniques.

In addition to or in lieu of the foregoing, anvil (400) may be further constructed and operable in accordance with at least some of the teachings of U.S. Pat. No. 5,205,459; U.S. Pat. No. 5,271,544; U.S. Pat. No. 5,275,322; U.S. Pat. No. 5,285,945; U.S. Pat. No. 5,292,053; U.S. Pat. No. 5,333,773; U.S. Pat. No. 5,350,104; U.S. Pat. No. 5,533,661; and/or U.S. Pat. No. 8,910,847, the disclosures of which are incorporated by reference herein. Still other suitable configurations will be apparent to one of ordinary skill in the art in view of the teachings herein.

B. Exemplary Stapling Head Assembly

Figure 6:
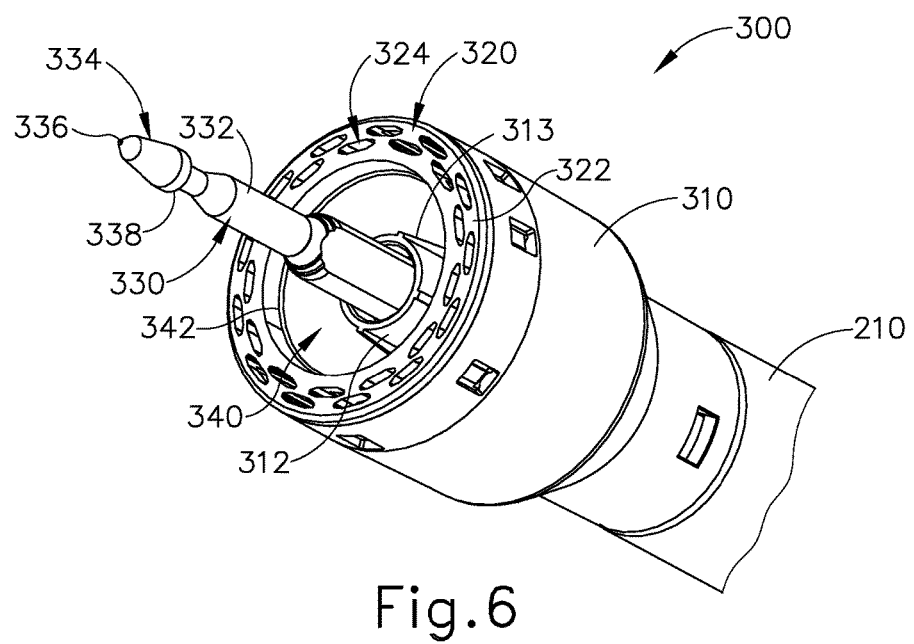
FIG. 6 depicts a perspective view of the stapling head assembly of the circular stapler of FIG. 1.
Figure 7:
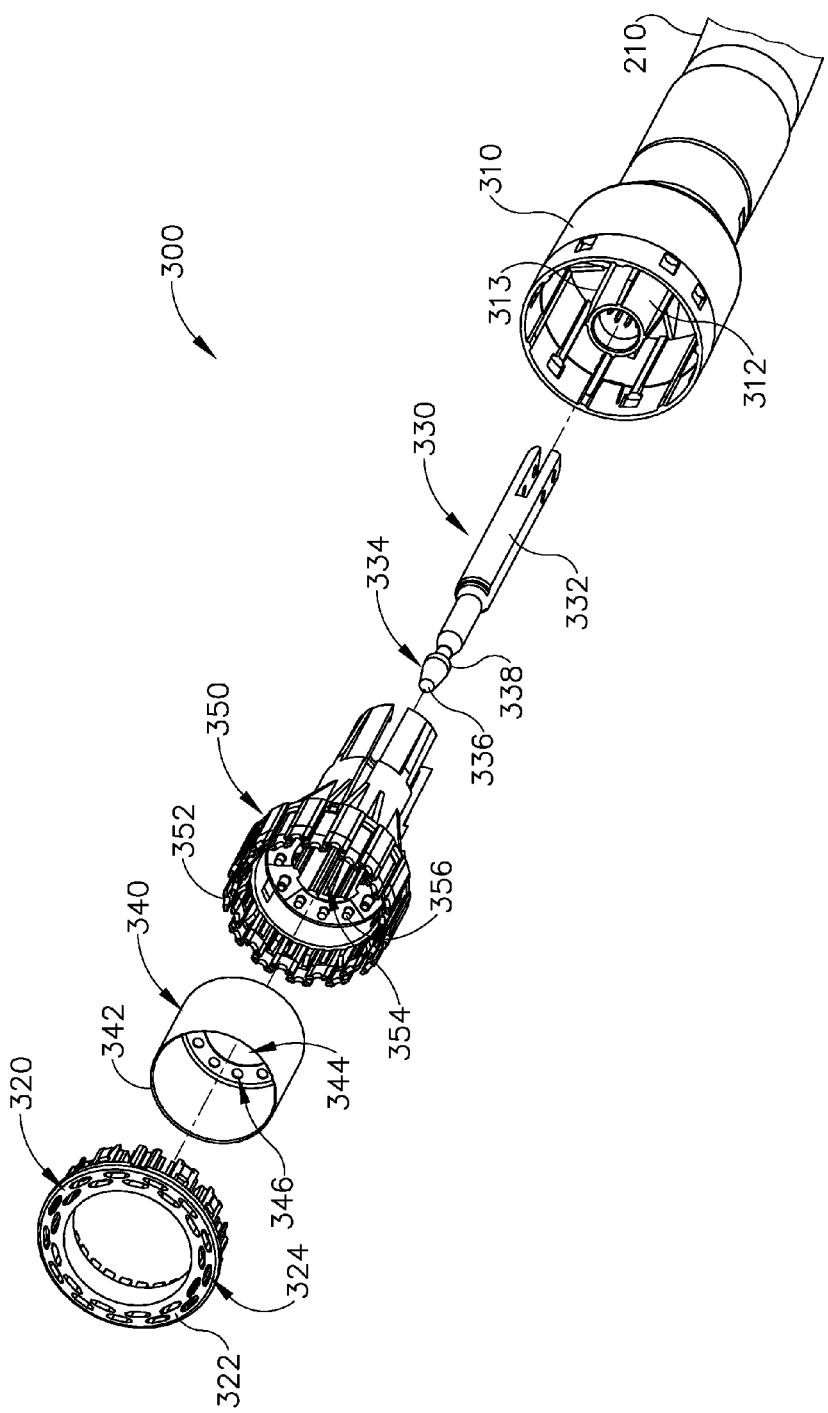
FIG. 7 depicts an exploded perspective view of the stapling head assembly of FIG. 6.

As best seen in FIGS. 6-7, stapling head assembly (300) of the present example is coupled to a distal end of shaft assembly (200) and comprises a tubular casing (310) housing a slidable staple driver member (350). A cylindraceous inner core member (312) extends distally within tubular casing (310). Tubular casing (310) is fixedly secured to an outer sheath (210) of shaft assembly (200), such that tubular casing (310) serves as a mechanical ground for stapling head assembly (300).

Trocar (330) is positioned coaxially within inner core member (312) of tubular casing (310). As will be described in greater detail below, trocar (330) is operable to translate distally and proximally relative to tubular casing (310) in response to rotation of knob (130) relative to casing (110) of handle assembly (100). Trocar (330) comprises a shaft (332) and a head (334). Head (334) includes a pointed tip (336) and an inwardly extending proximal surface (338). Shaft (332) thus provides a reduced outer diameter just proximal to head (334), with surface (338) providing a transition between that reduced outer diameter of shaft (332) and the outer diameter of head (334). While tip (336) is pointed in the present example, tip (336) is not sharp. Tip (336) will thus not easily cause trauma to tissue due to inadvertent contact with tissue. Head (334) and the distal portion of shaft (332) are configured for insertion in bore (422) of anvil (420). Proximal surface (338) and latch shelves (436) have complementary positions and configurations such that latch shelves (436) engage proximal surface (338) when shank (420) of anvil (400) is fully seated on trocar (330). Anvil (400) is thus secured to trocar (330) through a snap fit due to latch members (430).

Staple driver member (350) is operable to actuate longitudinally within tubular casing (310) in response to activation of motor (160) as will be described in greater detail below. Staple driver member (350) includes two distally presented concentric annular arrays of staple drivers (352). Staple drivers (352) are arranged to correspond with the arrangement of staple forming pockets (414) described above. Thus, each staple driver (352) is configured to drive a corresponding staple into a corresponding staple forming pocket (414) when stapling head assembly (300) is actuated. It should be understood that the arrangement of staple drivers (352) may be modified just like the arrangement of staple forming pockets (414) as described above. Staple driver member (350) also defines a bore (354) that is configured to coaxially receive core member (312) of tubular casing (310). An annular array of studs (356) project distally from a distally presented surface surrounding bore (354).

A cylindraceous knife member (340) is coaxially positioned within staple driver member (350). Knife member (340) includes a distally presented, sharp circular cutting edge (342). Knife member (340) is sized such that knife member (340) defines an outer diameter that is smaller than the diameter defined by the inner annular array of staple drivers (352). Knife member (340) also defines an opening that is configured to coaxially receive core member (312) of tubular casing (310). An annular array of openings (346) formed in knife member (340) is configured to complement the annular array of studs (356) of staple driver member (350), such that knife member (340) is fixedly secured to staple driver member (350) via studs (356) and openings (346). Other suitable structural relationships between knife member (340) and stapler driver member (350) will be apparent to those of ordinary skill in the art in view of the teachings herein.

A deck member (320) is fixedly secured to tubular casing (310). Deck member (320) includes a distally presented deck surface (322) defining two concentric annular arrays of staple openings (324). Staple openings (324) are arranged to correspond with the arrangement of staple drivers (352) and staple forming pockets (414) described above. Thus, each staple opening (324) is configured to provide a path for a corresponding staple driver (352) to drive a corresponding staple through deck member (320) and into a corresponding staple forming pocket (414) when stapling head assembly (300) is actuated. It should be understood that the arrangement of staple openings (322) may be modified just like the arrangement of staple forming pockets (414) as described above. It should also be understood that various structures and techniques may be used to contain staples within stapling head assembly (300) before stapling head assembly (300) is actuated. Such structures and techniques that are used to contain staples within stapling head assembly (300) may prevent the staples from inadvertently falling out through staple openings (324) before stapling head assembly (300) is actuated. Various suitable forms that such structures and techniques may take will be apparent to those of ordinary skill in the art in view of the teachings herein.

As best seen in FIG. 6, deck member (320) defines an inner diameter that is just slightly larger than the outer diameter defined by knife member (340). Deck member (320) is thus configured to allow knife member (340) to translate distally to a point where cutting edge (342) is distal to deck surface (322).

In addition to or in lieu of the foregoing, stapling head assembly (300) may be further constructed and operable in accordance with at least some of the teachings of U.S. Pat. No. 5,205,459; U.S. Pat. No. 5,271,544; U.S. Pat. No. 5,275,322; U.S. Pat. No. 5,285,945; U.S. Pat. No. 5,292,053; U.S. Pat. No. 5,333,773; U.S. Pat. No. 5,350,104; U.S. Pat. No. 5,533,661; and/or U.S. Pat. No. 8,910,847, the disclosures of which are incorporated by reference herein. Still other suitable configurations will be apparent to one of ordinary skill in the art in view of the teachings herein.

C. Exemplary Shaft Assembly

Figure 8:
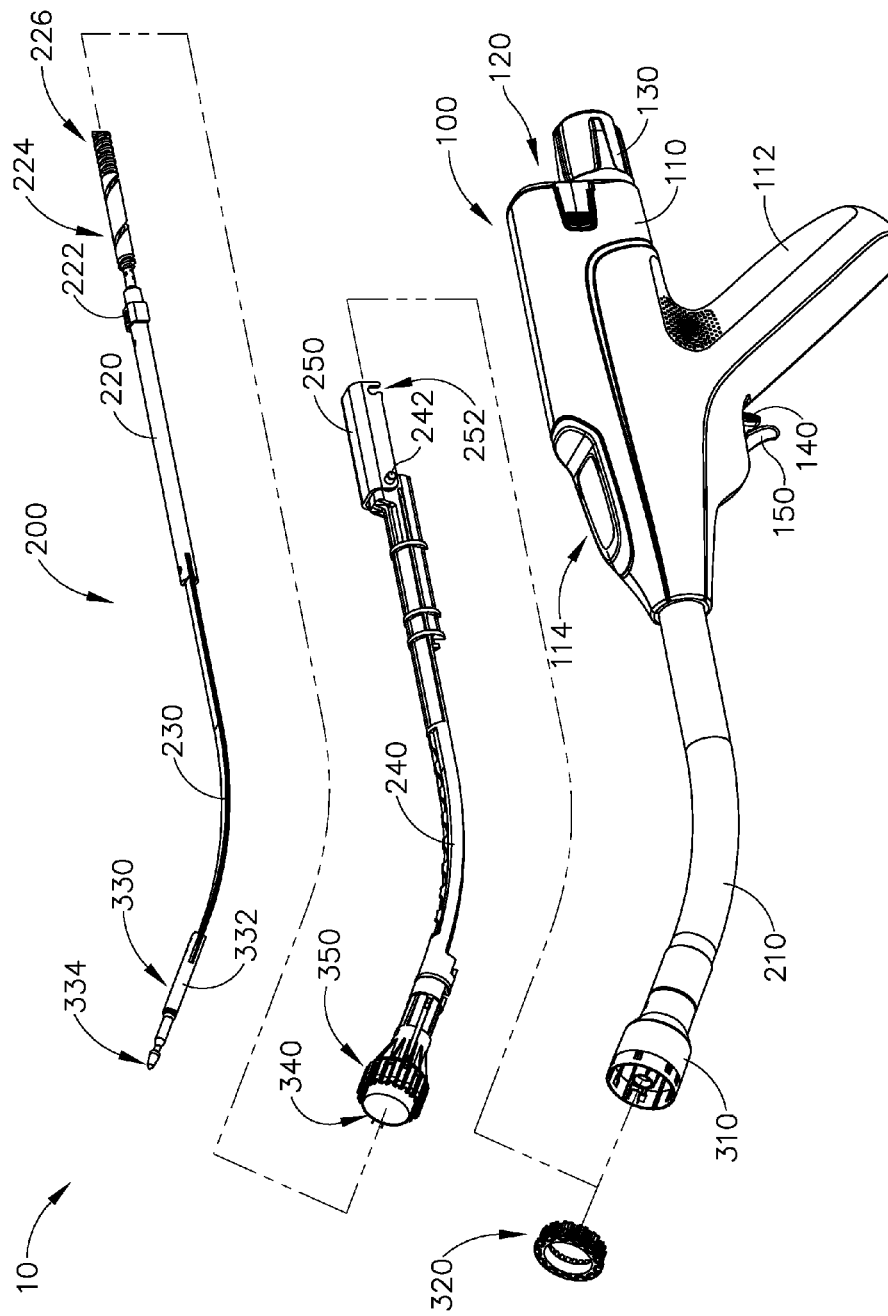
FIG. 8 depicts an exploded perspective view of the circular stapler of FIG. 1, with portions of the shaft assembly shown separately from each other.

FIG. 8 shows various components of shaft assembly (200), which couples components of stapling head assembly (300) with components of handle assembly (100). In particular, and as noted above, shaft assembly (200) includes an outer sheath (210) that extends between handle assembly (100) and tubular casing (310). In the present example, outer sheath (210) is rigid and includes a preformed curved section as noted above.

Shaft assembly (200) further includes a trocar actuation rod (220) and a trocar actuation band assembly (230). The distal end of trocar actuation band assembly (230) is fixedly secured to the proximal end of trocar shaft (332). The proximal end of trocar actuation band assembly (230) is fixedly secured to the distal end of trocar actuation rod (220). It should therefore be understood that trocar (330) will translate longitudinally relative to outer sheath (210) in response to translation of trocar actuation band assembly (230) and trocar actuation rod (220) relative to outer sheath (210). Trocar actuation band assembly (230) is configured to flex such that trocar actuation band assembly (230) may follow along the preformed curve in shaft assembly (200) as trocar actuation band assembly (230) is translated longitudinally relative to outer sheath (210). However, trocar actuation band assembly (230) has sufficient column strength and tensile strength to transfer distal and proximal forces from trocar actuation rod (220) to trocar shaft (332). Trocar actuation rod (220) is rigid. A clip (222) is fixedly secured to trocar actuation rod (220) and is configured to cooperate with complementary features within handle assembly (100) to prevent trocar actuation rod (220) from rotating within handle assembly (100) while still permitting trocar actuation rod (220) to translate longitudinally within handle assembly (100). Trocar actuation rod (220) further includes a coarse helical threading (224) and a fine helical threading (226). Details regarding the movement of trocar actuation rod (220) will be described in greater detail below.

Shaft assembly (200) further includes a stapling head assembly driver (240) that is slidably received within outer sheath (210). The distal end of stapling head assembly driver (240) is fixedly secured to the proximal end of staple driver member (350). The proximal end of stapling head assembly driver (240) is secured to a drive bracket (250) via a pin (242). It should therefore be understood that staple driver member (350) will translate longitudinally relative to outer sheath (210) in response to translation of stapling head assembly driver (240) and drive bracket (250) relative to outer sheath (210). Stapling head assembly driver (240) is configured to flex such that stapling head assembly driver (240) may follow along the preformed curve in shaft assembly (200) as stapling head assembly driver (240) is translated longitudinally relative to outer sheath (210). However, stapling head assembly driver (240) has sufficient column strength to transfer distal forces from drive bracket (250) to staple driver member (350). Details regarding the movement of drive bracket (250) will be described in greater detail below.

While not shown in FIG. 8, it should be understood that shaft assembly (200) may further include one or more spacer elements within outer sheath (210). Such spacer elements may be configured to support trocar actuation band assembly (230) and/or stapling head assembly driver (240) as trocar actuation band assembly (230) and/or stapling head assembly driver (240) translate through outer sheath (210). For instance, such spacer elements may prevent trocar actuation band assembly (230) and/or stapling head assembly driver (240) from buckling as trocar actuation band assembly (230) and/or stapling head assembly driver (240) translate through outer sheath (210). Various suitable forms that such spacer elements may take will be apparent to those of ordinary skill in the art in view of the teachings herein.

In addition to or in lieu of the foregoing, shaft assembly (200) may be further constructed and operable in accordance with at least some of the teachings of U.S. Pat. No. 5,205,459; U.S. Pat. No. 5,271,544; U.S. Pat. No. 5,275,322; U.S. Pat. No. 5,285,945; U.S. Pat. No. 5,292,053; U.S. Pat. No. 5,333,773; U.S. Pat. No. 5,350,104; U.S. Pat. No. 5,533,661; and/or U.S. Pat. No. 8,910,847, the disclosures of which are incorporated by reference herein. Still other suitable configurations will be apparent to one of ordinary skill in the art in view of the teachings herein.

D. Exemplary Actuator Handle Assembly

Figure 9:
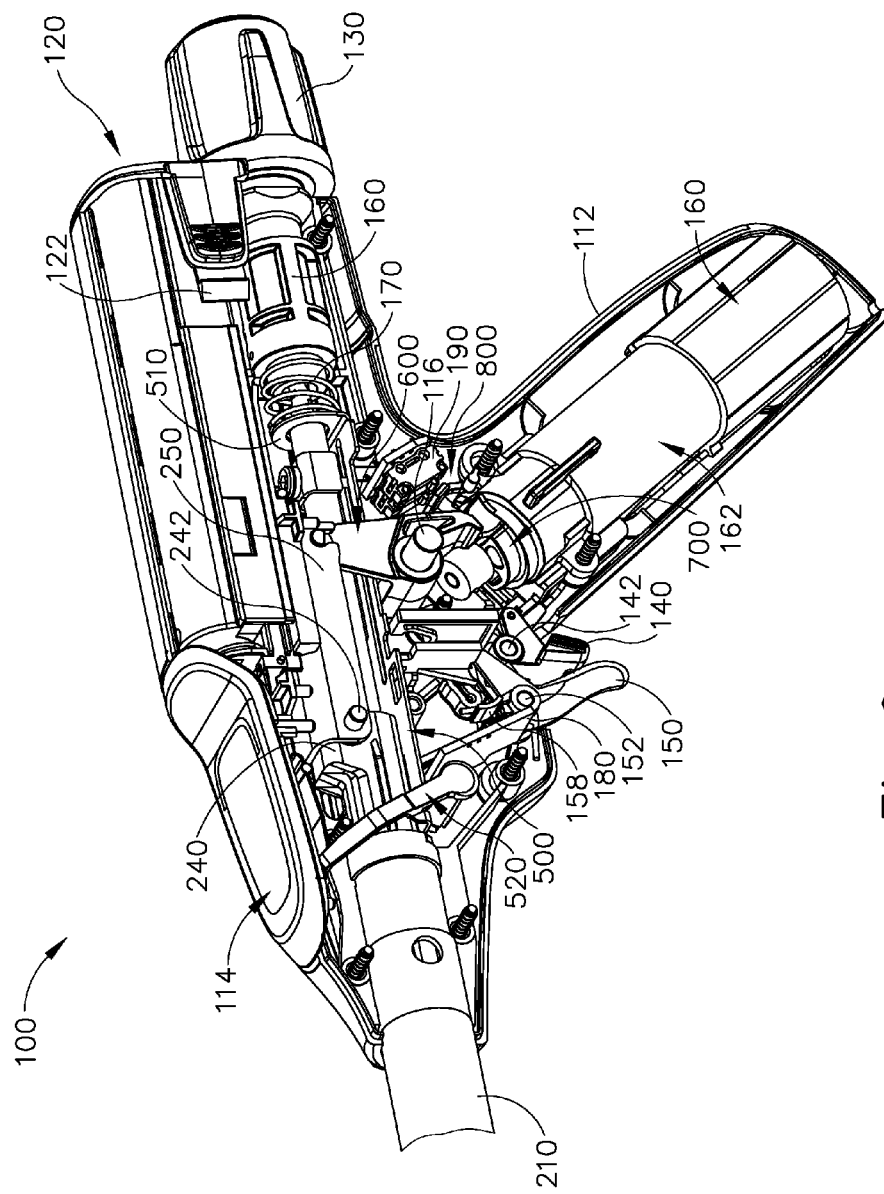
FIG. 9 depicts a perspective view of the handle assembly of the circular stapler of FIG. 1, with a housing half omitted to reveal internal components of the handle assembly.

As shown in FIG. 9, handle assembly (100) includes several components that are operable to actuate anvil (400) and stapling head assembly (300). Handle assembly (100) also includes components that are operable to selectively lock out triggers (140, 150) based on the position of anvil (400) relative to stapling head assembly (300). When triggers (140, 150) are locked out, firing trigger (150) is prevented from initiating actuation of stapling head assembly (300). Thus, trigger (150) is only operable to initiate actuation of stapling head assembly (300) when the position of anvil (400) relative to stapling head assembly (300) is within a predefined range. The components of handle assembly (100) that provide the foregoing operability will be described in greater detail below.

1. Exemplary Anvil Actuation Assembly

Knob (130) protrudes proximally from casing (110) of handle assembly and is rotatable relative to casing (110). As shown in FIG. 9, a nut (160) is secured to the distal end of knob (130). In the present example, nut (160) is fixedly secured to the distal end of knob (130) such that nut (160) will rotate unitarily with knob (130). Nut (160) and knob (130) are configured to cooperate with trocar actuation rod (220) to thereby translate trocar actuation rod (220) longitudinally relative to casing (110) in response to rotation of nut (160) and knob (130) relative to casing (110). As noted above, trocar (330) will translate longitudinally relative to outer sheath (210) in response to translation of trocar actuation rod (220) relative to outer sheath (210) and casing (110).

The proximal portion of trocar actuation rod (220) is positioned within handle assembly (100) to engage nut (160) and knob (130). In particular, trocar actuation rod (220) is positioned within handle assembly (100) such that coarse helical threading (224) will selectively engage a thread engagement feature (not shown) within the interior of nut (160); and such that fine helical threading (226) will selectively engage a thread engagement feature (not shown) within the interior of knob (130). In some versions, the thread engagement feature of nut (160) comprises an inwardly directed tab; while the thread engagement feature of knob (130) comprises a helical threading. Other suitable forms that such thread engagement features may take will be apparent to those of ordinary skill in the art in view of the teachings herein.

In the present example, when nut (160) and knob (130) are rotated relative to casing (110), trocar actuation rod (220) travels proximally through a first range of longitudinal motion where coarse helical threading (224) is engaged with nut (160) to provide a relatively rapid rate of translation. Fine helical threading (226) is not engaged with knob (130) during this range of motion. When nut (160) and knob (130) are further rotated relative to casing (110) after trocar actuation rod (220) completes the first range of motion, trocar actuation rod (220) will continue to travel proximally through a second range of longitudinal motion where fine helical threading (226) is engaged with knob (130) to provide a relatively slow rate of translation. Thus, trocar actuation rod (220) will translate proximally through a sequence of rapid translation followed by slow translation, based on engagement between coarse helical threading (224) and nut (160) followed by engagement between fine helical threading (226) and knob (130).

It should be understood that when anvil (400) is coupled with trocar (330), rotation of knob (130) will provide corresponding translation of anvil relative to stapling head assembly (300). It should also be understood that knob (130) may be rotated in a first angular direction (e.g., clockwise) to retract anvil (400) toward stapling head assembly (300); and in a second angular direction (e.g., counterclockwise) to advance anvil (500) away from stapling head assembly (300). Knob (130) may thus be used to adjust the gap distance (d) between opposing surfaces (412, 322) of anvil (400) and stapling head assembly (300) until a suitable gap distance (d) has been achieved as shown in FIG. 21C and as described in greater detail below.

2. Exemplary Trigger Lockout Assembly

As noted above, knob may be used to adjust the gap distance (d) between opposing surfaces (412, 322) of anvil (400) and stapling head assembly (300). Setting an appropriate gap distance (d) before actuating stapling head assembly (300) may be critical to the success of an anastomosis. For instance, if the gap distance (d) is too great, the staples that are deployed at the anastomosis site may not be sufficiently formed by staple forming pockets (414). This may result in leakage at the anastomosis site, and in some cases may ultimately lead to the separation of the anatomical lumen sections that are joined at the anastomosis site. If the gap distance (d) is too small, the internal structure of the tissue compressed between surfaces (412, 322) may be damaged to the point where the structural integrity of the tissue is compromised. This may prevent the tissue from adequately holding the formed staples, which again may result in leakage or other failure of the anastomosis. It may therefore be desirable to provide the operator with some form of feedback indicating whether the gap distance (d) is within an appropriate range. It may also be desirable to prevent the operator from actuating stapling head assembly (300) unless the gap distance (d) is within an appropriate range.

Figure 10:
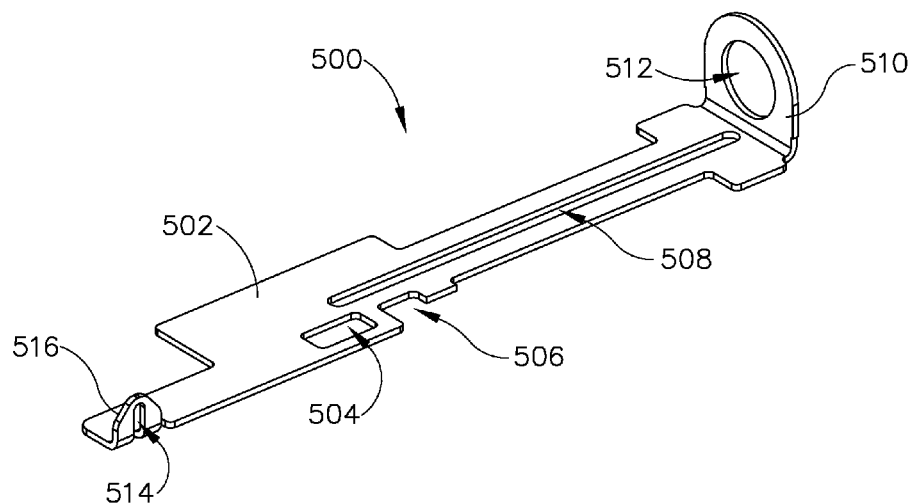
FIG. 10 depicts a perspective view of a bracket of the handle assembly of FIG. 9.

FIGS. 9-12E show components that provide feedback to the operator to indicate whether the gap distance (d) is within an appropriate range; and prevent the operator from actuating stapling head assembly (300) unless the gap distance (d) is within an appropriate range. As best seen in FIGS. 12B-12C, a bracket (500) is configured and positioned to move in response to movement of trocar actuation rod (220). As best seen in FIG. 10, bracket (500) includes a rigid body (502) that defines a first slot (504), a second slot (506), and a third slot (508). An upright feature (510) is positioned at the proximal end of body (502) and defines an opening (512). Trocar actuation rod (220) extends coaxially through opening (512). As shown in FIG. 9, a coil spring (170) is interposed between the proximal end of upright feature (510) and a rigid bulkhead feature that is defined by casing (110) and that forms a support journal for nut (160). The bulkhead is fixed within casing (110) and thereby provides a ground for the proximal end of coil spring (170), such that coil spring (170) resiliently imparts a distal bias to bracket (500) via upright feature (510). Bracket (500) further includes a laterally presented flange (516) at the distal end of body (502). Flange (516) defines a slot (514).

Figure 11:
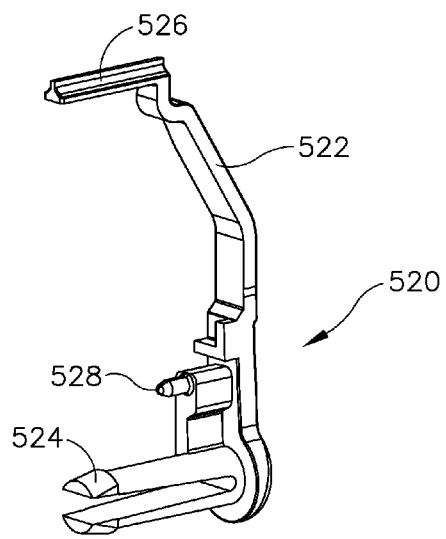
FIG. 11 depicts a perspective view of an indicator member of the handle assembly of FIG. 9.
Figure 12A:
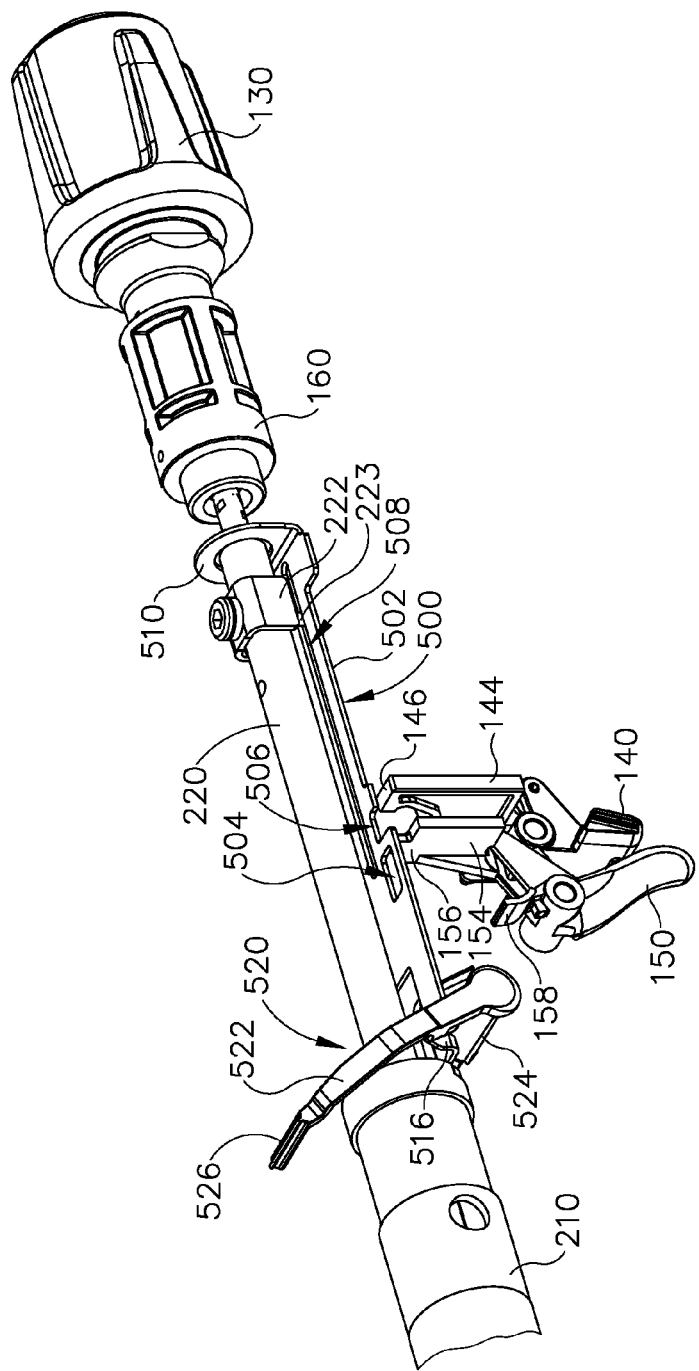
FIG. 12A depicts a perspective view of an anvil actuation assembly of the circular stapler of FIG. 1, an actuation rod in a first position.
Figure 12B:
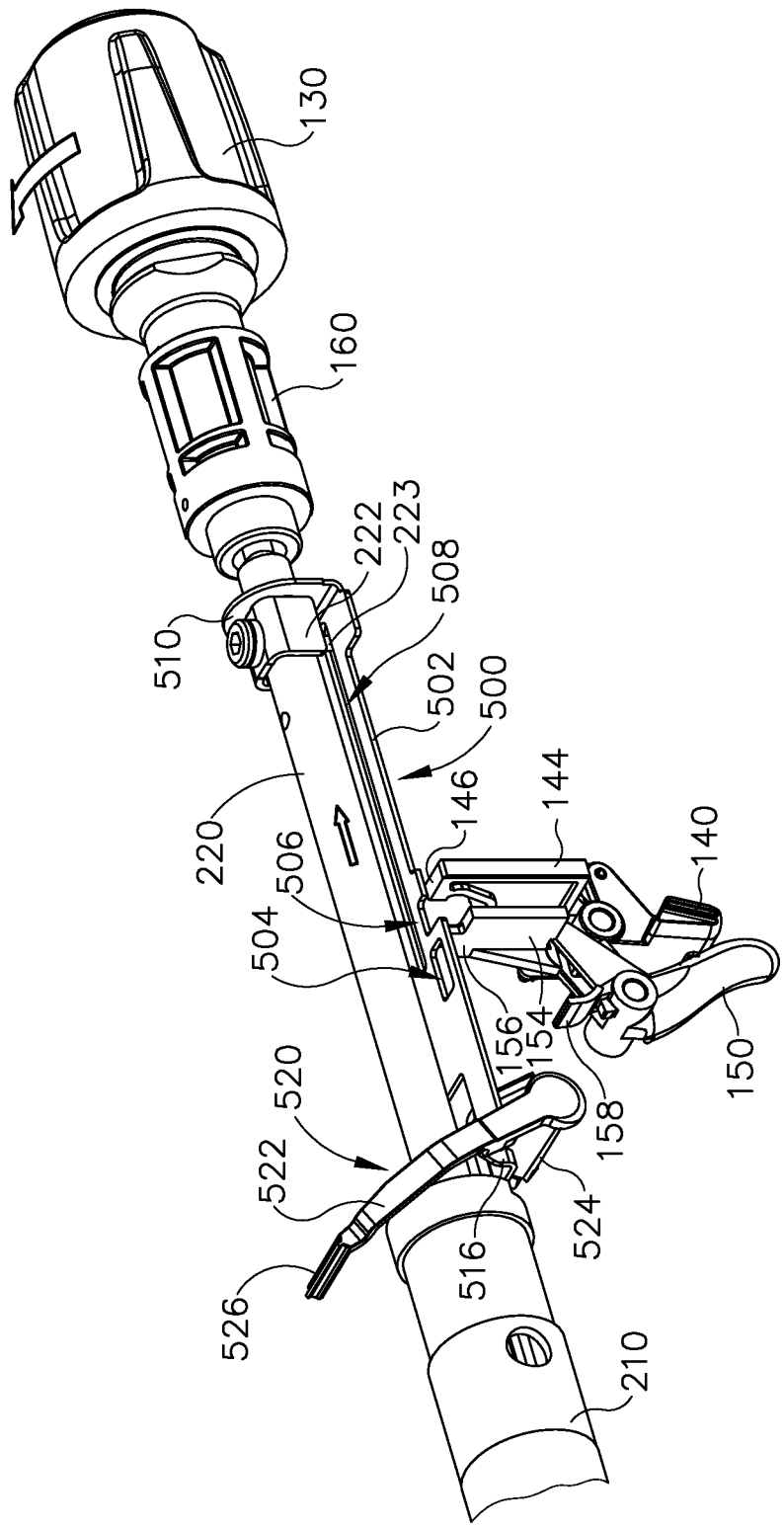
FIG. 12B depicts a perspective view of the anvil actuation assembly of FIG. 12A, with the actuation rod moved to a second position to engage the bracket of FIG. 10.
Figure 12C:
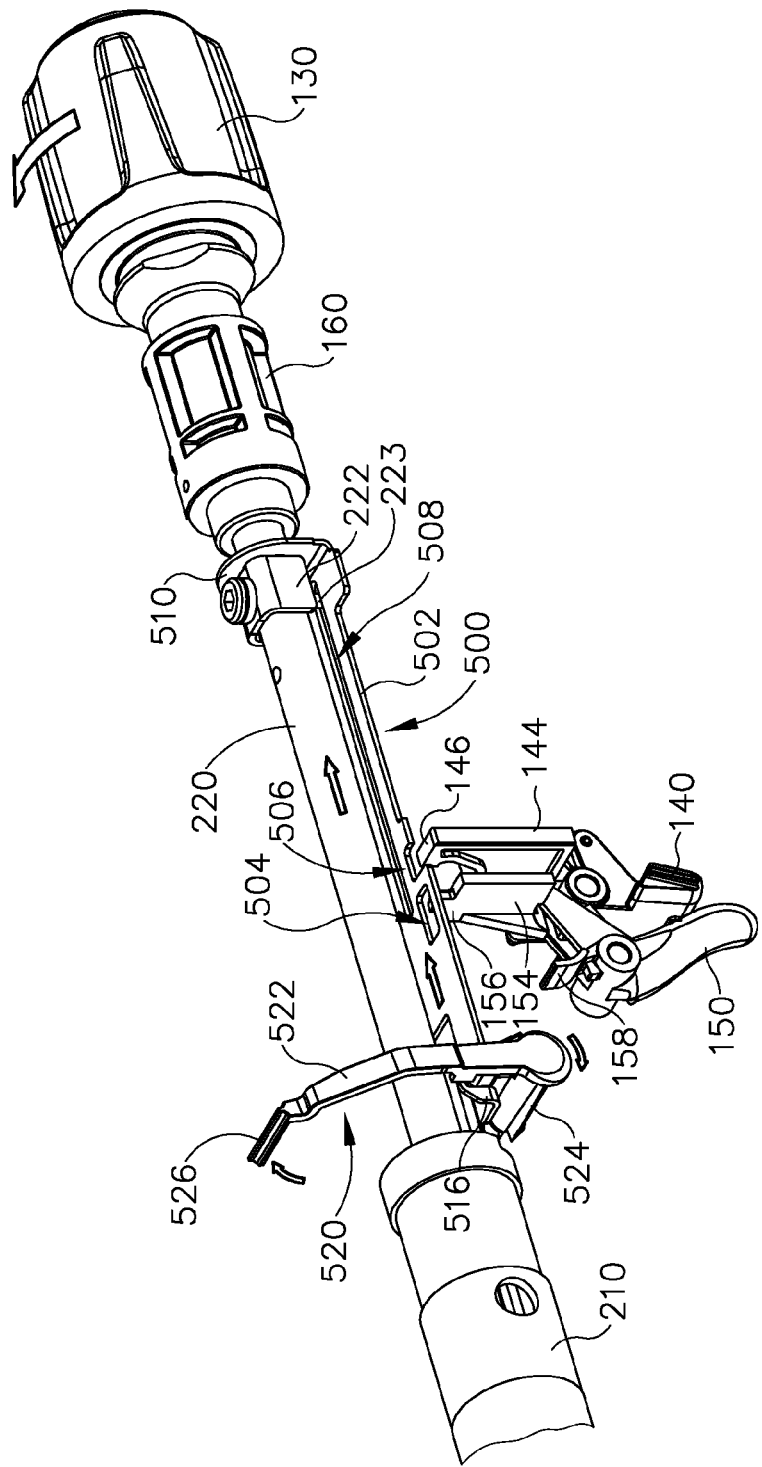
FIG. 12C depicts a perspective view of the anvil actuation assembly of FIG. 12A, with the actuation rod moved to a third position to retract the bracket of FIG. 10 proximally.

As best seen in FIGS. 12B-12C, an indicator member (520) is configured to pivot in response to translation of bracket (500). As best seen in FIG. 11, indicator member (520) comprises an upright arm (522), a snap pin (524) projecting laterally from a lower end of arm (522), an indicator needle (526) projecting laterally from an upper end of arm (522), and a coupling pin (528) projecting laterally from an intermediate region of arm (522). Snap pin (524) is configured to snap into a complementary recess provided by casing (110). Snap pin (524) thereby secures indicator member (520) to casing (110) yet permits indicator member (520) to pivot relative to casing (110) about the longitudinal axis of snap pin (524). Indicator needle (526) is positioned to be visible through window (114) of handle assembly (110) to thereby visually indicate the pivotal position of indicator member (520). Coupling pin (528) is slidably received in slot (514) of flange (516) of bracket (500). This engagement between indicator member (520), casing (110), and bracket (500) provides pivotal movement of indicator member (520) in response to translation of bracket (500).

Bracket (500) is configured to selectively prevent and permit actuation of triggers (140, 150). In particular, slots (504, 506) of bracket (500) are configured to selectively provide clearance for actuation of triggers (140, 150). As shown in FIGS. 12A-12E, safety trigger (140) is pivotably coupled with a first upright member (144). First upright member (144) is coupled with casing (110) such that first upright member (144) is configured to translate upwardly in response to pivoting of safety trigger (140) toward pistol grip (112). However, body (502) of bracket (500) is configured to prevent this movement of first upright member (144) and safety trigger (140) by engaging the upper end (146) of first upright member (144). Body (502) thus blocks movement of first upright member (144) and safety trigger (140) until bracket (500) is moved to a position where slot (506) is aligned with upper end (146) to thereby provide clearance for upward movement of first upright member (144). It should therefore be understood that safety trigger (140) cannot be pivoted toward pistol grip (112) until slot (506) is positioned over upper end (146).

Similarly, firing trigger (150) is pivotably coupled with a second upright member (154). Second upright member (154) is coupled with casing (110) such that second upright member (154) is configured to translate upwardly in response to pivoting of safety trigger (150) toward pistol grip (112). However, body (502) of bracket (500) is configured to prevent this movement of second upright member (154) and firing trigger (150) by engaging the upper end (156) of second upright member (154). Even if safety trigger (140) is pivoted out of the way to otherwise permit movement of firing trigger (150), body (502) blocks movement of second upright member (154) and firing trigger (150) until bracket (500) is moved to a position where slot (504) is aligned with upper end (156) to thereby provide clearance for upward movement of second upright member (154). It should therefore be understood that, even if safety trigger (140) is pivoted out of the way to otherwise permit movement of firing trigger (150), firing trigger (150) cannot be pivoted toward pistol grip (112) until slot (504) is positioned over upper end (156).

Third slot (508) is configured to receive a downwardly projecting boss (223) of clip (222), which is rigidly secured to trocar actuation rod (220). While casing (110) is configured to allow bracket (500) to translate longitudinally within casing (110), casing (110) includes rails, channels, and/or other features that prevent bracket (500) from rotating within casing (110). Thus, the positioning of boss (223) in slot (508) prevents clip (222) and trocar actuation rod (220) from rotating within casing (110). Boss (223) and slot (508) nevertheless allow bracket (500) to translate longitudinally within casing (110) as will be described in greater detail below.

FIGS. 12A-12E depict the above-described components at various stages of operation. In particular, in FIG. 12A, trocar actuation rod (220) is in a distal-most position, such that trocar (330) is in a distal-most position. At this stage, the operator may couple anvil (400) with trocar (330) by inserting trocar (330) into bore (422) until latch members (430) are secured to head (334) of trocar (330). The operator then rotates knob (130), which rotates nut (160). As knob (130) and nut (160) rotate, engagement between coarse helical threading (224) of trocar actuation rod (220) and the complementary feature of nut (160) causes trocar actuation rod (220) to retract proximally at a relatively rapid rate, such that trocar actuation rod (220) reaches the position shown in FIG. 12B. This provides proximal retraction of trocar actuation rod (220) provides retraction of trocar (330) and anvil (400). As trocar actuation rod (220) moves from the position shown in FIG. 12A to the position shown in FIG. 12B, bracket (500) remains stationary. This is due to the fact that clip (222) is spaced apart from upright feature (510) at the stage shown in FIG. 12A and does not engage upright feature (510) until trocar actuation rod (220) reaches the position shown in FIG. 12B.

After reaching the stage shown in FIG. 12B, the operator may continue rotating knob (130) and nut (160), which causes further proximal retraction of trocar actuation rod (220) as shown in FIG. 12C. This of course causes further proximal retraction of trocar (330) and anvil (400). As trocar actuation rod (220) moves from the position shown in FIG. 12B to the position shown in FIG. 12C, clip (222) bears against bracket (500), driving bracket (500) proximally. This proximal movement of bracket (500) causes indicator member (520) to pivot from the position shown in FIG. 12B to the position shown in FIG. 12C due to the positioning of pin (528) in slot (514) of flange (516).

As indicator member (520) pivots from the position shown in FIG. 12B to the position shown in FIG. 12C, the operator may observe the position of indicator needle (526) through window (114) of handle assembly (110). As noted above, a series of hash marks, colored regions, and/or other fixed indicators may be positioned adjacent to window (114) in order to provide a visual context for indicator needle (526), thereby facilitating operator evaluation of the position of needle (526) within window (114). It should be understood that the position of needle (526) within window (114) will be indicative of the longitudinal position of trocar (330) and anvil (400). The position of needle (526) within window (114) will thus indicate the gap distance (d) between opposing surfaces (412, 322) of anvil (400) and stapling head assembly (300). While observing the position of needle (526) within window (114), the operator may rotate knob (130) clockwise or counterclockwise to further retract or advance trocar (330) and anvil (400), thereby providing fine adjustment of the gap distance (d) until a desired gap distance (d) is reached within an appropriate range.

In order to provide fine control of the gap distance (d) adjustment at the stage shown in FIG. 12C, trocar actuation rod (220) will be at a longitudinal position where fine helical threading (226) is engaged with a complementary feature of knob (130) and coarse helical threading (224) is disengaged from the complementary feature of nut (160). In some versions, coarse helical threading (224) disengages nut (160) and fine helical threading (226) begins to engage knob (130) once trocar actuation rod (220) reaches the longitudinal position shown in FIG. 12B (i.e., when clip (222) first engages upright member (510)). In some other versions, the transition from engagement by coarse helical threading (224) to fine helical threading (226) occurs sometime between the stage shown in FIG. 12B and the stage shown in FIG. 12C. Other suitable stages at which the coarse-to-fine transition may occur will be apparent to those of ordinary skill in the art in view of the teachings herein. It should also be understood that some alternative versions of trocar actuation rod (220) may have just a single threading section, with the pitch of the threading being consistent along the length of the threading. In other words, trocar actuation rod (220) does not necessarily need to have two different sections of threading (224, 226) with different pitches.

At the stage shown in FIG. 12C, slot (506) is aligned with upper end (146) to thereby provide clearance for upward movement of first upright member (144). Similarly, slot (504) is aligned with upper end (156) to thereby provide clearance for upward movement of second upright member (154). In the present example, slots (504, 506) are sized and positioned such that slots (504, 506) only provide clearance for upward movement of upright members (144, 154) when the gap distance (d) is within a clinically acceptable range. By way of example only, a "clinically acceptable range" for the gap distance (d) may be between approximately 0.110 inches and approximately 0.040 inches. As another merely illustrative example, a "clinically acceptable range" for the gap distance (d) may be between approximately 0.110 inches and approximately 0.020 inches. Even when slots (504, 506) are positioned to provide clearance for upward movement of upright members (144, 154) as shown in FIG. 12C, safety trigger (140) will still block pivotal movement of firing trigger (150) about a pin (152) (FIG. 9) when safety trigger (140) is in the non-actuated position shown in FIG. 12C. Thus, in order to enable movement of firing trigger (150), the operator will need to first actuate safety trigger (140) about a pin (142) (FIG. 9) from the position shown in FIG. 12C to the position shown in FIG. 12D.

Figure 12D:
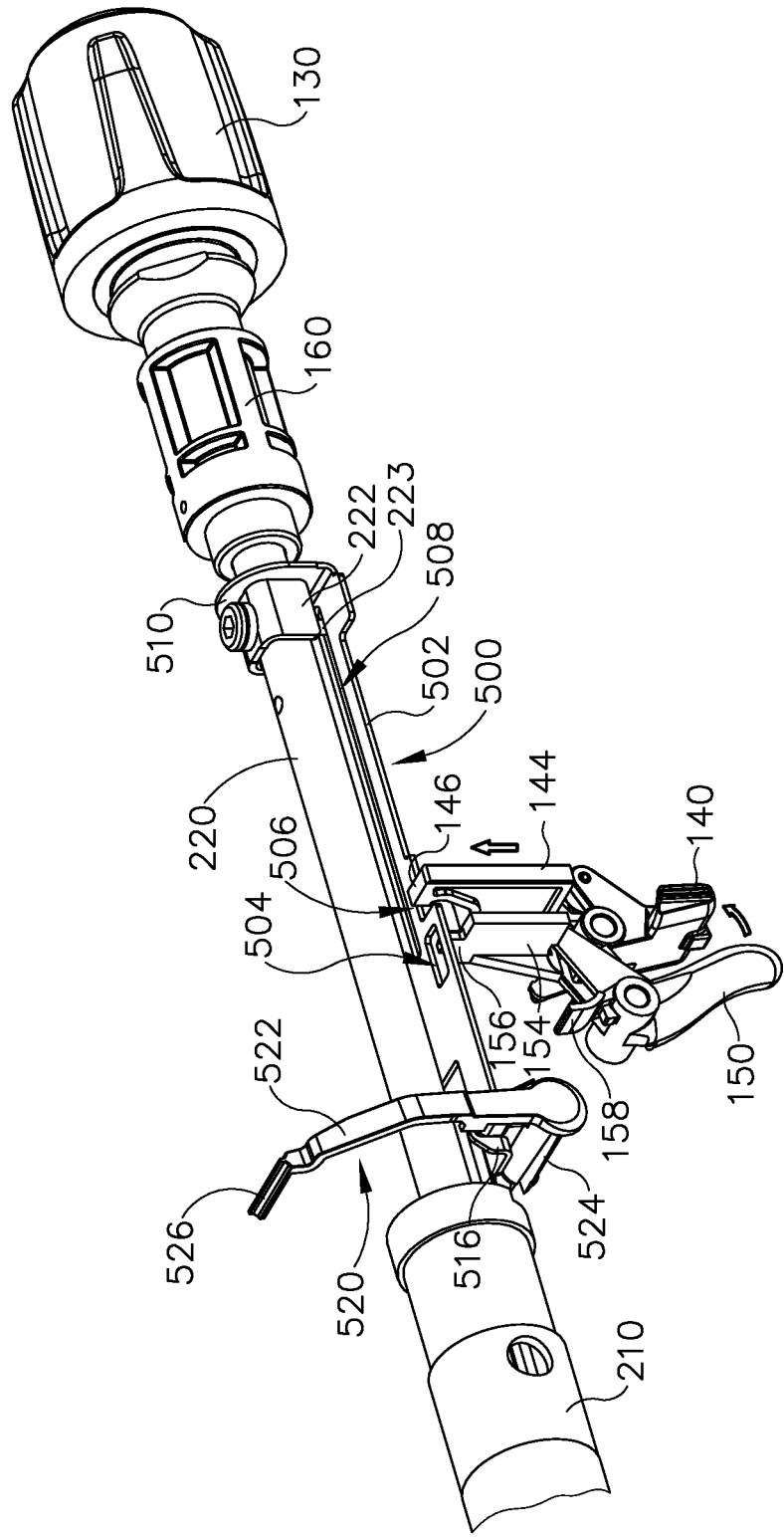
FIG. 12D depicts a perspective view of the anvil actuation assembly of FIG. 12A, with a safety trigger pivoted from a first position to a second position.

As shown in FIG. 12D, upper end (146) passes through slot (506) as safety trigger (140) is pivoted from the position shown in FIG. 12C to the position shown in FIG. 12D. It should be understood that this movement of upper end (146) would not be possible at the stages shown in FIGS. 12A-12B (when the gap distance (d) is too great) because body (502) would physically block upward movement of upright member (144), thereby physically blocking pivotal movement of safety trigger (140). In the present example, a cap (not shown) incorporated into knob (130) prevents knob (130) from rotating to a point where anvil (400) would be retracted too far proximally (such that the gap distance (d) is too small). In some other variations, even if knob (130) were to permit anvil (400) to be retracted too far proximally (such that the gap distance (d) is too small), body (502) would physically block upward movement of upright member (144), thereby physically blocking pivotal movement of safety trigger (140), in the event that the operator retracts trocar (330) and anvil (400) too far proximally (such that the gap distance (d) is too small). Regardless of whether body (502), knob (130), or some other feature prevents actuation when the gap distance (d) would be too small, it should be understood that instrument (10) permits actuation of safety trigger (140) only when the gap distance (d) is within the clinically acceptable range.

Figure 12E:
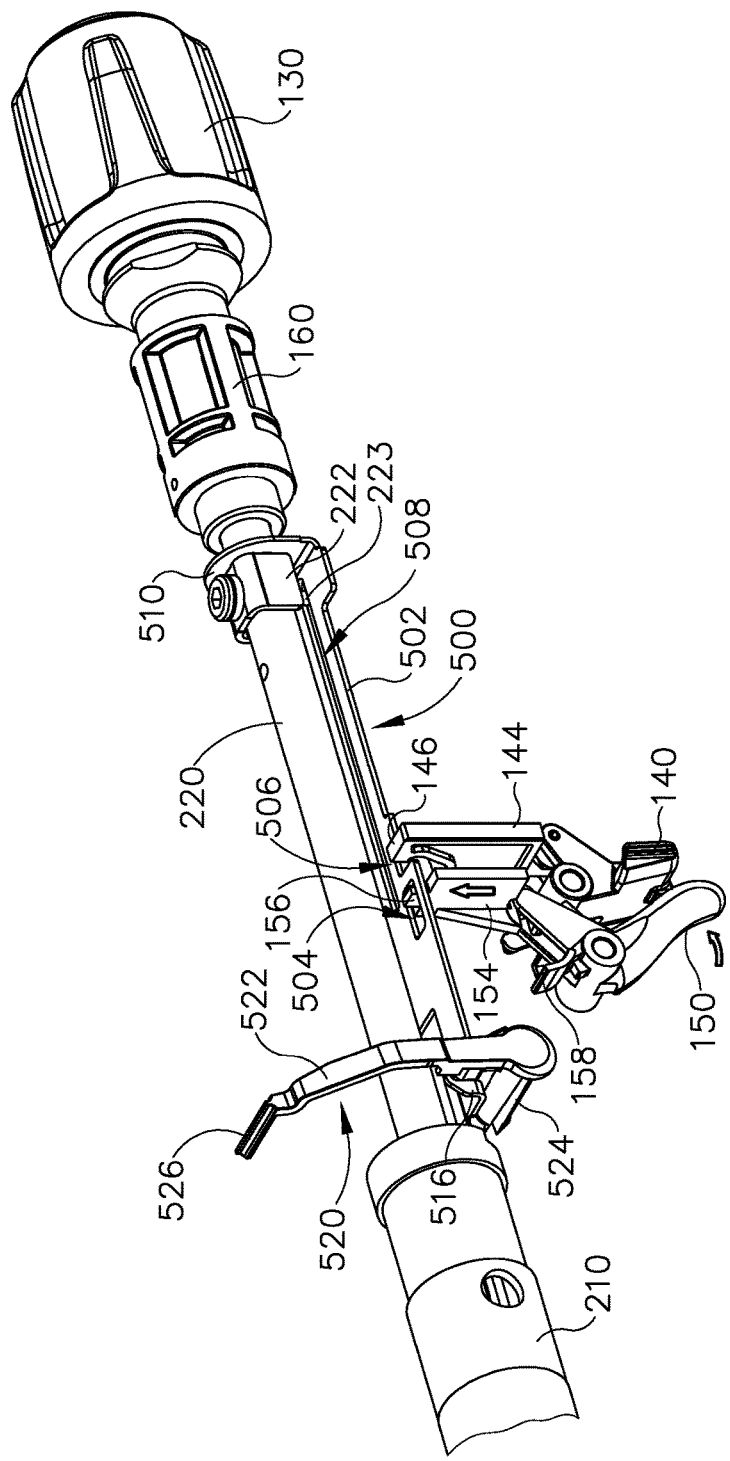
FIG. 12E depicts a perspective view of the anvil actuation assembly of FIG. 12A, with a firing trigger pivoted from a first position to a second position.
Figure 13:
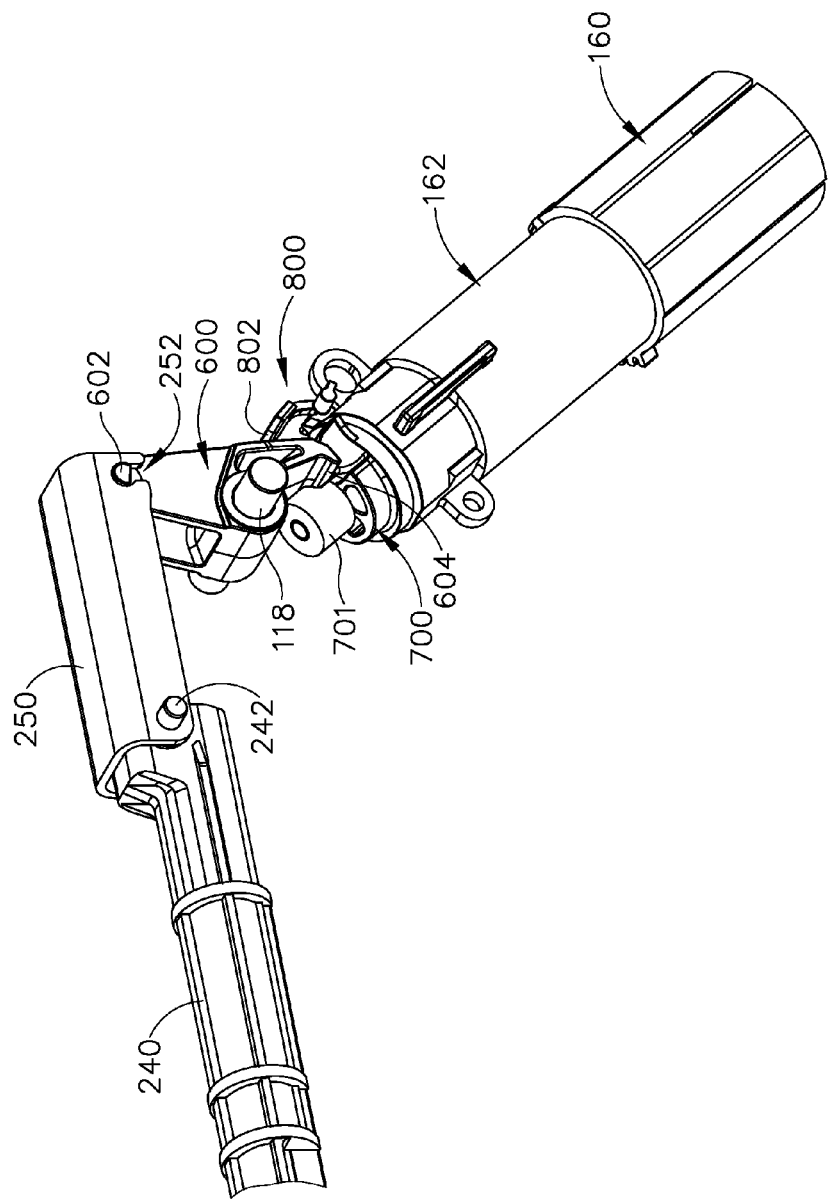
FIG. 13 depicts a perspective view of a stapling head actuation assembly of the circular stapler of FIG. 1.

As noted above, safety trigger (140) is configured to prevent actuation of firing trigger (150) until safety trigger (140) has been actuated. Once safety trigger (140) has been actuated, the operator may actuate firing trigger (150) from the position shown in FIG. 12D to the position shown in FIG. 12E. As shown in FIG. 12E, upper end (156) passes through slot (504) as firing trigger (150) is pivoted from the position shown in FIG. 12D to the position shown in FIG. 12E. It should be understood that, even in the complete absence of safety trigger (140), this movement of upper end (156) would not be possible at the stages shown in FIGS. 12A-12B (when the gap distance (d) is too great) because body (502) would physically block upward movement of upright member (154), thereby physically blocking pivotal movement of firing trigger (150). It should also be understood that body (502) would also physically block upward movement of upright member (154), thereby physically blocking pivotal movement of firing trigger (150), in the event that the operator retracts trocar (330) and anvil (400) too far proximally (such that the gap distance (d) is too small). Thus, even in the complete absence of safety trigger (140), firing trigger (150) may only be actuated when the gap distance (d) is within the clinically acceptable range.

Firing trigger (150) of the present example includes an integral actuation paddle (158). Paddle (158) pivots forwardly as firing trigger (150) pivots from the position shown in FIG. 12D to the position shown in FIG. 12E. Paddle (158) is configured to actuate a switch of a motor activation module (180), which is shown in FIG. 9, when firing trigger (150) pivots from the position shown in FIG. 12D to the position shown in FIG. 12E. Motor activation module (180) is in communication with battery pack (120) and motor (160), such that motor activation module (180) is configured to provide activation of motor (160) with electrical power from battery pack (120) in response to paddle (158) actuating the switch of motor activation module (180). Thus, motor (160) will be activated when firing trigger (150) is pivoted from the position shown in FIG. 12D to the position shown in FIG. 12E. This activation of motor (160) will actuate stapling head assembly (300) as described in greater detail below.

3. Exemplary Stapling Head Actuation Assembly

FIGS. 13-20D show various components that are operable to actuate stapling head assembly (300). These components include motor (160), a gearbox (162), a rotary cam member (700), a cam follower (600), drive bracket (250) and stapling head assembly driver (240). Gearbox (162) is coupled with a drive shaft of motor (160) and is further coupled with cam member (700). Activation of motor (160) thus causes rotation of cam member (700) via gearbox (162). Various suitable configurations that may be used for gearbox (162) will be apparent to those of ordinary skill in the art in view of the teachings herein. Cam member (700) is configured to interact with cam follower (160) to pivot cam follower (160) in two angular directions about a pin (118) as will be described in greater detail below. Pin (118) is coupled with casing (110). A bushing (701) provides rotary support to cam member (700) relative to casing (110).

Figure 14:
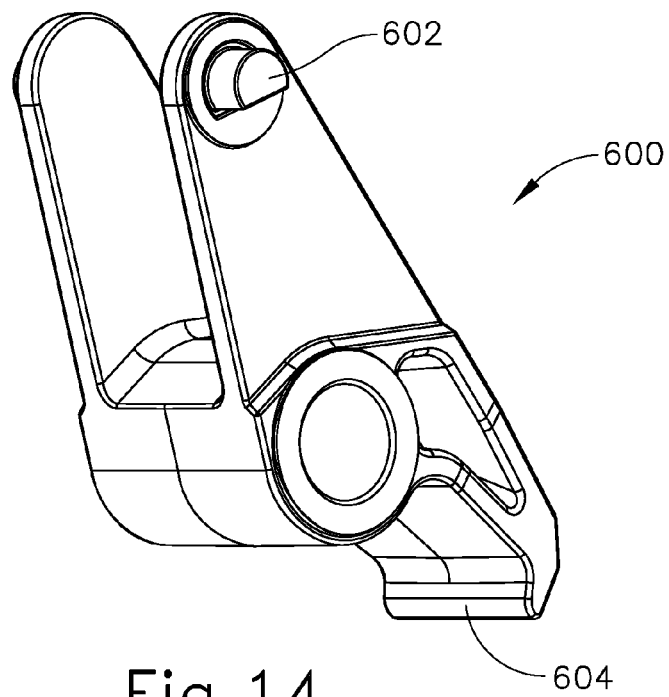
FIG. 14 depicts a perspective view of a cam follower of the stapling head actuation assembly of FIG. 13.
Figure 15:
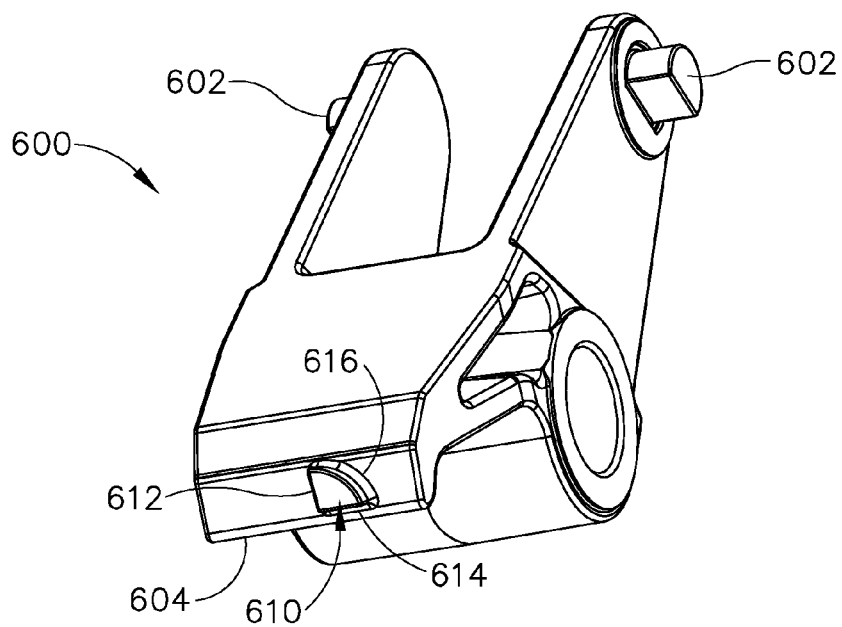
FIG. 15 depicts another perspective view of the cam follower of FIG. 14.

Cam follower (600) is pivotably coupled with drive bracket (250) via a pair of integral pins (602), which are received in complementary notches (252) of drive bracket (250). As shown in FIGS. 14-15, cam follower (600) includes a first bearing feature (604) and a second bearing feature (610). First bearing feature (604) consists of a rounded, horizontally extending surface. Second bearing feature (610) is shaped like a quarter-pie defined by a straight vertical surface (612), a horizontally extending surface (614), and a curved surface (616). Second bearing feature (610) projects proximally relative to first bearing feature (504).

Figure 16:
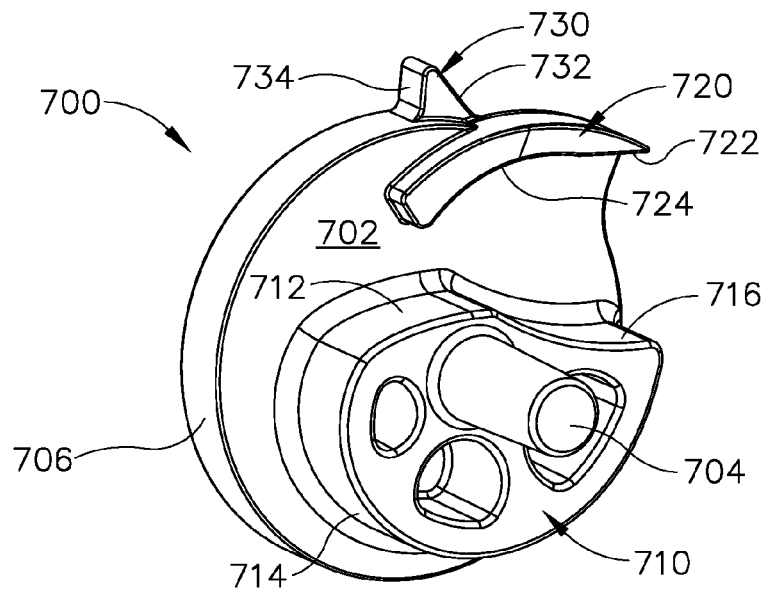
FIG. 16 depicts a perspective view of a rotary cam of the stapling head actuation assembly of FIG. 13.
Figure 17:
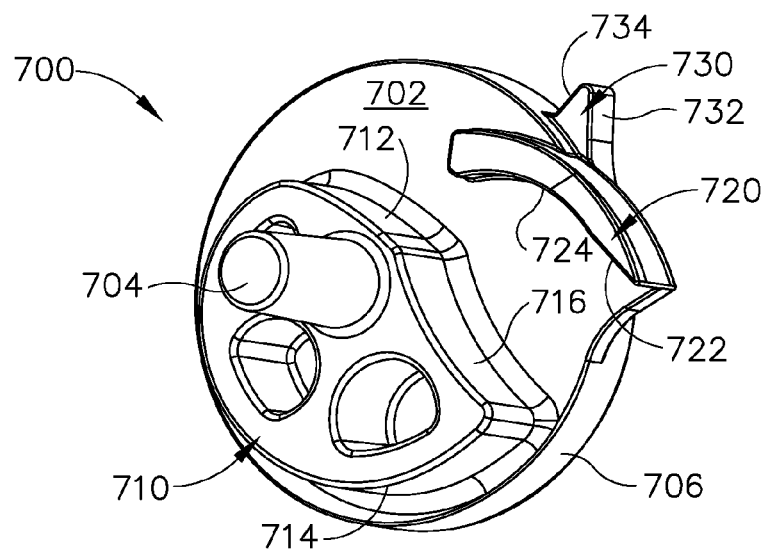
FIG. 17 depicts another perspective view of the rotary cam of FIG. 16.

FIGS. 16-17 show cam member (700) in greater detail. Cam member (700) comprises a distal face (702), a distally projecting post (704), and an outer circumferential surface (706). A first cam feature (710) and a second cam feature (720) project distally from distal face (702). Post (704) engages bushing (701). First cam feature (710) comprises a first surface region (712), a second surface region (714), and a third surface region (716). First surface region (712) is convexly defined by a relatively large radius of curvature, such that first surface region (712) is nearly flat. Second surface region (714) is convexly defined by a progressively increasing radius of curvature. Third surface region (716) is concavely defined by a relatively large radius of curvature. In addition to projecting distally from distal face (702), second cam feature (720) projects outwardly from outer circumferential surface (706). Second cam feature (720) includes a first surface region (722) and a second surface region (724). First surface region (722) is substantially flat while second surface region (724) is concavely curved. The origin of the radius of curvature for each curved surface region (712, 714, 716, 724) is offset from the center of post (704).

Figure 18A:
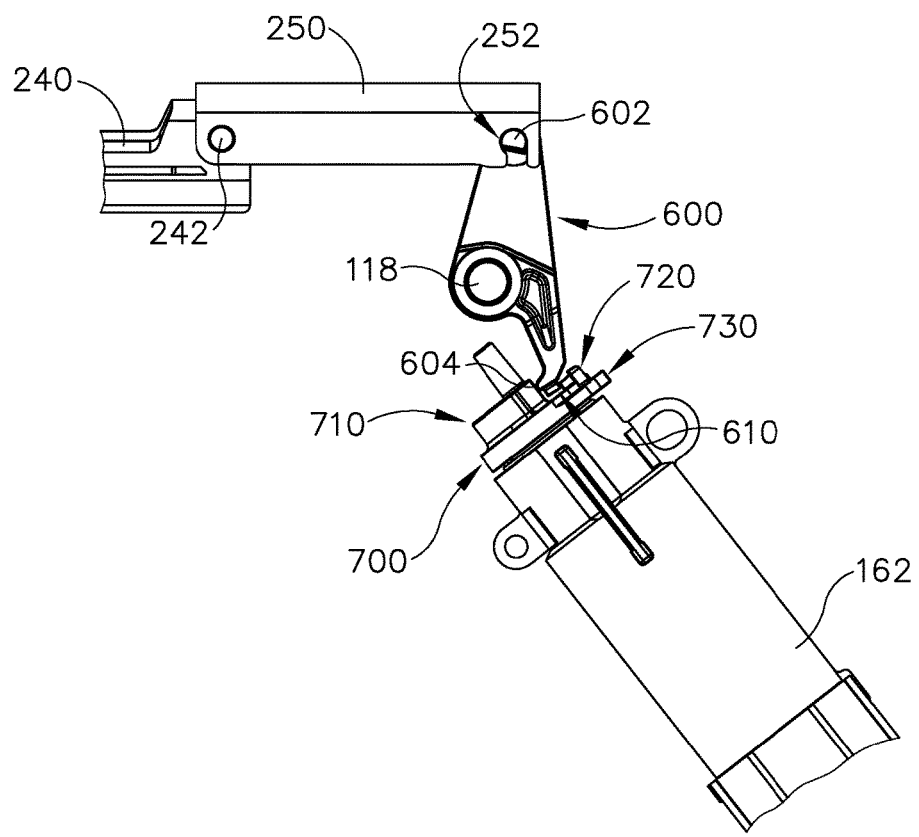
FIG. 18A depicts a side elevational view of the stapling head actuation assembly of FIG. 13, with the rotary cam in a first angular position and the cam follower in a first pivotal position.
Figure 18B:
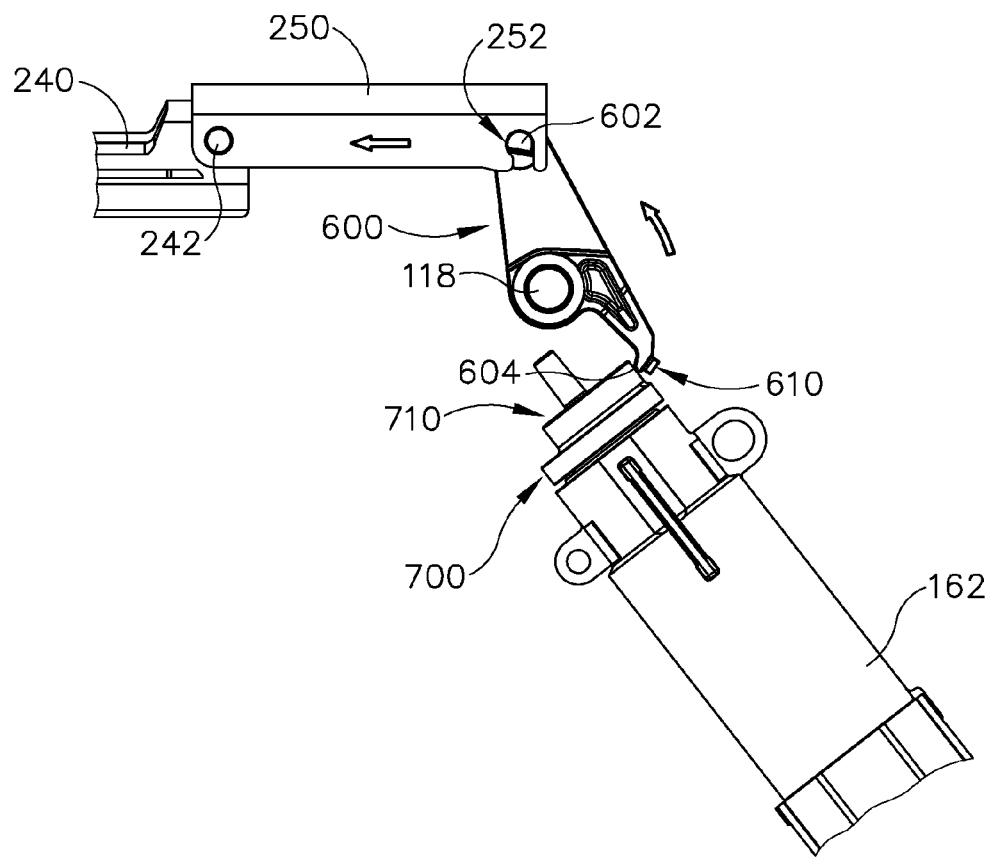
FIG. 18B depicts a side elevational view of the stapling head actuation assembly of FIG. 13, with the rotary cam in a second angular position and the cam follower in a second pivotal position.

FIGS. 18A-18B show the general interaction between cam follower (600) and first and second cam features (710, 720), though this interaction will be described in greater detail below with reference to FIGS. 20A-20D. As cam member (700) is rotated from the position shown in FIG. 18A to the position shown in FIG. 18B, first cam feature (710) bears against first bearing feature (604) of cam follower (600), causing cam follower to pivot about pin (118). In the view shown in FIGS. 18A-18B, cam follower (600) pivots counterclockwise as cam member (700) is rotated from the position shown in FIG. 18A to the position shown in FIG. 18B. As can be seen in the transition from FIG. 18A to FIG. 18B, this counterclockwise pivoting of cam follower (600) drives drive bracket (250) and stapling head assembly driver (240) distally, thereby actuating stapling head assembly (300). As cam member (700) continues to rotate in the same direction back toward the position shown in FIG. 18A, second cam feature (720) engages and bears against second bearing feature (610) of cam follower (600), causing cam follower (600) to pivot clockwise about pin (118). This clockwise pivoting of cam follower (600) about pin (118) retracts drive bracket (250) and stapling head assembly driver (240) proximally back toward the position shown in FIG. 18A.

Figure 19A:
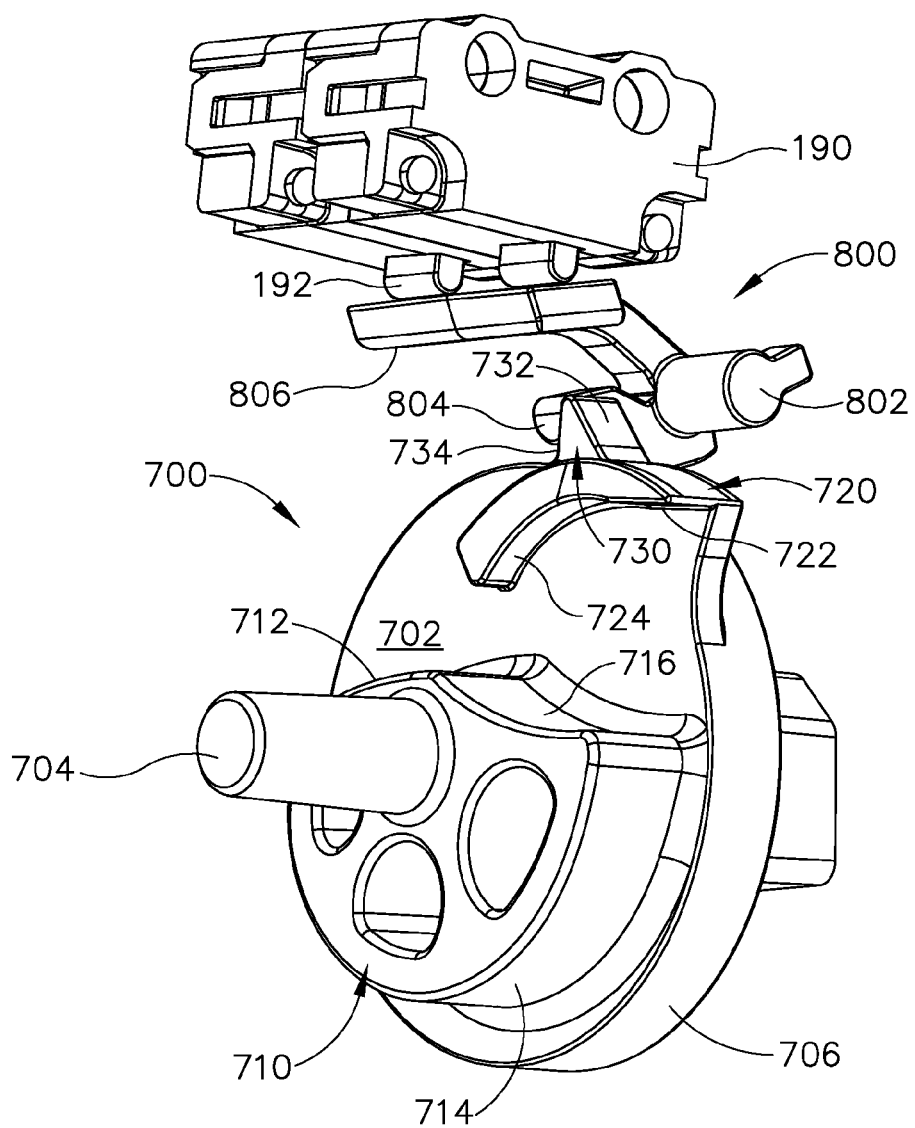
FIG. 19A depicts a perspective view of the rotary cam of FIG. 16, a rocker member, and a stop switch, with the rotary cam in a first angular position and the rocker member in a first pivotal position.
Figure 19B:
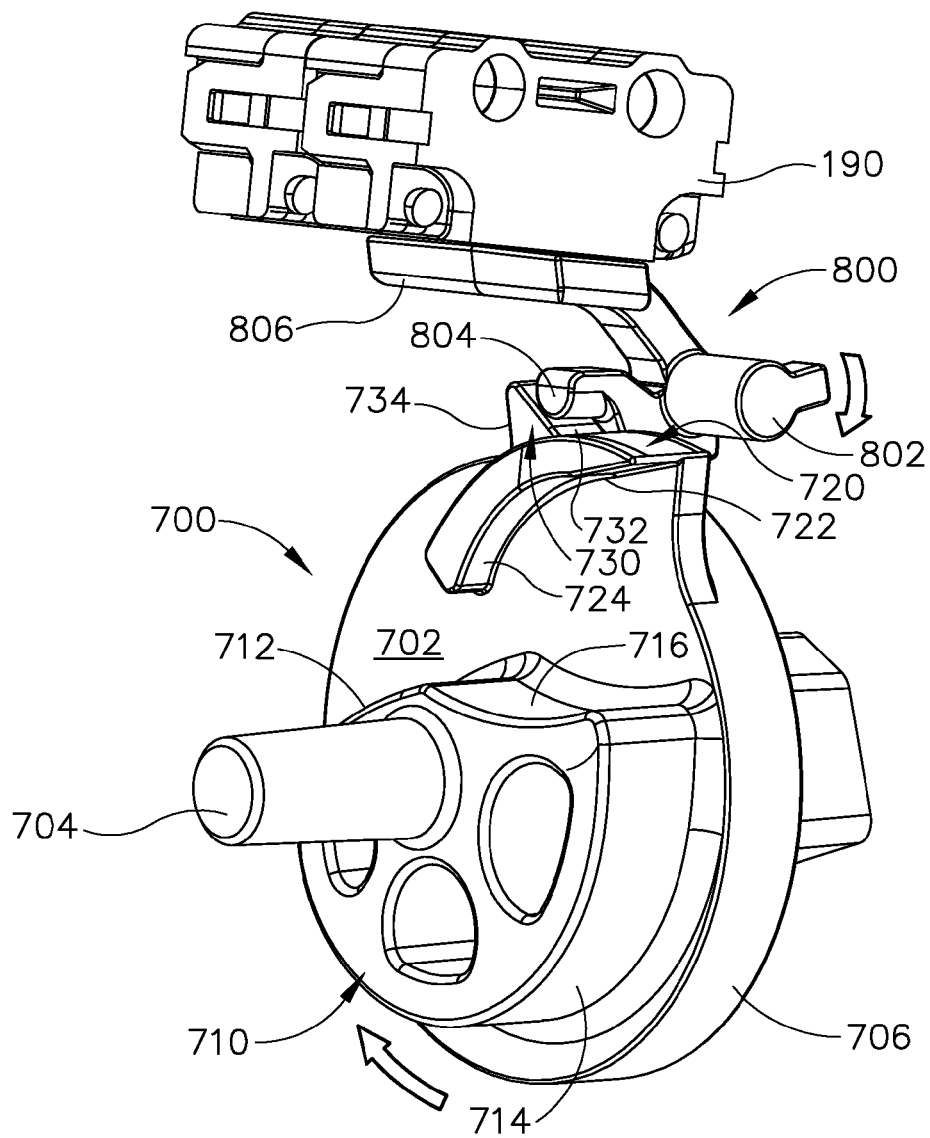
FIG. 19B depicts a perspective view of the rotary cam of FIG. 16, the rocker member of FIG. 19A, and the stop switch of FIG. 19A, with the rotary cam in a fourth angular position and the rocker member in a second pivotal position.

Referring back to FIGS. 16-17, a third cam feature (730) projects outwardly from outer circumferential surface (706). Third cam feature (730) comprises a first surface region (732) and a second surface region (734). First surface region (732) is flat and is oriented generally tangentially relative to outer circumferential surface (706). Second surface region (732) is also flat and is oriented radially outwardly relative to outer circumferential surface (706). Third cam feature (730) is configured to interact with a rocker member (800) as shown in FIGS. 19A-19B. Rocker member (800) comprises an integral pin (802), a bearing member (804), and a paddle (806). Pin (802) is pivotably coupled with casing (110), such that rocker member (800) is pivotable within casing (110) about the longitudinal axis defined by pin (802). Bearing member (804) is configured to interact with third cam feature (730) as will be described in greater detail below. Paddle (806) is configured to actuate a switch button (192) of a short circuit module (190) as will also be described in greater detail below.

FIG. 19A shows cam member (700) in the same position as shown in FIG. 18A. At this stage, second surface region (734) of third cam feature (730) is adjacent to bearing member (804) of rocker member (800). FIG. 19B shows cam member (700) in a position where cam member (700) has been rotated past the position shown in FIG. 18B and back toward the position shown in FIG. 18A. However, cam member (700) has not completed a full revolution. At the stage shown in FIG. 19B, first surface region (732) has engaged and borne against bearing member (804), thereby pivoting rocker member (800) about the longitudinal axis defined by pin (802). This has caused paddle (806) to actuate switch button (192) of short circuit module (190). Short circuit module (190) is configured to prevent motor (160) from further activation when switch button (192) has been actuated. In some versions, short circuit module (190) couples battery pack (120) with a power sink, in addition to short circuiting motor (160), when switch button (192) is actuated. This may result in discharge of battery pack (120) in addition to stopping activation of motor (160) once an actuation stroke of stapling head assembly (300) has been completed. By way of example only, short circuit module (190) may be configured and operable in accordance with at least some of the teachings of U.S. Pub. No. 2015/0083774, issued as U.S. Pat. No. 9,907,552 on Mar. 6, 2018, the disclosure of which is incorporated by reference herein. Other suitable configurations will be apparent to those of ordinary skill in the art in view of the teachings herein.

Figure 20A:
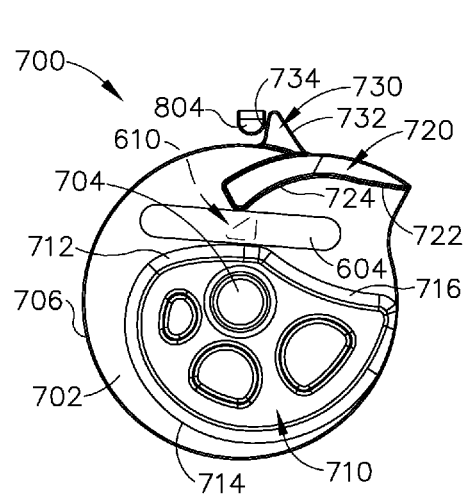
FIG. 20A depicts a schematic end view of the rotary cam of FIG. 16, the cam follower of FIG. 14, and the rocker member of FIG. 19A, with the rotary cam in the first angular position, the cam follower in the first pivotal position, and the rocker member in the first pivotal position.
Figure 20B:
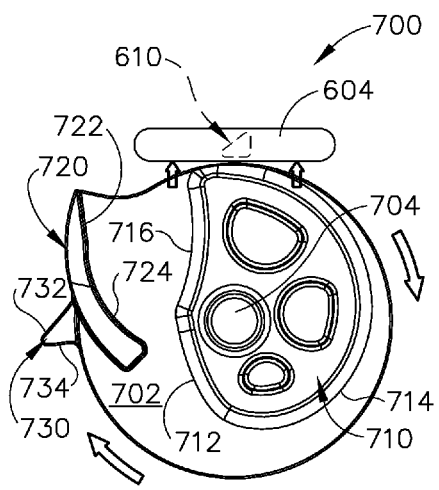
FIG. 20B depicts a schematic end view of the rotary cam of FIG. 16 and the cam follower of FIG. 14, with the rotary cam in the second angular position, the cam follower in the second pivotal position, and the rocker member of FIG. 19A in the first pivotal position.

FIGS. 20A-20D schematically depict the interaction between cam member (700), features of cam follower (600), and features of rocker member (800) as cam member (700) rotates. It should be understood that the rotation of cam member (700) throughout the stages shown in FIGS. 20A-20D is driven by motor (160) and gearbox (162). FIG. 20A shows cam member (700) in the same position as shown in FIGS. 18A and 19A. At this stage, first bearing feature (604) of cam follower (600) is positioned on first surface region (712) and bearing member (804) or rocker member (800) is adjacent to second surface region (734) of third cam feature (730). Also at this stage, knife member (340) and staple driver member (350) are in proximal positions, such that stapling head assembly (300) is in a non-actuated state. As cam member (700) is rotated to the position shown in FIG. 20B, second surface region (714) bears against bearing member (804), thereby driving bearing member (804) upwardly. This causes cam follower (600) to pivot about pin (118) to the position shown in FIG. 18B. Cam follower (600) thus drives knife member (340) and staple driver member (350) distally via drive bracket (250) and stapling head assembly driver (240). Stapling head assembly (300) is thus in an actuated state at the stage shown in FIG. 20B. In some versions, cam member (700) rotates through an angular range of approximately 270° in order to transition stapling head assembly (300) from the non-actuated state to the actuated state.

Figure 20C:
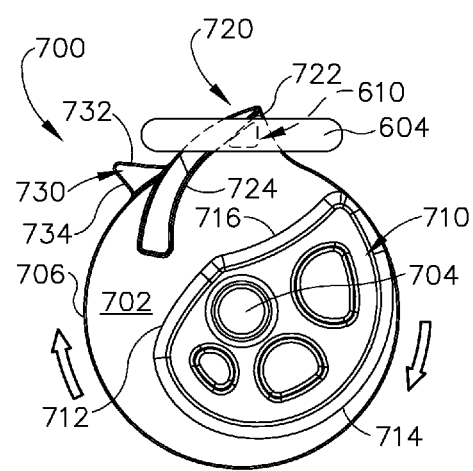
FIG. 20C depicts a schematic end view of the rotary cam of FIG. 16 and the cam follower of FIG. 14, with the rotary cam in a third angular position, the cam follower in the second pivotal position, and the rocker member of FIG. 19A in the first pivotal position.
Figure 20D:
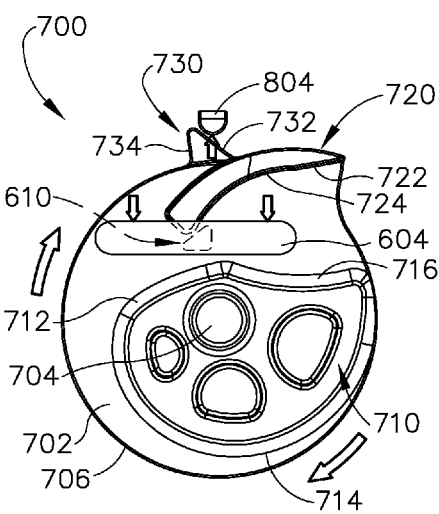
FIG. 20D depicts a schematic end view of the rotary cam of FIG. 16, the cam follower of FIG. 14, and the rocker member of FIG. 19A, with the rotary cam in a fourth angular position, the cam follower in a third pivotal position, and the rocker member in a second pivotal position.

After stapling head assembly (300) has been actuated, cam member (700) continues to rotate to the position shown in FIG. 20C. At this stage, first surface region (722) of second cam member (720) begins to engage curved surface (616) of second bearing feature (610) of cam follower (600). As cam member (700) continues to rotate to the position shown in FIG. 20D, second surface region (724) engages curved surface (616) of second bearing feature (610), driving second bearing feature (610) downwardly. This causes cam follower (600) to pivot about pin (118) back from the position shown in FIG. 18B toward the position shown in FIG. 18A. Cam follower (600) thus drives knife member (340) and staple driver member (350) proximally via drive bracket (250) and stapling head assembly driver (240). In addition, first surface region (732) has engaged and borne against bearing member (804), thereby pivoting rocker member (800) about the longitudinal axis defined by pin (802) at the stage shown in FIG. 20D. Rocker member (800) is thus in the same state in FIG. 20D as shown in FIG. 19B. Short circuit module (190) has thus been actuated at the stage shown in FIG. 20D.

It should be understood from the foregoing that cam member (700) is operable to drive knife member (340) and staple driver member (350) distally, then drive knife member (340) and staple driver member (350) proximally and actuate short circuit module (190) by rotating in a single angular direction through the range of motion shown in FIGS. 20A-20D. Other suitable ways in which knife member (340), staple driver member (350), and short circuit module (190) may be actuated will be apparent to those of ordinary skill in the art in view of the teachings herein.

E. Exemplary Anastomosis Procedure

Figure 21A:
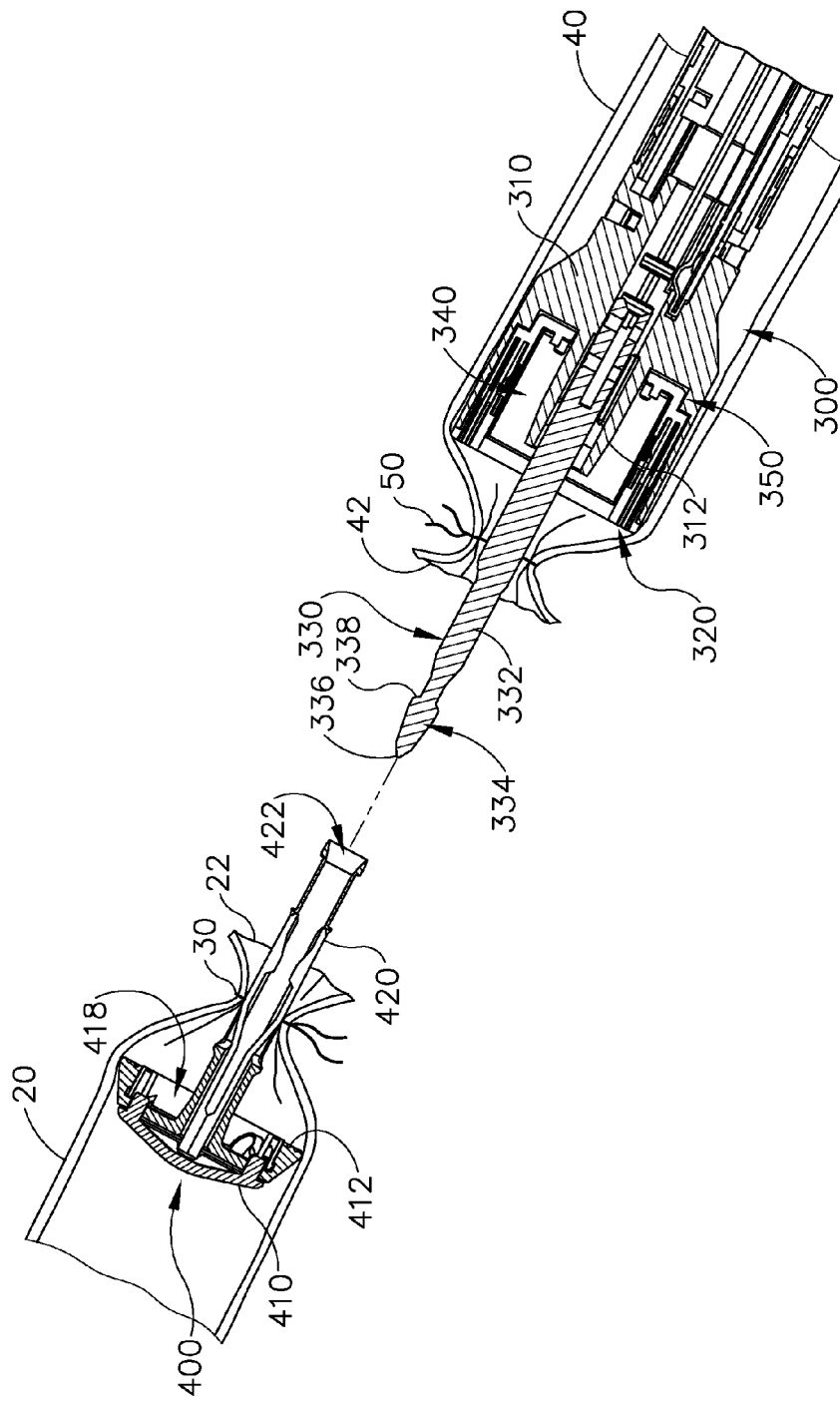
FIG. 21A depicts a cross-sectional side view of the anvil of FIG. 3 positioned within a first section of a digestive tract and the stapling head assembly of FIG. 6 positioned in a second section of the digestive tract, with the anvil separated from the stapling head assembly.
Figure 21B:
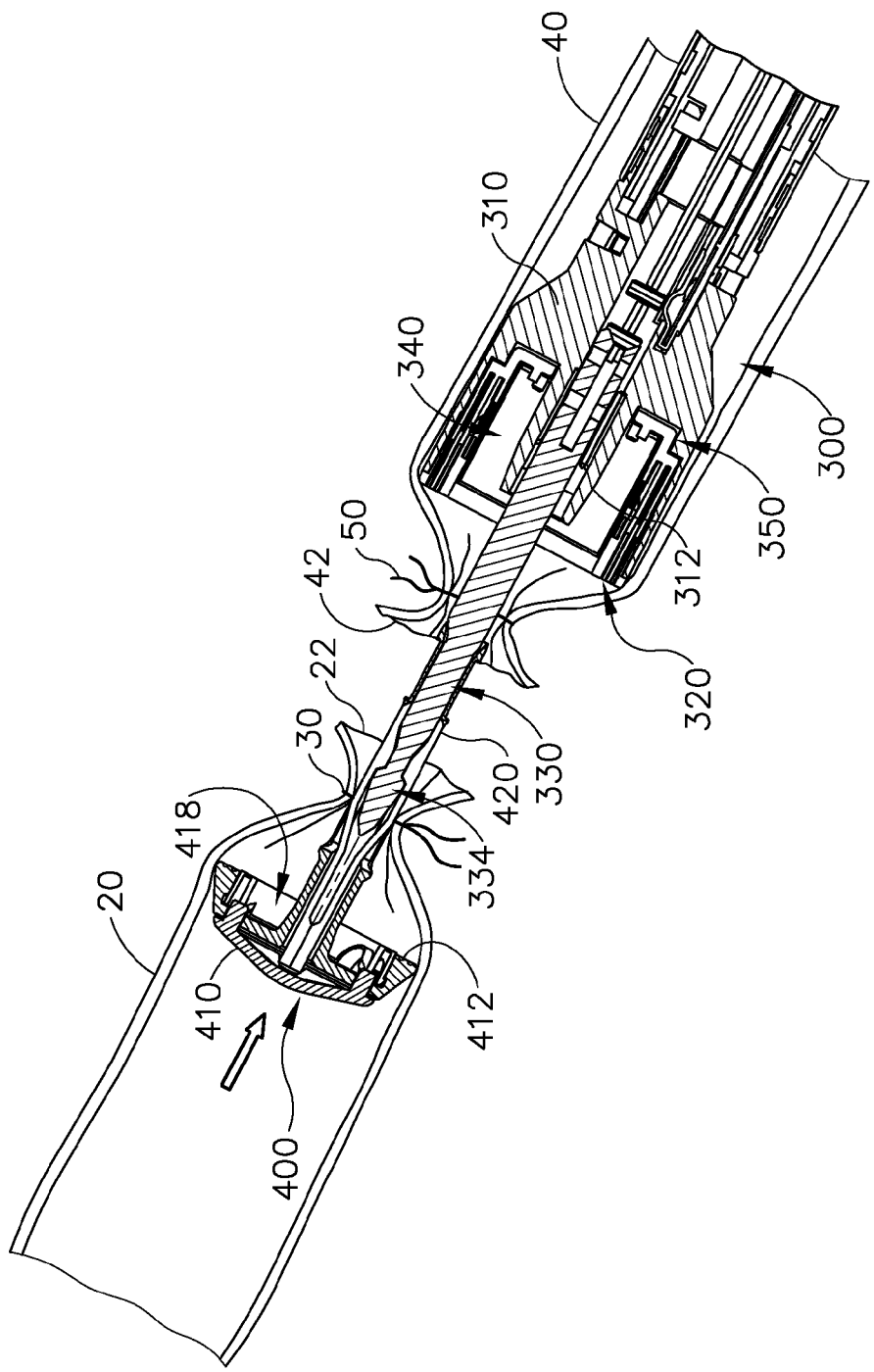
FIG. 21B depicts a cross-sectional side view of the anvil of FIG. 3 positioned within the first section of the digestive tract and the stapling head assembly of FIG. 6 positioned in the second section of the digestive tract, with the anvil secured to the stapling head assembly.
Figure 21C:
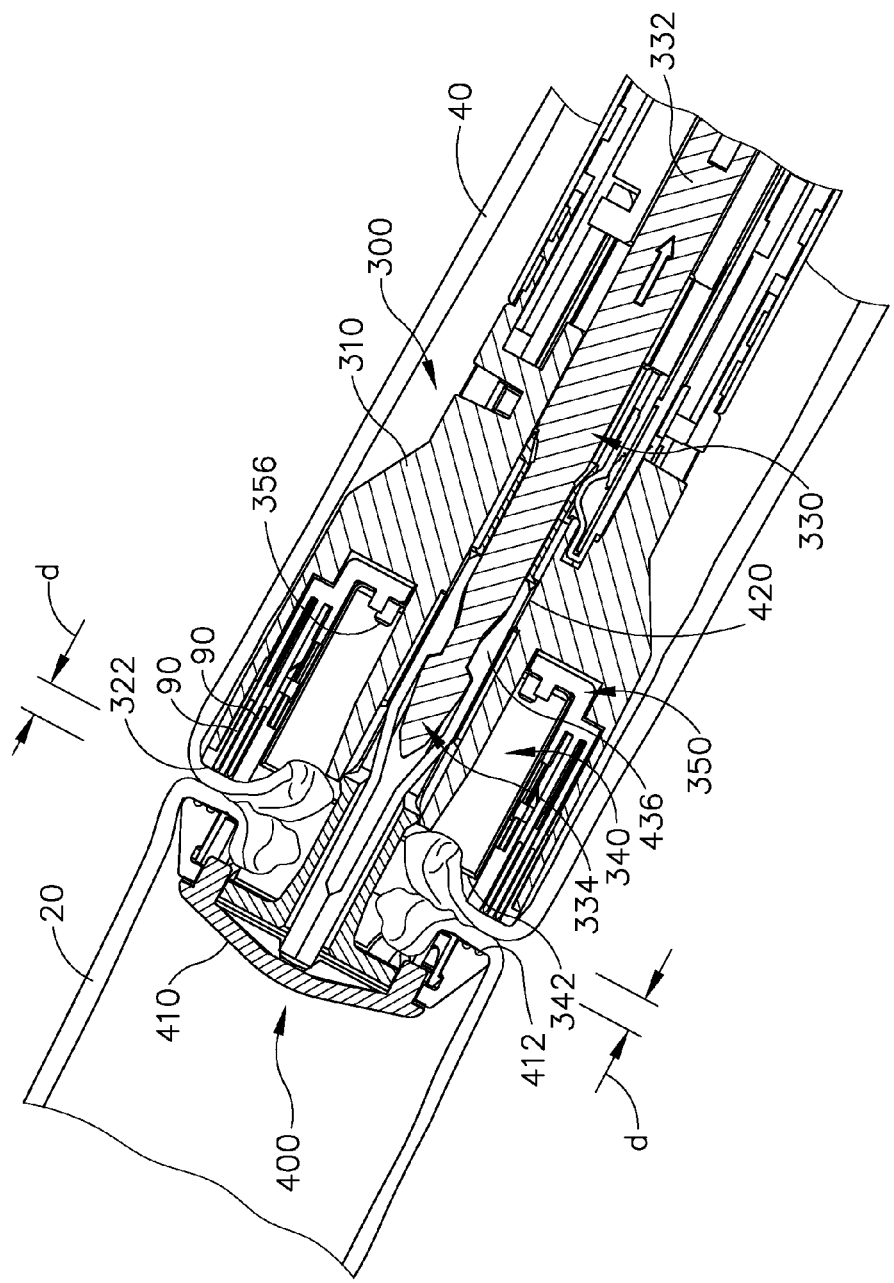
FIG. 21C depicts a cross-sectional side view of the anvil of FIG. 3 positioned within the first section of the digestive tract and the stapling head assembly of FIG. 6 positioned in the second section of the digestive tract, with the anvil retracted toward the stapling head assembly to thereby clamp tissue between the anvil and the stapling head assembly.

FIGS. 21A-21E show instrument (10) being used to form an anastomosis (70) between two tubular anatomical structures (20, 40). By way of example only, the tubular anatomical structures (20, 40) may comprise sections of a patient's esophagus, sections of a patient's colon, other sections of the patient's digestive tract, or any other tubular anatomical structures. As shown in FIG. 21A, anvil (400) is positioned in one tubular anatomical structure (20) and stapling head assembly (300) is positioned in another tubular anatomical structure (40). In versions where tubular anatomical structures (20, 40) comprise sections of a patient's colon, stapling head assembly (300) may be inserted via the patient's rectum. It should also be understood that the procedure depicted in FIGS. 21A-21E is an open surgical procedure, though the procedure may instead be performed laparoscopically. Various suitable ways in which instrument (10) may be used to form an anastomosis (70) in a laparoscopic procedure will be apparent to those of ordinary skill in the art in view of the teachings herein.

As shown in FIG. 21A, anvil (400) is positioned in tubular anatomical structure (20) such that shank (420) protrudes from the open severed end (22) of tubular anatomical structure (20). A purse-string suture (30) is provided about a mid-region of shank (420) to generally secure the position of anvil (400) in tubular anatomical structure (20). Similarly, stapling head assembly (300) is positioned in tubular anatomical structure (40) such that trocar (330) protrudes from the open severed end (42) of tubular anatomical structure (20). A purse-string suture (50) is provided about a mid-region of shaft (332) to generally secure the position of stapling head assembly (300) in tubular anatomical structure (40).

Next, anvil (400) is secured to trocar (330) by inserting trocar (330) into bore (422) as shown in FIG. 21B. Latch members (430) engage head (334) of trocar (330), thereby providing a secure fit between anvil (400) and trocar (330). The operator then rotates knob (130) while holding casing (110) stationary via pistol grip (112). This rotation of knob (130) causes trocar (330) and anvil (400) to retract proximally (as described above with reference to FIGS. 12A-12C). As shown in FIG. 21C, this proximal retraction of trocar (330) and anvil (400) compresses the tissue of tubular anatomical structures (20, 40) between surfaces (412, 322) of anvil (400) and stapling head assembly (300). The operator observes the position of needle (526) within window (114) to determine whether the gap distance (d) between opposing surfaces (412, 322) of anvil (400) and stapling head assembly (300) is appropriate; and makes any necessary adjustments via knob (130).

Figure 21D:
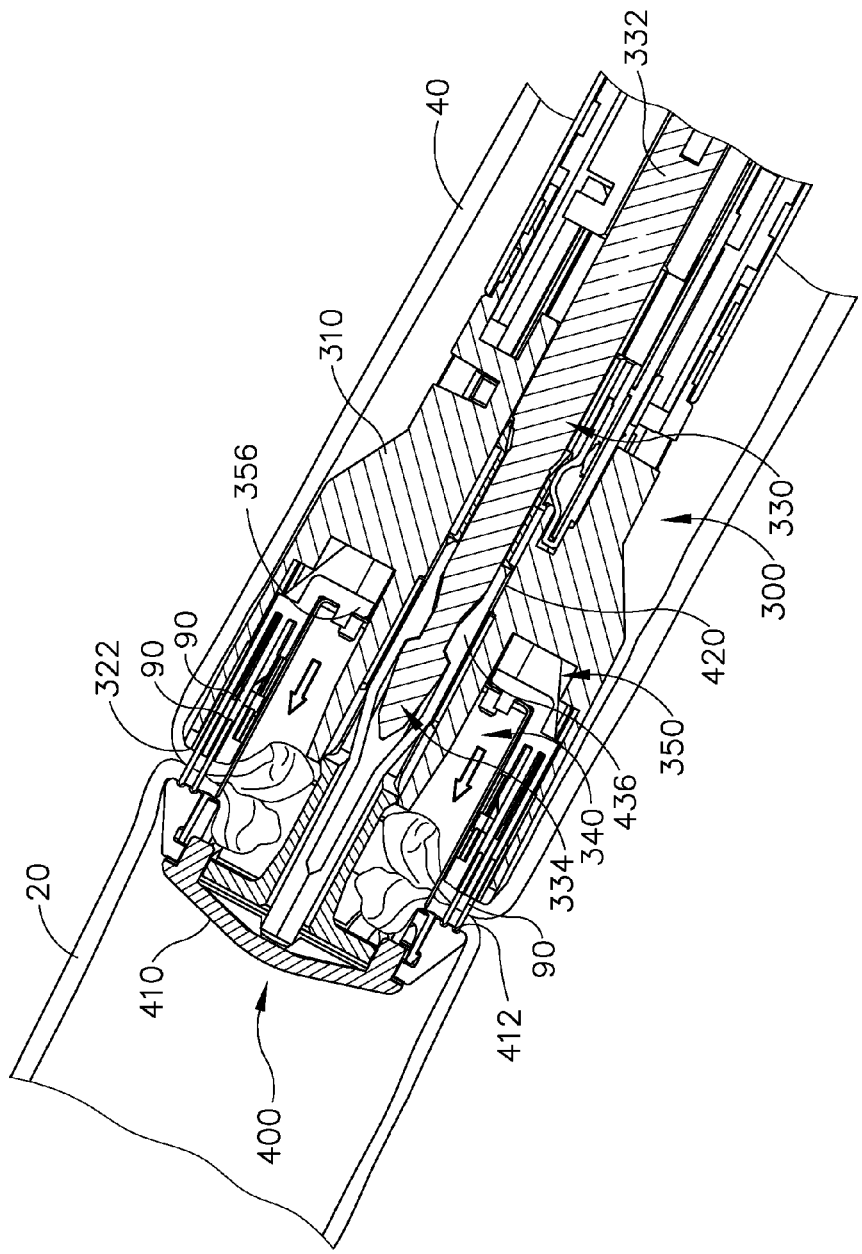
FIG. 21D depicts a cross-sectional side view of the anvil of FIG. 3 positioned within the first section of the digestive tract and the stapling head assembly of FIG. 6 positioned in the second section of the digestive tract, with the stapling head assembly actuated to sever and staple the clamped tissue.

Once the operator has appropriately set the gap distance (d) via knob (130), the operator actuates safety trigger (140) (as shown in FIG. 12D) to enable actuation of firing trigger (150). The operator then actuates firing trigger (150) (as shown in FIG. 12D). This causes paddle (158) to actuate the switch of a motor activation module (180), thereby activating motor to rotate cam member (700) (as shown in FIGS. 20A-20D). This rotation of cam member (700) actuates stapling head assembly (300) by driving knife member (340) and staple driver member (350) distally as shown in FIG. 21D. As knife member (340) translates distally, cutting edge (342) of knife member (340) cooperates with inner edge (416) of anvil (400), thereby shearing excess tissue that is positioned within annular recess (418) of anvil (400) and the interior of knife member (340).

As shown in FIG. 4, anvil (400) of the present example includes a breakable washer (417) within annular recess (418). This washer (417) is broken by knife member (340) when the knife member (340) completes a full distal range of motion from the position shown in FIG. 21C to the position shown in FIG. 21D. The progressively increasing radius of curvature of second surface region may provide an increasing mechanical advantage as knife member (340) reaches the end of its distal movement, thereby providing greater force by which to break the washer (417). Of course, the breakable washer (417) may be omitted entirely in some versions. In versions where washer (417) is included, it should be understood that washer (417) may also serve as a cutting board for knife member (340) to assist in cutting of tissue. Such a cutting technique may be employed in addition to or in lieu of the above-noted shearing action between inner edge (416) and knife member (340).

As staple driver member (350) translates distally from the position shown in FIG. 21C to the position shown in FIG. 21D, staple driver member (350) drives staples (90) through the tissue of tubular anatomical structures (20, 40) and into staple forming pockets (414) of anvil (400). Staple forming pockets (414) deform the driven staples (90) into a "B" shape as is known in the art. The formed staples (90) thus secure the ends of tissue together.

After the operator has actuated stapling head assembly (300) as shown in FIG. 21D, the operator rotates knob (130) to drive anvil (400) distally away from stapling head assembly (300), increasing the gap distance (d) to facilitate release of the tissue between surfaces (412, 322). The operator then removes instrument (10) from the patient, with anvil (400) still secured to trocar (330). Referring back to the example where the tubular anatomical structures (20, 40) comprise sections of a patient's colon, instrument (10) may be removed via the patient's rectum. With instrument (10) is removed, the tubular anatomical structures (20, 40) are left secured together by two annular arrays of staples (90) at an anastomosis (70) as shown in FIG. 21E. The inner diameter of the anastomosis (70) is defined by the severed edge (60) left by knife member (340).

II. Exemplary Alternative Features for Coupling Anvil and Stapling Head Assembly As noted above, prior to performing an anastomosis procedure, anvil (400) may be coupled to trocar (330) of stapling head assembly (300) after purse string sutures (30) are applied about anvil (400) and stapling head assembly (330) to substantially secure anatomical structures (20, 40) relative to anvil (400) and stapling head assembly (330). In some instances, it may be difficult to grasp anvil (400) without risking damage to the anvil (400) itself or tissue. For example, it may be difficult to couple trocar (330) to anvil (400) if a grasping instrument (e.g., a conventional surgical grasping instrument) is grasping one of latch members (430), for example. Moreover, reducing the amount of components in anvil (400) may reduce the likelihood of tissue interference and/or injury during use of anvil (400) and instrument (10), and may reduce manufacturing costs.

Figure 22:
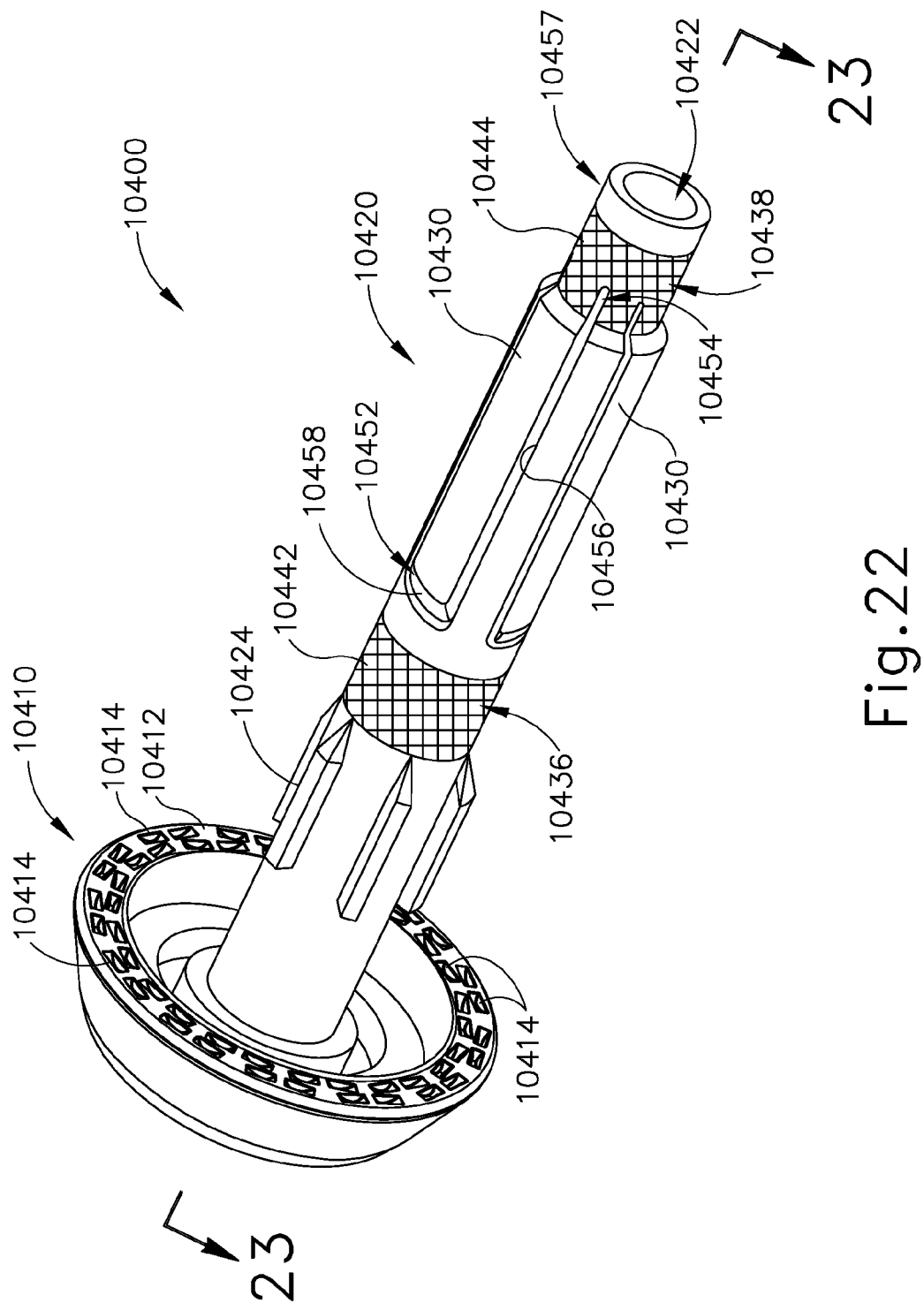
FIG. 22 depicts a perspective view of an exemplary alternative anvil suitable for incorporation into the circular stapler of FIG. 1.
Figure 23A:
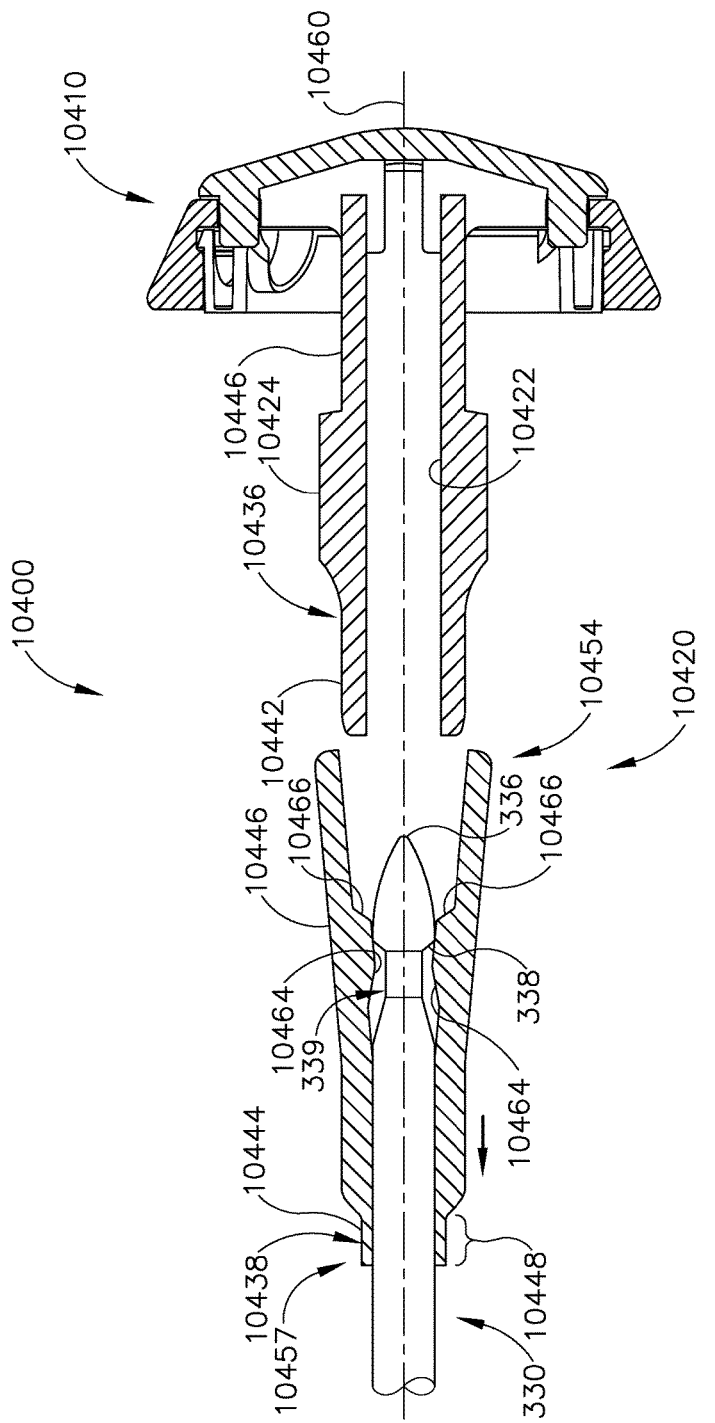
FIG. 23A depicts a side elevational view of a trocar of the stapling head assembly of FIG. 6 partially coupled with the anvil of FIG. 22, with the anvil being shown in a cross-section taken along line 23-23 of FIG. 22.
Figure 23B:
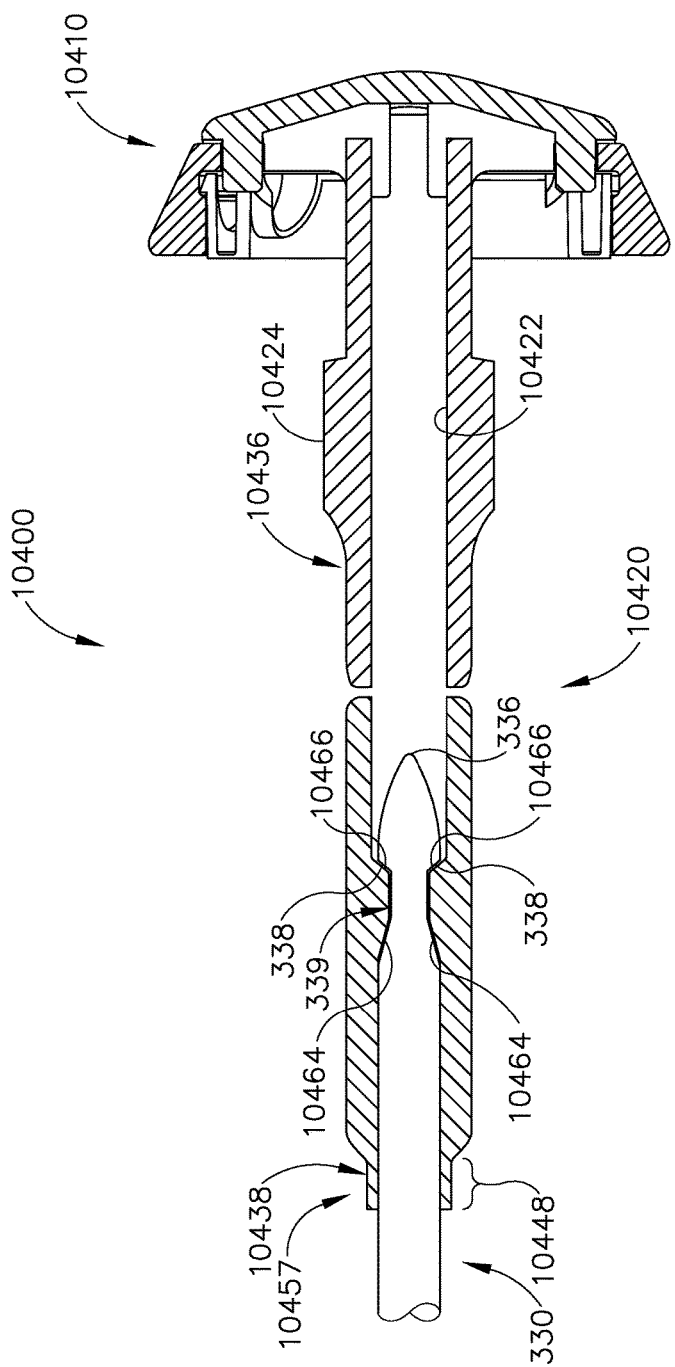
FIG. 23B depicts a side elevational view of a trocar of the stapling head assembly of FIG. 6 fully coupled with the anvil of FIG. 22, with the anvil being shown in a cross-section taken along line 23-23 of FIG. 22.

FIGS. 22-23B show an exemplary alternative anvil (10400) that is suitable for incorporation into a surgical instrument, such as surgical instrument (10). Particularly, anvil (10400) is configured to removably couple with shaft assembly (200) of instrument (10). However, anvil (10400) includes several different features that further enable an operator to couple anvil (10400) to the stapling head assembly (300) of shaft assembly (200), particularly to trocar (330) of stapling head assembly (300). When anvil (10400) is removably coupled to stapling head assembly (300), anvil (10400) and stapling head assembly (300) are configured to cooperate to manipulate tissue in the same manner discussed above with respect to anvil (400), including clamping the tissue, cutting the tissue, and stapling the tissue. In the following discussion of anvil (10400), the terms "distal" and "proximal" (and variations thereof) will be used with reference to the orientation of anvil (10400) when anvil (10400) is coupled with shaft assembly (200) of instrument (10). Thus, proximal features of anvil (10400) will be closer to the operator of instrument (10); while distal features of anvil (10400) will be further from the operator of instrument (10).

As best seen in FIGS. 22-23B, anvil (10400) of the present example comprises a head (10410) and a shank (10420). Head (10410) is configured to be substantially similar to head (410). Head (10410) includes a proximal surface (10412) that defines a plurality of staple forming pockets (10414). Staple forming pockets (10414) are arranged in two concentric annular arrays. In some other versions, staple forming pockets (10414) are arranged in three or more concentric annular arrays. Staple forming pockets (10414) are configured to deform staples as the staples are driven into staple forming pockets (10414), in the same manner as discussed above with respect to staple forming pockets (414). For instance, each staple forming pocket (10414) may deform a generally "U" shaped staple into a "B" shape as is known in the art.

Shank (10420) defines a bore or lumen (10422), splines (10424), grab zones (10436, 10438), and an engagement feature. In the present example, the engagement feature comprises latch members (10430). Splines (10424) are provided in order to allow the operator to properly angularly align anvil (10400) relative to stapling head assembly. Particularly, in the present example, splines (10424) include a substantially identical angular spacing as splines (313) of inner core member (312) of tubular casing (310) (FIGS. 6-7), such that the operator may visually observe the position of splines (10424) in relation to splines (313) in order to verify proper angular alignment of anvil (10400) in relation to stapling head assembly (300). Anvil (10400) and stapling head assembly (300) are configured such that when splines (10424) are aligned with respective splines (313) of inner core member (312) of tubular casing (310), staple forming pockets (10414) of anvil (10400) are aligned with staple openings (324) (FIGS. 6-7). In some other versions, inner core member (312) includes a plurality of interior guide channels that are configured to receive splines (10424) in order to provide proper angular alignment of anvil (10400) in relation to stapling head assembly (300). Such guide channels may include tapered distal portions that provide camming features to engage splines (10424) and thereby rotate anvil (10400) into alignment as needed when anvil (10400) is proximally retracted relative to stapling head assembly (300). Other suitable ways of providing or promoting proper angular alignment of anvil (10400) in relation to stapling head assembly (300) will be apparent to those of ordinary skill in the art in view of the teachings herein.

In the example shown, grab zones (10436, 10438) are provided with a textured surface (10442, 10444), respectively, to enhance the grip of a grasping instrument on shank (10420) while, for example, an operator couples anvil (10400) with trocar (330). Grab zones (10436, 10438) may also provide a visual indication to indicate where anvil (10400) should be engaged by a grasping instrument. Grab zone (10436) is positioned distal to latch members (10430) such that an operator may grasp grab zone (10436) without accidentally grasping, and potentially damaging latch members (10430) or tissue that is captured by the purse string suture (30), as discussed above with respect to FIGS. 21A-B. A portion of grab zone (10438) is positioned coincident with a proximal end or portion (10452) of latch members (10430). However, because latch members (10430) are connected to shank (10420) at proximal ends (10452) and because latch members (10430) pivot at a point at or near proximal ends (10452), the force or moment on latching members associated with an operator grasping grab zone (10438) is less likely to result in damage to latch members (10430).

As shown, textured surfaces (10442, 10444) include a knurled configuration. However, one or both of textured surfaces (10442, 10444) may include additional or alternative features that are integral or non-integral with shank (10420). The additional or alternative features may be, for example, a coating or alternative textures such as longitudinally extending ridges, annular ridges, etc. Other suitable configurations of textured surfaces (10442, 10444) will be apparent to persons skilled in the art in view of the teachings herein. Shank (10420) defines a first portion (10446) that is positioned distally of a second portion (10448). Second portion (10448) includes a smaller cross-sectional dimension (e.g., diameter) than first portion (10446) (in the configuration shown in FIGS. 22, 23B). Shank (10420) further defines a tapered portion (10450) between the first and second portions (10446, 10448). In other examples, however, the relative dimensions of different portions of shank (10420) may be different than those shown in FIGS. 22-23B. In the present example, textured surface (10444) is positioned coincident with second portion (10448).

Latch members (10430) are in communication with lumen (10422) such that when trocar (330) is received within lumen (10422), latch members (10430) secure anvil (10400) to trocar (330). As shown, latch members (10430) include a proximal end (10452) and a distal end (10454) and are integral with shank (10420). In the present example, each of latch member (10430) is formed at least in part from creating a pair of opposing longitudinal slits (10456) (e.g., cutouts) in shank (10420) and a transverse slit (10458) between the ends of longitudinal slits (10456). Transverse slits (10458) more particularly extend around a longitudinal axis (10460) of anvil (10400). Therefore, due to the configuration of the present example, latch members (10430) are configured to deflect outwardly about a point at or near proximal ends (10452) of latch members (10430). As seen best in FIG. 22, in the present example, longitudinal slits (10456) extend along first portion (10446), tapered portion (10450), and second portion (10448), but do not extend fully to and through the proximal end of shank (10420). Thus, proximal end (10457) of shank (10420) is radially fixed relative to axis (10460). Therefore, shank (10420) presents a proximal end (10457) that is more rigid than the portion of shank (10420) that is coincident with the slits (10456, 10458) and latch members (10430), thereby reducing the likelihood of damaging the shank (10420) (e.g., the latch members (10430)). Moreover, the absence of slits (10456) at proximal end (10457) of shank (10420) may reduce the likelihood of unwanted tissue interference before, during, and after the operator attempts to couple anvil (10400) to trocar (330).

In the present example, latch members (10430) are resiliently biased to the position shown in FIGS. 22 and 23B. Each latch members (10430) includes a radially inward protrusion (10461) including a proximal cam surface (10462) and a distal cam surface (10464). Cam surfaces (10462, 10464) are configured to provide radially outward flexing and radially inward flexing of latch members (10430), respectively, as trocar (330) is directed into lumen (10422). In particular, as trocar (330) is directed into lumen (10422), head (336) of trocar (330) rides against proximal cam surface (10462) and causes latch members (10430) to flex outwardly, as shown in FIG. 23A. As trocar (330) moves further distally, proximal surface (338) of trocar (330) rides against distal cam surface (10464) and allows latch members (10430) to flex back inwardly, as shown in FIG. 23B. Thus, anvil (10400) is removably coupled to stapling head assembly (300), enabling anvil (10400) and stapling head assembly (300) to cooperate to manipulate tissue as discussed herein, in a substantially similar manner as anvil (400) and stapling head assembly (300).

Figure 24:
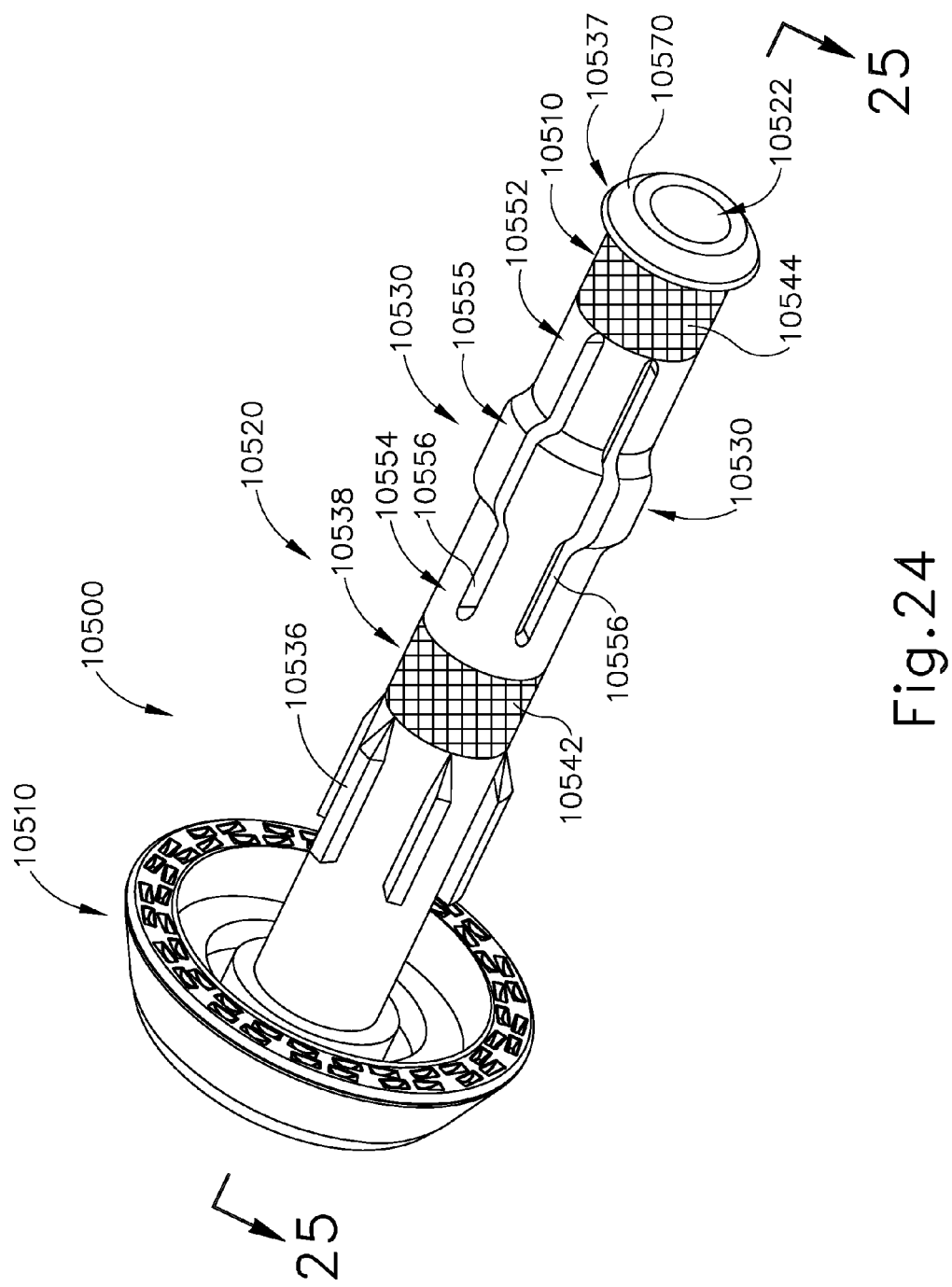
FIG. 24 depicts a perspective view of another exemplary alternative anvil suitable for incorporation into the circular stapler of FIG. 1.
Figure 25A:
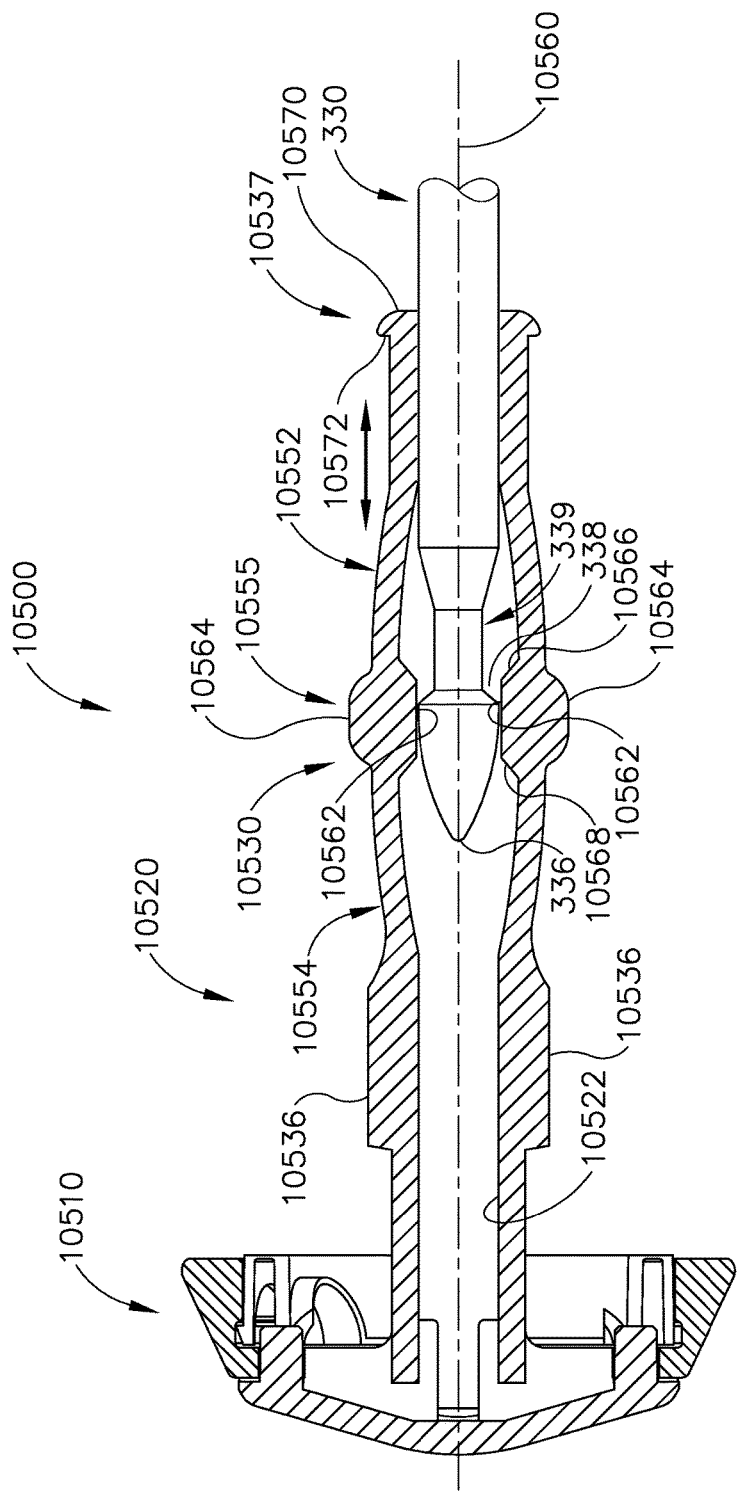
FIG. 25A depicts a side elevational view of a trocar of the stapling head assembly of FIG. 6 partially coupled with the anvil of FIG. 24, with the anvil being shown in a cross-section taken along line 25-25 of FIG. 24.
Figure 25B:
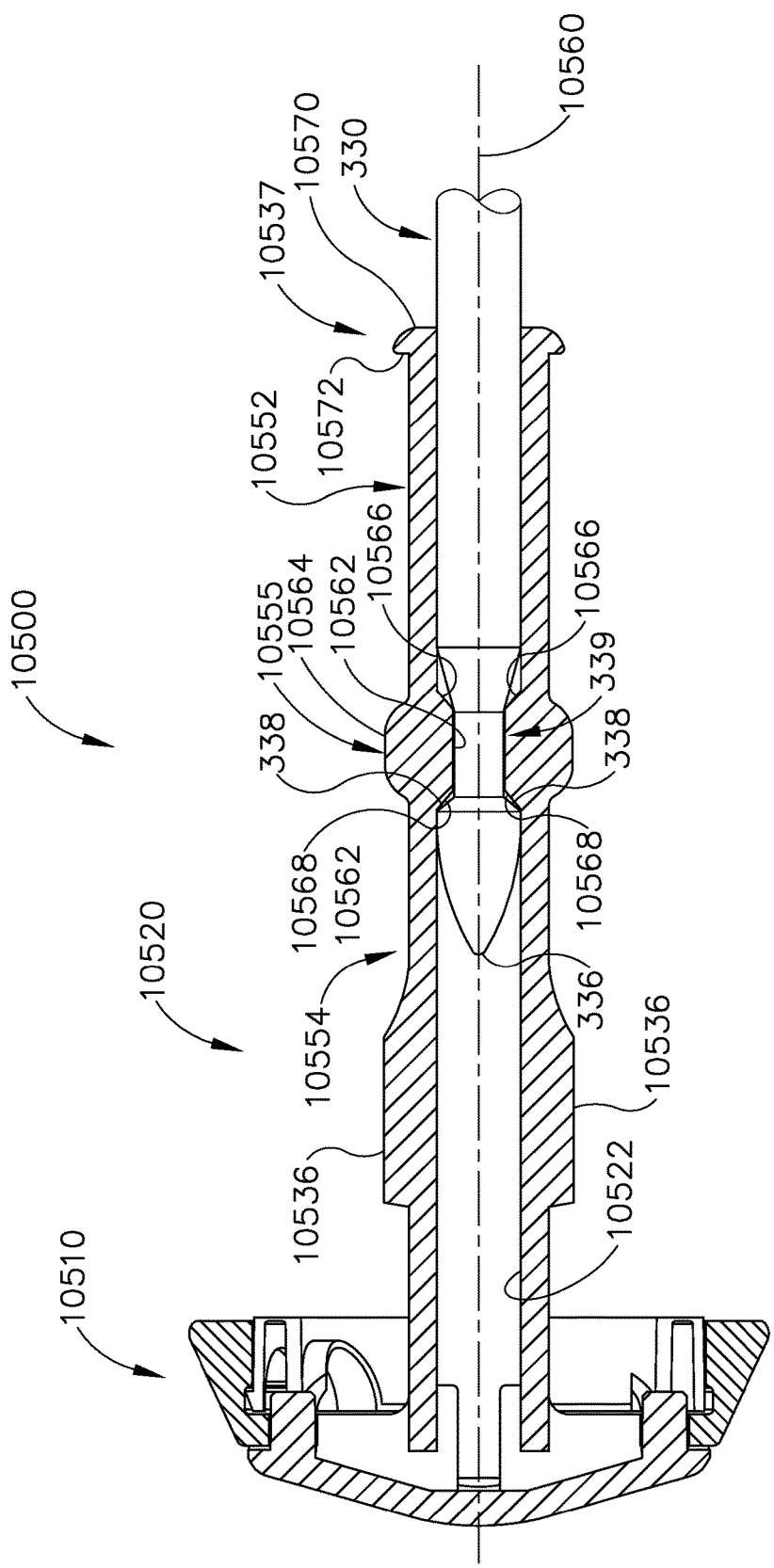
FIG. 25B depicts a side elevational view of a trocar of the stapling head assembly of FIG. 6 fully coupled with the anvil of FIG. 24, with the anvil being shown in a cross-section taken along line 25-25 of FIG. 24.

FIGS. 24-25B show another exemplary alternative anvil (10500) that is suitable for incorporation into a surgical instrument, such as surgical instrument (10). Anvil (10500) is configured to operate substantially similar to anvil (400, 10400), except for the differences discussed below. Anvil (10500) of the present example comprises a head (10510) and a shank (10520). Head (10510) is configured to operate substantially similarly to head (410, 10410). In that regard, head (10400) includes a proximal surface (10512) that defines a plurality of staple forming pockets (10514). Staple forming pockets (10514) are arranged in two concentric annular arrays. In some other versions, staple forming pockets (10514) are arranged in three or more concentric annular arrays. Staple forming pockets (10514) are configured to deform staples as the staples are driven into staple forming pockets (10514), in the same manner as discussed above with respect to staple forming pockets (414, 10414). For instance, each staple forming pocket (10514) may deform a generally "U" shaped staple into a "B" shape as is known in the art.

Shank (10520) defines a lumen (10522), splines (10536), grab zones (10538, 10540), and an engagement feature. In the present example, the engagement feature comprises resilient members (10530). Splines (10536) are provided in order to allow the operator to properly angularly align anvil (10500) relative to stapling head assembly. Particularly, in the present example, splines (10536) include a substantially identical angular spacing as splines (313) of inner core member (312) of tubular casing (310) (FIGS. 6-7), such that the operator may visually observe the position of splines (10536) in relation to splines (313) in order to verify proper angular alignment of anvil (10500) in relation to stapling head assembly (300). Anvil (10500) and stapling head assembly (300) are configured such that when splines (10524) are aligned with respective splines (313) of inner core member (312) of tubular casing (310), staple forming pockets (10514) of anvil (10500) are aligned with staple openings (324) (FIGS. 6-7). In some other versions, inner core member (312) includes a plurality of interior guide channels that are configured to receive splines (10524) in order to provide proper angular alignment of anvil (10500) in relation to stapling head assembly (300). Such guide channels may include tapered distal portions that provide camming features to engage splines (10524) and thereby rotate anvil (10500) into alignment as needed when anvil (10500) is proximally retracted relative to stapling head assembly (300). Other suitable ways of providing or promoting proper angular alignment of anvil (10500) in relation to stapling head assembly (300) will be apparent to those of ordinary skill in the art in view of the teachings herein.

In the example shown, grab zones (10538, 10540) are provided with a textured surface (10542, 10544), respectively, to enhance the grip of a grasping instrument on shank (10520) while, for example, an operator couples anvil (10500) with trocar (330). Grab zones (10538, 10540) may also provide a visual indication to indicate where anvil (10400) should be engaged by a grasping instrument. Grab zone (10538) is positioned distal to latch members (10430), and grab zone (10540) is positioned proximal to latch members (10430), such that an operator may grasp grab zone (10538, 10540) without accidentally grasping, and potentially damaging resilient members (10530) or tissue that is captured by the purse string suture (30), as discussed above with respect to FIGS. 21A-B.

As shown, textured surfaces (10542, 10544) include a knurled configuration. However, one or both of textured surfaces (10542, 10544) may include additional or alternative features that are integral or non-integral with shank (10520). The additional or alternative features may be, for example, a coating or alternative textures such as longitudinally extending ridges, annular ridges, etc. Other suitable configurations of textured surfaces (10542, 10544) will be apparent to persons skilled in the art in view of the teachings herein. As shown in the present example, shank (10520) includes the same cross-sectional dimension at each grab zone (10538, 10540). In other examples, however, the relative dimensions of different portions of shank (10520) may be different than those shown in FIGS. 24-25B.

Resilient members (10530) are in communication with lumen (10522) such that when trocar (330) is received within lumen (10522), resilient members (10530) secure anvil (10500) to trocar (330). As shown, resilient members (10530) include a proximal portion (10552), a distal portion (10554), and an intermediate portion (10555) therebetween. In the present example, resilient members (10530) are integral with shank (10520). In particular, resilient members (10530) are formed at least in part by the presence of longitudinal slits (10556), such that forming slits (10556) in shank (10520) facilitates deformation of the portions of shank (10520) defining resilient members (10530). Slits (10556) extend generally between grab zone (10538) and grab zone (10540), but do not extend fully to and through the proximal end (10537) of shank (10520). Thus, proximal end (10537) of shank (10520) is radially fixed relative to the longitudinal axis (10560) of shank (10520). Therefore, shank (10520) presents a proximal end (10537) that is more rigid than the portion of shank (10520) that is coincident with the slits (10556) and resilient members (10530), thereby reducing the likelihood of damaging the shank (e.g., the latch members (10430)). Moreover, the absence of slits (10456) at proximal end (10537) of shank (10520) may reduce the likelihood of unwanted tissue interference before, during, and after the operator attempts to couple anvil (10500) to trocar (330). Proximal end (10537) further includes a frustoconical shaped portion (10570) defining a lip (10572).

In the present example, intermediate portion (10555) includes a radially inward projection (10562) extending toward longitudinal axis (10560) of anvil (10500) and a radially outward projection (10564) extending away from axis (10560). Therefore, intermediate portion (10555) defines a portion of shank (10520) that includes a greater cross-sectional dimension than other portions of shank (10520), such as portions of shank coincident with grab zones (10538, 10540). In some versions, intermediate portion (10555) is marked in red or has some other visual indication that indicates to an operator that intermediate portion (10555) should not be grasped with a grasping instrument. Otherwise, if the operator grasps anvil (10500) by intermediate portion (10555), this may prevent intermediate portion (10555) from properly flexing outwardly as described below as the operator attempts to secure anvil (10500) to trocar (330).

In the example shown, radially inward projection (10562) includes a proximal cam surface (10566) and a distal cam surface (10568) that are configured to cause radially outward flexing and radially inward flexing, respectively, of resilient members (10530) as trocar (330) is directed into lumen (10522). In particular, as trocar (330) is directed into lumen (10522), proximal portion of head (336) of trocar (330) rides against proximal cam surface (10566) and causes resilient members (10530) to bow outwardly, as shown in FIG. 25A. As trocar (330) moves further distally, proximal surface (338) of trocar (330) rides against distal cam surface (10568) and allows resilient members (10530) to flex back inwardly, as shown in FIG. 25B. As shown, annular groove (339) of trocar receives inward projection (10562). Thus, anvil (10500) is removably coupled to stapling head assembly (300), enabling anvil (10500) and stapling head assembly (300) to cooperate to manipulate tissue as discussed herein.

Figure 26:
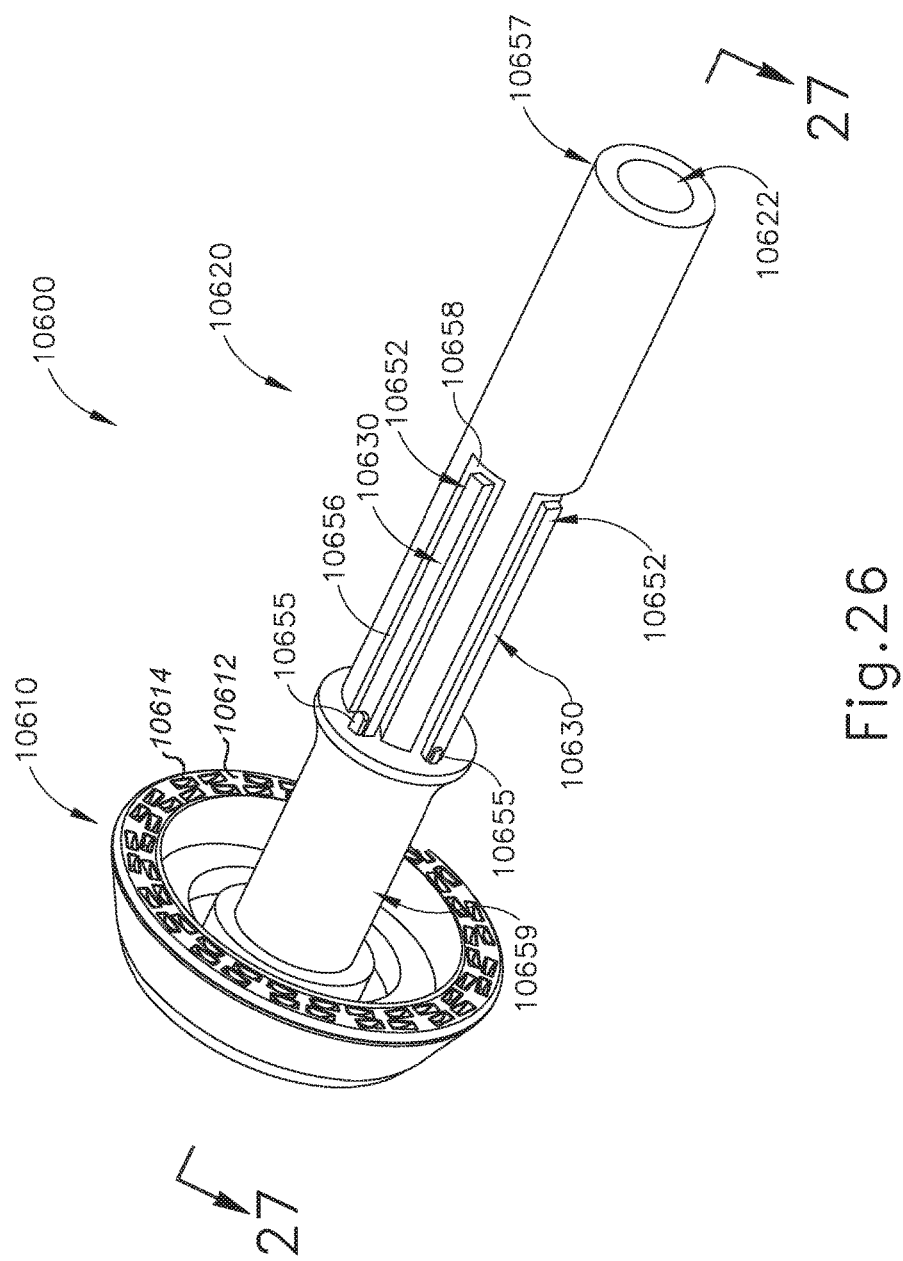
FIG. 26 depicts a perspective view of another exemplary alternative anvil suitable for incorporation into the circular stapler of FIG. 1.
Figure 27A:
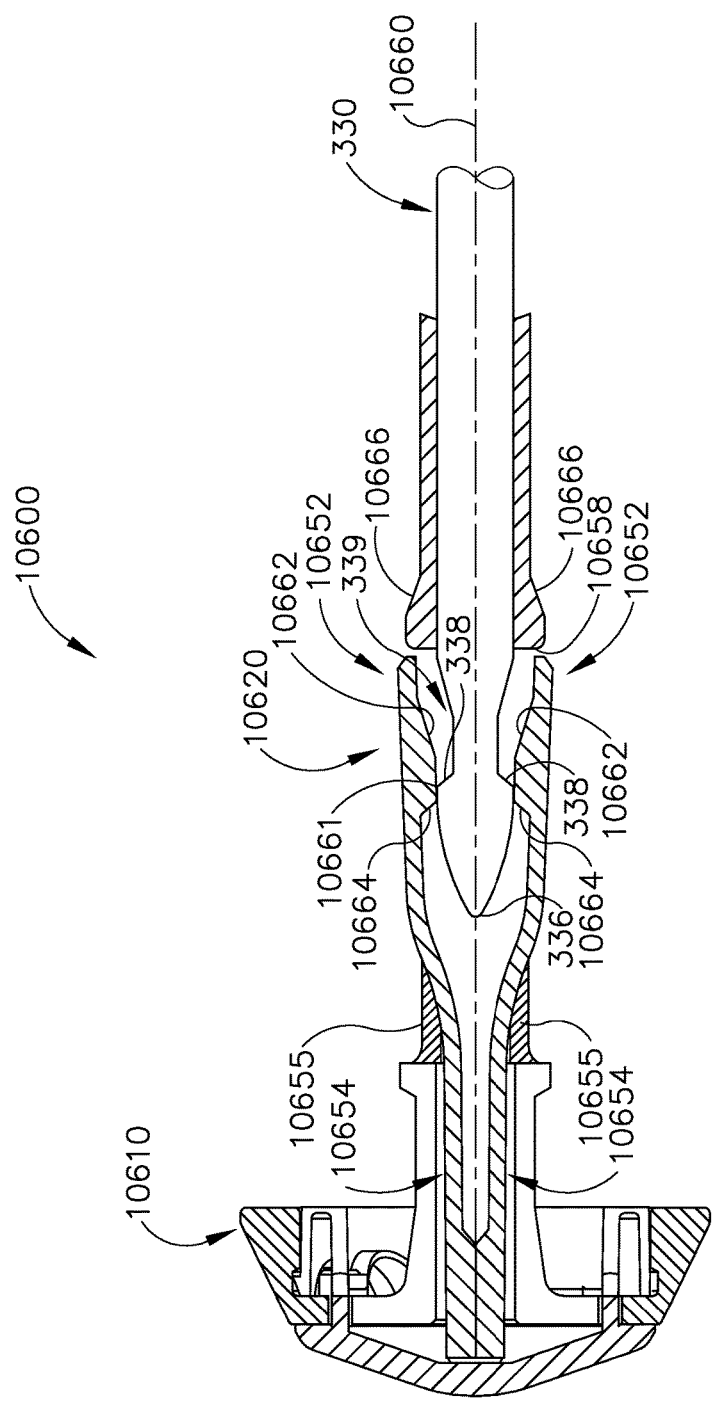
FIG. 27A depicts a side elevational view of a trocar of the stapling head assembly of FIG. 6 partially coupled with the anvil of FIG. 26, with the anvil being shown in a cross-section taken along line 27-27 of FIG. 26.
Figure 27B:
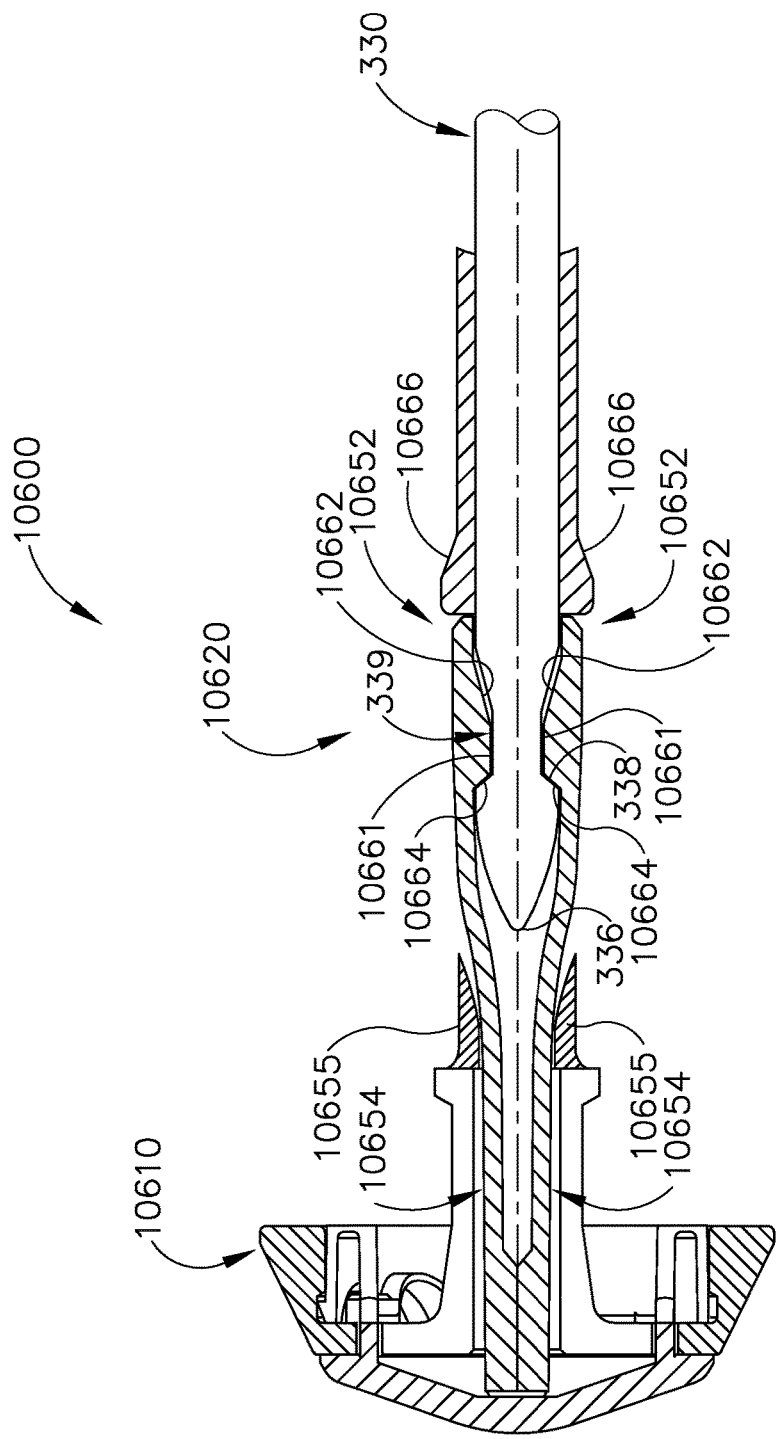
FIG. 27B depicts a side elevational view of a trocar of the stapling head assembly of FIG. 6 fully coupled with the anvil of FIG. 26, with the anvil being shown in a cross-section taken along line 27-27 of FIG. 26.

FIGS. 26-27B show another exemplary alternative anvil (10600) that is suitable for incorporation into a surgical instrument, such as surgical instrument (10). Particularly, anvil (10600) is configured to removably couple with shaft assembly (200) of instrument (10). However, anvil (10600) includes several different features that further enable an operator to couple anvil (10600) to the stapling head assembly (300) of shaft assembly (200), particularly to trocar (330) of stapling head assembly (300). When anvil (10600) is removably coupled to stapling head assembly (300), anvil (10600) and stapling head assembly (300) are configured to cooperate to manipulate tissue in the same manner discussed above with respect to anvil (400), including clamping the tissue, cutting the tissue, and stapling the tissue. In the following discussion of anvil (10600), the terms "distal" and "proximal" (and variations thereof) will be used with reference to the orientation of anvil (10600) when anvil (10600) is coupled with shaft assembly (200) of instrument (10). Thus, proximal features of anvil (10600) will be closer to the operator of instrument (10); while distal features of anvil (10600) will be further from the operator of instrument (10).

As best seen in FIGS. 26-27B, anvil (10600) of the present example comprises a head (10610) and a shank (10620). Head (10610) is configured to be substantially similar to head (410). Head (10610) includes a proximal surface (10612) that defines a plurality of staple forming pockets (10614). Staple forming pockets (10614) are arranged in two concentric annular arrays. In some other versions, staple forming pockets (10614) are arranged in three or more concentric annular arrays. Staple forming pockets (10614) are configured to deform staples as the staples are driven into staple forming pockets (10614), in the same manner as discussed above with respect to staple forming pockets (414, 10414, 10514). For instance, each staple forming pocket (10614) may deform a generally "U" shaped staple into a "B" shape as is known in the art.

Shank (10620) defines a lumen (10622) and an engagement feature. In the present example, the engagement feature comprises latch members (10630). Each latch member (10630) is formed at least in part from creating a pair of opposing longitudinal slits (10656) (e.g., cutouts) in shank (10620) and a transverse slit (10658) between the ends of longitudinal slits (10656). Transverse slits (10658) more particularly extend around a longitudinal axis (10660) of anvil (10600). Latch members include a proximal end (10652) and a distal end (10654) that extends into head (10610) of anvil (10600). Anvil (10600) includes a pivot limiting member (10655) that limits the pivoting of latch members outwardly relative to axis (10660). Therefore, due to the configuration of the present example, latch members (10630) are configured to pivot about a point at or near distal ends (10654) of latch members (10630), but are limited in the amount of pivoting due to the presence of member (10655).

As seen best in FIG. 26, in the present example, longitudinal slits (10656) extend along a portion that is between the proximal and distal ends (10657, 10659) of shank, but do not extend fully to and through the proximal end (10657) of shank (10620). Thus, proximal end (10657) of shank (10620) is radially fixed relative to axis (10460). Therefore, shank (10620) presents a proximal end (10657) that is more rigid than the portion of shank (10620) that is coincident with the slits (10656, 10658) and latch members (10630), thereby reducing the likelihood of damaging the shank (10620) (e.g., the latch members (10630)). Moreover, the absence of slits (10656) at proximal end (10657) of shank (10620) may reduce the likelihood of unwanted tissue interference before, during, and after the operator attempts to couple anvil (10400) to trocar (330). Furthermore, as best seen in FIGS. 27A-B, proximal ends (10652) of latch members (10630) are tapered in order to prevent unwanted tissue interference during use of anvil (10600). A tapered, increased cross-sectional dimension portion (10666) is provided on shank (10620) adjacent to slits (10658) to further prevent tissue interference. For instance, portion (10666) may prevent tissue from snagging on proximal ends (10652) of latch members (10630) and/or entering slits (10658), even when latch members (10630) are being deflected outwardly by trocar (330).

In the present example, latch members (10630) are resiliently biased to the position shown in FIGS. 26 and 27B. Each latch members (10630) includes a radially inward protrusion including (10661) a proximal cam surface (10662) and a distal cam surface (10664). Cam surfaces (10662, 10664) are configured to provide radially outward flexing and radially inward flexing, respectively, as trocar (330) is directed into lumen (10622). In particular, as trocar (330) is directed into lumen (10622), head (336) of trocar (330) rides against proximal cam surface (10662) and causes latch members (10630) to flex outwardly, as shown in FIG. 27A. As trocar (330) moves further distally, proximal surface (338) of trocar (330) rides against distal cam surface (10664) and allows latch members (10630) to flex back inwardly, as shown in FIG. 23B. Thus, anvil (10600) is removably coupled to stapling head assembly (300), enabling anvil (10600) and stapling head assembly (300) to cooperate to manipulate tissue as discussed herein, in a substantially similar manner as anvil (400) and stapling head assembly (300).

In the example shown, anvil (10600) does not include some of the features included in or on anvils (400, 10400, 10500). However, in other examples, anvil (10600) may include such features of anvils (400, 10400, 10500), such as grab zones (10436, 10438, 10538, 10540), splines (10424, 10536), and other features shown in FIGS. 22-25B.

Figure 28:
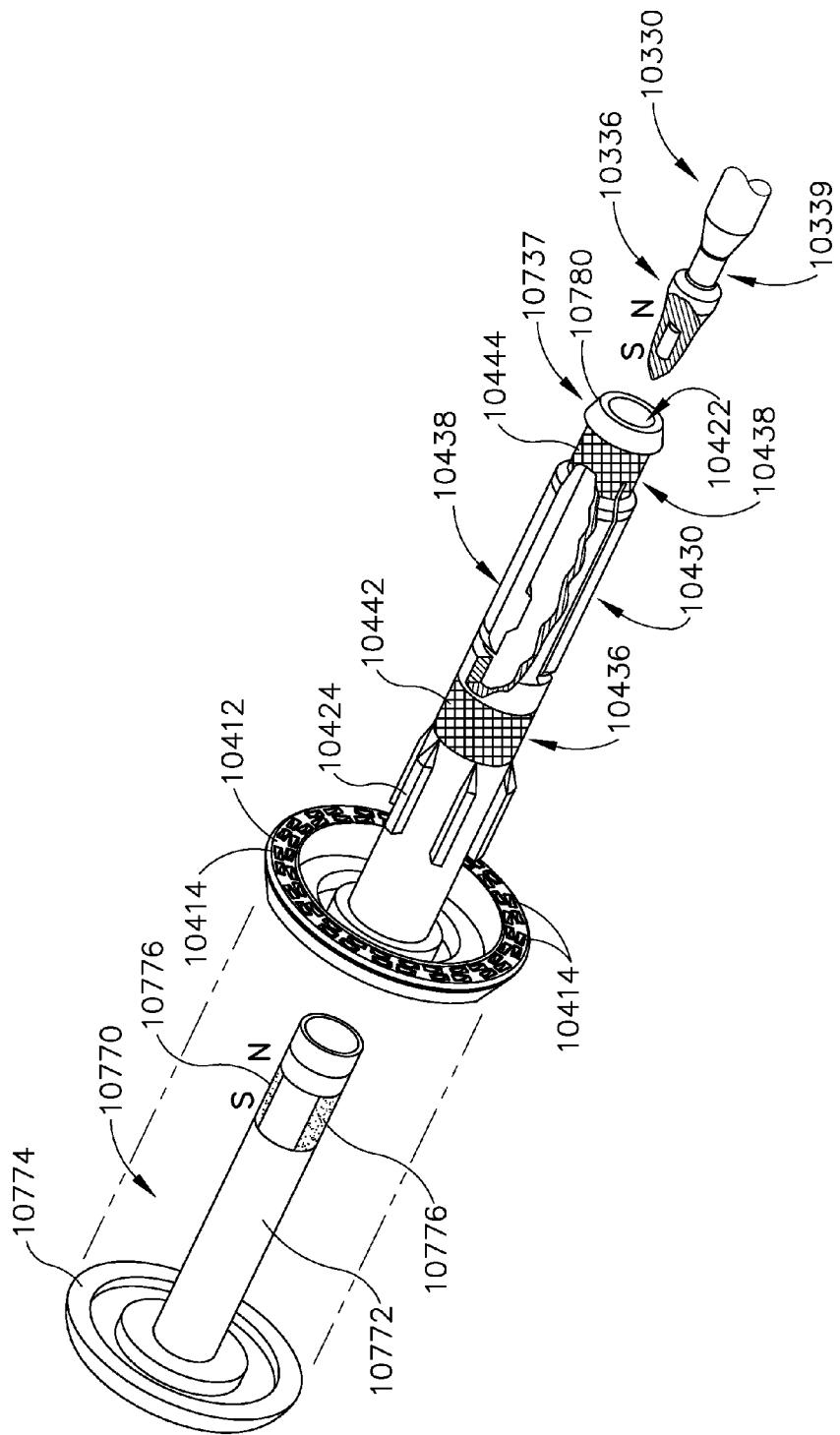
FIG. 28 depicts an exploded perspective view of another exemplary alternative anvil and an exemplary alternative trocar, each being suitable for incorporation into the circular stapler of FIG. 1.
Figure 29A:
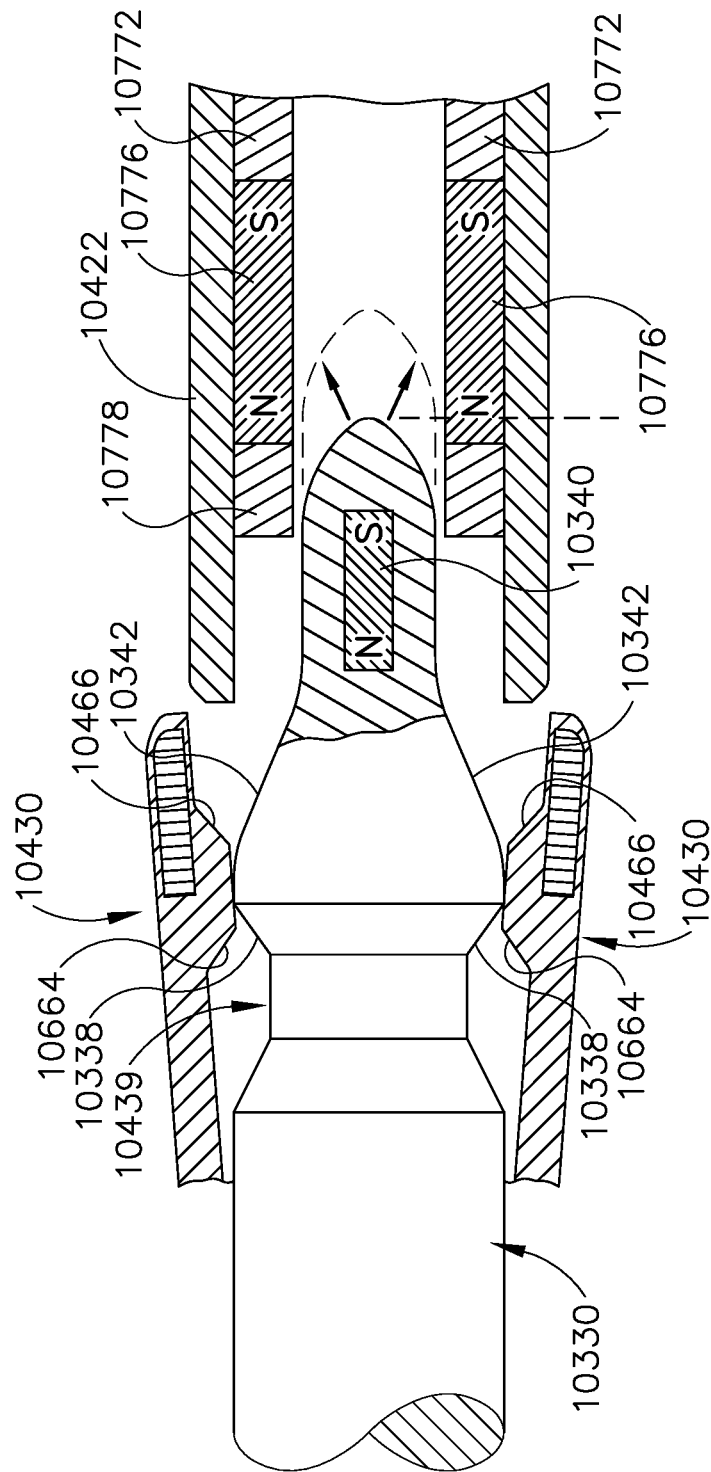
FIG. 29A depicts a partial, schematic view of the trocar of FIG. 28 partially coupled with the anvil of FIG. 28.

FIGS. 28-29A show another exemplary alternative anvil (10700) that is suitable for incorporation into a surgical instrument, such as surgical instrument (10). Particularly, anvil (10700) is configured to removably couple with shaft assembly (200) of instrument (10). However, anvil (10700) includes several different features that further enable an operator to couple anvil (10700) to the stapling head assembly (300) of shaft assembly (200), particularly to trocar (330) of stapling head assembly (300). When anvil (10700) is removably coupled to stapling head assembly (300), anvil (10700) and stapling head assembly (300) are configured to cooperate to manipulate tissue in the same manner discussed above with respect to anvil (400), including clamping the tissue, cutting the tissue, and stapling the tissue. In the following discussion of anvil (10700), the terms "distal" and "proximal" (and variations thereof) will be used with reference to the orientation of anvil (10700) when anvil (10700) is coupled with shaft assembly (200) of instrument (10). Thus, proximal features of anvil (10700) will be closer to the operator of instrument (10); while distal features of anvil (10700) will be further from the operator of instrument (10). FIGS. 28-29A also show a modified trocar (10330) that includes magnetic features that are configured to be magnetically coupled to magnetic features of anvil (10700), as discussed in more detail below.

Anvil (10700) of the present example includes features that are substantially similar to anvil (10400). For that reason, features of anvil (10700) that are substantially similar or identical to features of anvil (10400) are labeled with the same reference numbers without further discussion below. One of the differences between anvil (10400) and anvil (10700) is that anvil (10700) utilizes magnetic features, in addition to mechanical coupling features, to couple anvil (10700) with trocar (10300). Particularly, first head portion (10710) and shank (10722) receive a tubular member (10770) that includes a shaft (10772) and second head portion (10774). When shaft (10772) is received relative to head (10710) and shank (10722), first and second head portions (10710, 10774) collectively define a head of anvil (10700). As shown in the present example, shaft (10772) includes a magnetic feature (10776) with respective north and south poles (N, S). As seen best in FIGS. 29A-B, when shaft (10772) is received in shank (10722), proximal end (10778) of shaft (10772) is positioned distal to slits (10458) and therefore distal to latch members (10430). Proximal end (10737) further includes a frustoconical shaped portion (10780) defining a lip that is similar to the lip (10572) shown in FIGS. 25A-B.

Trocar (10330) is configured to operate substantially similar to trocar (330). Particularly, trocar (10330) is suitable as an alternative to trocar (330) in a stapling head assembly (300) of a surgical instrument, such as instrument (10). Trocar is different from trocar (330) in that trocar (10330) includes a modified, elongate head (10336) that is configured to accommodate a magnetic feature (10340) that includes a north pole (N) proximally and a south pole (S) distally. Trocar (10330) also includes a proximal cam feature (10338) and a distal cam feature (10342).

In the present example, magnetic features (10340, 10776) each comprise a discrete permanent magnet, such that magnetic feature (10340) is a separate component embedded in or coupled to trocar (10330) and magnetic feature (10776) are is a separate component embedded in or coupled to shaft (10772). By way of example only, magnetic feature (10776) may be in the form of an annular cuff or other cylindraceous structure. In some other versions, magnetic feature (10776) comprises a pair of discrete magnets that are located at the same longitudinal position along shaft (10772). It should also be understood that one or both of magnetic features (10340, 10776) may comprise an electromagnet. In other examples, magnetic features (10330, 10776) may be portions of trocar (10330) and/or tube (10772) that are magnetized as would be understood by persons skilled in the art. Additionally or alternatively, magnetic features (10340, 10776) may be a combination of any of the magnetic elements described herein.

As trocar (10330) is directed into lumen (10422), proximal cam feature (10338) of head (10336) of trocar (10330) rides against proximal cam surface (10464) and causes latch members (10430) to flex outwardly, as shown in FIG. 29A. As trocar (330) moves further distally, proximal surface (338) of trocar (330) rides against distal cam surface (10466) and allows latch members (10430) to flex back inwardly, as shown in FIG. 29B.

Figure 29B:
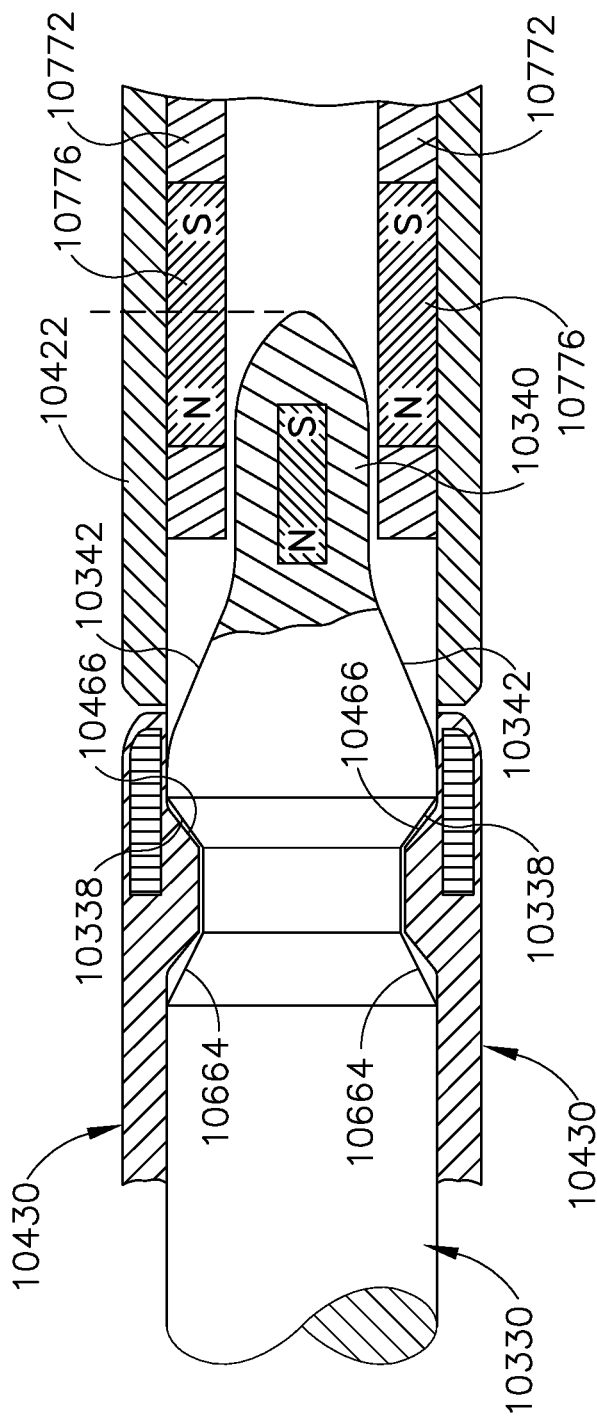
FIG. 29B depicts a partial, schematic view of the trocar of FIG. 28 fully coupled with the anvil of FIG. 28.

It should be understood that the south pole (S) of magnetic feature (10340) is substantially adjacent to the north pole (N) of magnetic feature (10776) at the stage shown in FIG. 29B. Thus, in addition to the mechanical coupling shown in FIG. 29B, magnetic feature (10340) is magnetically coupled to magnetic feature (10776) of shaft (10772), thus adding an additional measure of protection against an undesired decoupling of anvil (10700) from trocar (10330) (i.e., by requiring additional force to undesirably decouple anvil (10700) from trocar (10330)). Thus, with anvil (10400) removably coupled to stapling head assembly (300), anvil (10400) and stapling head assembly (300) are able to cooperate to manipulate tissue as discussed herein, in a substantially similar manner as anvil (400) and stapling head assembly (300). In addition to enhancing the security of the coupling between anvil (10440) and trocar (10330), magnetic features (10340, 10776) may cooperate to draw anvil (10440) proximally into full engagement with trocar (10330), such as when anvil (10440) is positioned as shown in FIG. 29A. In other words, the magnetic force of magnetic features (10340, 10776) may enable the operator to simply release anvil (10440) at the stage shown in FIG. 29A, with magnetic features (10340, 10776) cooperating to provide the final proximal movement of anvil (10440) to fully seat trocar (10333) in anvil (10440).

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical instrument for stapling tissue, the instrument comprising: (a) a body; (b) a shaft assembly extending from the body, wherein the shaft assembly comprises: (i) a stapling head assembly, and (ii) an actuator; and (c) an anvil configured to be selectively coupled to the actuator, wherein the anvil is configured to cooperate with the stapling head assembly to staple tissue, wherein the anvil comprises: (i) a head, and (ii) a shank extending from the head along an axis, the shank comprising: (A) a proximal end, (B) a distal end, (C) a lumen extending from the proximal end toward the distal end, and (D) an engagement feature between the proximal and distal ends, wherein the engagement feature is in communication with the lumen such that the engagement feature is configured to move relative to the axis in response to the actuator being directed into the lumen, wherein the engagement feature is configured to selectively couple the shank to the actuator, wherein the proximal end of the engagement feature is radially fixed relative to the axis.

Example 2

The instrument of any Example 1, wherein the engagement feature comprises a resilient member.

Example 3

The instrument of Example 2, wherein the resilient member is configured to flex outwardly relative to the axis in response to the actuator being directed into the lumen.

Example 4

The instrument of any one or more of Examples 2 through 3, wherein the resilient member is configured to flex back inwardly in response to the actuator being directed further into the lumen.

Example 5

The instrument of any one or more of Examples 3 through 4, wherein the resilient member comprises a proximal end and a distal end, wherein the resilient member is configured to flex about the distal end of the resilient member in response to the actuator being directed into the lumen.

Example 6

The instrument of any one or more of Examples 3 through 5, wherein the resilient member comprises a proximal end and a distal end, wherein the resilient member is configured to flex about the proximal end of the resilient member in response to the actuator being directed into the lumen.

Example 7

The instrument of any one or more of Examples 3 through 6, wherein the resilient member comprises a proximal end and a distal end, wherein the proximal and distal ends of the resilient member are fixed relative to the axis.

Example 8

The instrument of any one or more of Examples 2 through 7, wherein the resilient member is formed by at least one slit in the shank.

Example 9

The instrument of Example 8, wherein the at least one slit further comprises a longitudinal slit extending parallel to the axis.

Example 10

The instrument of any one or more of Examples 8 through 9, further comprising a transverse slit extending transversely relative to the longitudinal slit.

Example 11

The instrument of any one or more of Examples 1 through 10, wherein the engagement feature includes a first cam surface and a second cam surface, wherein the engagement feature is configured to move outwardly in response to the actuator riding against the first cam feature, wherein the engagement feature is configured to move inwardly in response to the actuator riding against the second cam feature.

Example 12

The instrument of any one or more of Examples 1 through 11, wherein the engagement feature comprises a protrusion, wherein the actuator comprises an annular groove configured to receive the protrusion.

Example 13

The instrument of any one or more of Examples 1 through 12, wherein the shank further comprises a plurality of splines extending radially outwardly from the shank.

Example 14

The instrument of any one or more of Examples 1 through 13, wherein the actuator comprises a trocar.

Example 15

The instrument of any one or more of Examples 1 through 14, wherein the shank comprises an outer surface, wherein the outer surface comprises a textured surface region.

Example 16

A surgical instrument for stapling tissue, the instrument comprising: (a) a body; (b) a shaft assembly extending from the body, wherein the shaft assembly comprises: (i) a stapling head assembly, and (ii) an actuator; and (c) an anvil configured to be selectively coupled to the actuator, wherein the anvil is configured to cooperate with the stapling head assembly to staple tissue, wherein the anvil comprises: (i) a head, and (ii) a shank extending from the head along an axis, the shank comprising: (A) an engagement feature configured to selectively couple the shank to the rod, and (B) an outer surface, wherein at least a portion of the outer surface comprises a first textured gripping region, wherein the first textured gripping region is not longitudinally offset from the engagement feature.

Example 17

The instrument of Example 16, wherein the first textured gripping region comprises a knurled configuration.

Example 18

The instrument of any or more of Examples 16 through 17, further comprising a second textured gripping region, wherein the engagement feature is longitudinally positioned between the first and second textured gripping regions.

Example 19

The instrument of any of any one or more Examples 16 through 18, wherein the shank further comprises: (A) a first portion having a first cross-sectional dimension, wherein the first textured gripping region is coincident with the first portion, and (B) a second portion having a second cross-sectional dimension, wherein the second cross-sectional dimension is less than the first cross-sectional dimension, wherein the second textured gripping region is coincident with the second portion.

Example 20

A surgical instrument for stapling tissue, the instrument comprising: (a) a body; (b) a shaft assembly extending from the body, wherein the shaft assembly comprises: (i) a stapling head assembly, and (ii) an actuator; and (c) an anvil configured to be selectively coupled to the actuator, wherein the anvil is configured to cooperate with the stapling head assembly to staple tissue, wherein the anvil comprises: (i) a head, and (ii) a shank extending from the head along an axis, the shank comprising: (A) a proximal end, (B) a distal end, and (C) an engagement feature between the proximal and distal ends, wherein the engagement feature is configured to selectively couple the shank to the rod, wherein the engagement feature comprises a set of resilient arms formed by a plurality of slits formed in the shank.

IV. Miscellaneous

It should also be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

At least some of the teachings herein may be readily combined with one or more teachings of U.S. Pat. No. 7,794,475, entitled "Surgical Staples Having Compressible or Crushable Members for Securing Tissue Therein and Stapling Instruments for Deploying the Same," issued Sep. 14, 2010, the disclosure of which is incorporated by reference herein; U.S. Pub. No. 2014/0151429, entitled "Trans-Oral Circular Anvil Introduction System with Dilation Feature," published Jun. 5, 2014, issued as U.S. Pat. No. 9,572,573 on Feb. 21, 2017, the disclosure of which is incorporated by reference herein; U.S. Pub. No. 2014/0144968, entitled "Surgical Staple with Integral Pledget for Tip Deflection," published May 29, 2014, issued as U.S. Pat. No. 9,289,207 on Mar. 22, 2016, the disclosure of which is incorporated by reference herein; U.S. Pub. No. 2014/0158747, entitled "Surgical Stapler with Varying Staple Widths along Different Circumferences," published Jun. 12, 2014, now abandoned, the disclosure of which is incorporated by reference herein; U.S. Pub. No. 2014/0144969, entitled "Pivoting Anvil for Surgical Circular Stapler," published May 29, 2014, issued as U.S. Pat. No. 9,498,222 on Nov. 22, 2016, the disclosure of which is incorporated by reference herein; U.S. Pub. No. 2014/0151430, entitled "Circular Anvil Introduction System with Alignment Feature," published Jun. 5, 2014, issued as U.S. Pat. No. 9,724,100 on Aug. 8, 2017, the disclosure of which is incorporated by reference herein; U.S. Pub. No. 2014/0166717, entitled "Circular Stapler with Selectable Motorized and Manual Control, Including a Control Ring," published Jun. 19, 2014, issued as U.S. Pat. No. 9,532,783 on Jan. 3, 2017, the disclosure of which is incorporated by reference herein; U.S. Pub. No. 2014/0166728, entitled "Motor Driven Rotary Input Circular Stapler with Modular End Effector," published Jun. 19, 2014, issued as U.S. Pat. No. 9,597,081 on Mar. 21, 2017, the disclosure of which is incorporated by reference herein; and/or U.S. Pub. No. 2014/0166718, entitled "Motor Driven Rotary Input Circular Stapler with Lockable Flexible Shaft," published Jun. 19, 2014, issued as U.S. Pat. No. 9,463,022 on Oct. 11, 2016, the disclosure of which is incorporated by reference herein.

Various suitable ways in which such teachings may be combined will be apparent to those of ordinary skill in the art.

While the examples herein have been provided in the context of a circular stapling instrument, it should be understood that the various teachings herein may be readily applied to various other kinds of surgical instruments. By way of example only, the various teachings herein may be readily applied to linear stapling devices (e.g., endocutters). For instance, various teachings herein may be readily combined with various teachings of U.S. Pub. No. 2012/0239012, entitled "Motor-Driven Surgical Cutting Instrument with Electric Actuator Directional Control Assembly," published Sep. 20, 2012, issued as U.S. Pat. No. 8,453,914 on Jun. 4, 2103, the disclosure of which is incorporated by reference herein, and/or U.S. Pub. No. 2010/0264193, entitled "Surgical Stapling Instrument with An Articulatable End Effector," published Oct. 21, 2010, issued as U.S. Pat. No. 8,408,439 on Apr. 2, 2013, the disclosure of which is incorporated by reference herein, as will be apparent to those of ordinary skill in the art. As another merely illustrative example, the various teachings herein may be readily applied to a motorized electrosurgical device. For instance, various teachings herein may be readily combined with various teachings of U.S. Pub. No. 2012/0116379, entitled "Motor Driven Electrosurgical Device with Mechanical and Electrical Feedback," published May 10, 2012, issued as U.S. Pat. No. 9,161,803 on Oct. 20, 2015, the disclosure of which is incorporated by reference herein, as will be apparent to those of ordinary skill in the art. Other suitable kinds of instruments in which the teachings herein may be applied, and various ways in which the teachings herein may be applied to such instruments, will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometric s, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument for stapling tissue, the instrument comprising:
   (a) a body;
   (b) a shaft assembly extending from the body, wherein the shaft assembly comprises:
      (i) a stapling head assembly, and
      (ii) an actuator; and
   (c) an anvil configured to be selectively coupled to the actuator, wherein the anvil is configured to cooperate with the stapling head assembly to staple tissue, wherein the anvil comprises:
      (i) a head, and
      (ii) a shank extending from the head along an axis, the shank comprising:
         (A) a proximal end,
         (B) a distal end,
         (C) a lumen extending from the proximal end toward the distal end,
         (D) an engagement feature between the proximal and distal ends,
         (E) a tapered, increased cross-sectional dimension portion disposed adjacent the engagement feature configured to prevent tissue interference, and
         (F) a pivot limiting member having a proximal end and a distal end, wherein the pivot limiting member is configured to limit the engagement feature pivoting outwardly relative to the axis, wherein when the actuator is partially coupled with the shank, the proximal end of the pivot limiting member is in contact with the engagement feature, and wherein when the actuator is fully coupled with the shank, the proximal end of the pivot limiting member is separated at a distance from the engagement feature,
wherein the engagement feature is in communication with the lumen such that the engagement feature is configured to move relative to the axis in response to the actuator being directed into the lumen,
wherein the engagement feature is configured to selectively couple the shank to the actuator,
wherein a proximal end of the engagement feature extends freely from the shank.

2. The surgical instrument according to claim 1, wherein the engagement feature comprises a resilient member.

3. The surgical instrument according to claim 2, wherein the resilient member is configured to flex outwardly relative to the axis in response to the actuator being directed into the lumen.

4. The surgical instrument according to claim 3, wherein the resilient member is configured to flex back inwardly in response to the actuator being directed further into the lumen.

5. The surgical instrument according to claim 3, wherein the resilient member comprises a proximal end and a distal end, wherein the resilient member is configured to flex about the distal end of the resilient member in response to the actuator being directed into the lumen.

6. The surgical instrument according to claim 2, wherein the resilient member is formed by at least one slit in the shank.

7. The surgical instrument according to claim 6, wherein the at least one slit further comprises a longitudinal slit extending parallel to the axis.

8. The surgical instrument according to claim 6, further comprising a transverse slit extending transversely relative to the longitudinal slit.

9. The surgical instrument according to claim 1, wherein the engagement feature includes a first cam surface and a second cam surface, wherein the engagement feature is configured to move outwardly in response to the actuator riding against the first cam surface, wherein the engagement feature is configured to move inwardly in response to the actuator reaching the second cam surface.

10. The surgical instrument according to claim 1, wherein the engagement feature comprises a protrusion, wherein the actuator comprises an annular groove configured to receive the protrusion.

11. The surgical instrument according to claim 1, wherein the shank further comprises a plurality of splines extending radially outwardly from the shank.

12. The surgical instrument according to claim 1, wherein the actuator comprises a trocar.

13. A surgical instrument for stapling tissue, the instrument comprising:
(a) a body;
(b) a shaft assembly extending from the body, wherein the shaft assembly comprises:
(i) a stapling head assembly, and
(ii) an actuator; and
(c) an anvil configured to be selectively coupled to the actuator, wherein the anvil is configured to cooperate with the stapling head assembly to staple tissue, wherein the anvil comprises:
(i) a head, and
(ii) a shank extending from the head along an axis, the shank comprising:
(A) a proximal end,
(B) a distal end,
(C) an engagement feature between the proximal and distal ends, wherein the engagement feature is configured to selectively couple the shank to the actuator, wherein the engagement feature comprises a set of resilient arms formed by a plurality of slits formed in the shank, and
(D) a set of pivot limiting members configured to limit the resilient arms pivoting outwardly relative to the axis.

14. The surgical instrument according to claim 1, wherein the engagement feature is formed at least in part from a pair of opposing longitudinal slits in the shank and a transverse slit extending between the opposing longitudinal slits, wherein the transverse slit extends around at least a portion of the axis.

15. The surgical instrument according to claim 14, wherein the tapered, increased cross-sectional dimension portion is configured to prevent tissue from snagging on the proximal end of the engagement feature and is configured to prevent tissue from entering the transverse slit.

16. The surgical instrument according to claim 13, wherein the shank further comprises: (E) a tapered, increased cross-sectional dimension portion disposed adjacent the set of resilient arms configured to prevent tissue interference.

17. The surgical instrument according to claim 13, wherein the plurality of slits includes a pair of opposing longitudinal slits in the shank and a transverse slit extending between the opposing longitudinal slits, wherein the transverse slit extends around at least a part of the axis.

18. The surgical instrument according to claim 17, wherein the tapered, increased cross-sectional dimension portion is configured to prevent tissue from snagging on a proximal end of the engagement feature and is configured to prevent tissue from entering the transverse slit.

19. A surgical instrument for stapling tissue, the instrument comprising:
(a) a body;
(b) a shaft assembly extending from the body, wherein the shaft assembly comprises:
(i) a stapling head assembly, and
(ii) an actuator; and
(c) an anvil configured to be selectively coupled to the actuator, wherein the anvil is configured to cooperate with the stapling head assembly to staple tissue, wherein the anvil comprises:
(i) a head, and
(ii) a shank extending from the head along an axis, the shank comprising:
(A) a proximal end,
(B) a distal end,
(C) a lumen extending from the proximal end toward the distal end,
(D) an engagement feature between the proximal and distal ends, wherein the engagement feature is in communication with the lumen such that the engagement feature is configured to move relative to the axis in response to the actuator being directed into the lumen, wherein the engagement feature is configured to selectively couple the shank to the actuator,
(E) a tapered, increased cross-sectional dimension portion disposed adjacent the engagement feature and configured to prevent tissue interference, and
(F) a pivot limiting member having a proximal end and a distal end, wherein the pivot limiting member is configured to limit the engagement feature pivoting outwardly relative to the axis, wherein when the actuator is partially coupled with the shank, the proximal end of the pivot limiting member is in contact with the engagement feature, and wherein when the actuator is fully coupled with the shank, the proximal end of the pivot limiting member is separated at a distance from the engagement feature.

* * * * *